United States Patent [19]
Browse et al.

[11] Patent Number: 5,952,544
[45] Date of Patent: Sep. 14, 1999

[54] FATTY ACID DESATURASE GENES FROM PLANTS

[75] Inventors: John Browse, Palouse, Wash.; Luis Perez Grau, Davis, Calif.; Anthony J. Kinney, Wilmington, Del.; John W. Pierce, Jr., Wilmington, Del.; Anna M. Wierzbicki, Wilmington, Del.; Narendra S. Yadav, Chadds Ford, Pa.

[73] Assignee: E. I. du Pont de Nemours and Company, Wilmington, Del.

[21] Appl. No.: 08/244,205

[22] PCT Filed: Dec. 3, 1992

[86] PCT No.: PCT/US92/10284

§ 371 Date: Aug. 26, 1994

§ 102(e) Date: Aug. 26, 1994

[87] PCT Pub. No.: WO93/11245

PCT Pub. Date: Jun. 10, 1993

Related U.S. Application Data

[63] Continuation-in-part of application No. 07/804,259, Dec. 4, 1991, abandoned.

[51] Int. Cl.$^6$ .............................. A01H 5/00; C12N 15/82
[52] U.S. Cl. ................... 800/295; 435/69.1; 435/468; 435/320.1; 435/419; 800/281; 536/23.6
[58] Field of Search ..................... 536/23.6; 435/172.3, 435/69.1, 320.1, 240.4, 419; 800/205, DIG. 69; 426/601

[56] References Cited

U.S. PATENT DOCUMENTS

| | | | |
|---|---|---|---|
| 4,394,443 | 7/1983 | Weissman et al. | 435/6 |
| 5,057,419 | 10/1991 | Martin et al. | 435/134 |

FOREIGN PATENT DOCUMENTS

| | | | |
|---|---|---|---|
| WO 91/13972 | 9/1991 | WIPO | C12N 1/21 |

OTHER PUBLICATIONS

Walter, M.H. et al, *Mol. Gen. Genet*, 222, 353–360 (1990).
Browse, J. et al, *Plant Physiol.*, 81, 859–864 (1986).
Wada, H. et al, *Nature*, 347, 200–203 (1990).
Lemieux, B. et al, *Theor. Appl. Genet*, 80, 234–240 (1990).
Brockman, J. et al, *Biological Abstracts*, 89(12), Abstract No. 131194 (Jun. 1990).
Thompson, G.A. et al, *Proc. Natl. Acad. Sci. USA*, 88, 2578–2582 (1991).
Browse, J., *Annu. Rev. Plant Physiol. Plant Mol. Biol.*, 42, 467–506 (1991).
Mattson, F.H. et al, *Journal of Lipid Research*, 26, 194–202 (1985).
Gailliard, T. In: Stumpf, P.K. Ed., *The Biochemistry of Plants*, 4, 85–116, Academic Press, NY (1980).
Mensink, R.P. et al, *New England J. Med.*, N323, 439–445 (1990).
Ohlrogge, J.G. et al, *Biochim. Biophys. Acta.*, 1082, 1–26 (1991).
Knowles, P.F. In, Applewhite, T.H. Ed., *World Conf. on Biotechnology for the Fats and Oils Industry Proceedings*, American Oil Chemists' Society, pp. 35–38 (1980).
Wang, X.M. et al, *Plant Physiol. Biochem.*, 26, 777–792 (1988).
Gunstone et al, Eds. *The Lipds Handbook*, Chapman and Hall, Ltd., Cambridge (1986) pp. 55–112.
Shanklin, J. et al, *Proc. natl. Acad. Sci, USA*, 88, 2510–2514 (1991).
Stukey, J.E. et al, *J. Biol. Chem.*, 265, 20144–20149 (1990).
Thiede, et al, *J. Biol. Chem.*, 261, 13230–13235 (1986).
Kaestner, K.H. et al, *J. Biol. Chem.*, 264, 14755–14756 (1989).
Browse, J. et al, *UCLA Symp. Mol. Cell. Biol.; New Ser., Plant Gene Transfer*, 129, 301–309 (1990).
Somerville, C. et al, *Science*, 252, 80–87 (1991).
Arondel, V. et al, *Science*, 258, 1353–1355 (1992).

*Primary Examiner*—Elizabeth F. McElwain

[57] ABSTRACT

The preparation and use of nucleic acid fragments encoding fatty acid desaturase enzymes are described. The invention permits alteration of plant lipid composition. Chimeric genes incorporating such nucleic acid fragments with suitable regulatory sequences may be used to create transgenic plants with altered levels of unsaturated fatty acids.

14 Claims, No Drawings

FATTY ACID DESATURASE GENES FROM PLANTS

This is a 371 of PCT/US92/10284 filed on Dec. 3, 1992, which is a continuation-in-part of Ser. No. 07/804,259, filed on Dec. 4, 1991 now abandoned.

FIELD OF THE INVENTION

The invention relates to the preparation and use of nucleic acid fragments encoding fatty acid desaturase enzymes to modify plant lipid composition.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to economically produce large amounts of the desired lipid.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids. The relative amounts of saturated and unsaturated fatty acids in commonly used, edible vegetable oils are summarized below (Table 1):

TABLE 1

Percentages of Saturated and Unsaturated Fatty Acids in the Oils of Selected Oil Crops

|  | Saturated | Mono-unsaturated | Poly-unsaturated |
| --- | --- | --- | --- |
| Canola | 6% | 58% | 36% |
| Soybean | 15% | 24% | 61% |
| Corn | 13% | 25% | 62% |
| Peanut | 18% | 48% | 34% |
| Safflower | 9% | 13% | 78% |
| Sunflower | 9% | 41% | 51% |
| Cotton | 30% | 19% | 51% |

Many recent research efforts have examined the role that saturated and unsaturated fatty acids play in reducing the risk of coronary heart disease. In the past, it was believed that mono-unsaturates, in contrast to saturates and poly-unsaturates, had no effect on serum cholesterol and coronary heart disease risk. Several recent human clinical studies suggest that diets high in mono-unsaturated fat and low in saturated fat may reduce the "bad" (low-density lipoprotein) cholesterol while maintaining the "good" (high-density lipoprotein) cholesterol (Mattson et al., Journal of Lipid Research (1985) 26:194–202).

A vegetable oil low in total saturates and high in mono-unsaturates would provide significant health benefits to consumers as well as economic benefits to oil processors. As an example, canola oil is considered a very healthy oil. However, in use, the high level of poly-unsaturated fatty acids in canola oil renders the oil unstable, easily oxidized, and susceptible to development of disagreeable odors and flavors (Gailliard, 1980, Vol.4, pp. 85–116 In: Stumpf, P. K., Ed., The Biochemistry of Plants, Academic Press, New York). The levels of poly-unsaturates may be reduced by hydrogenation, but the expense of this process and the concomitant production of nutritionally questionable trans isomers of the remaining unsaturated fatty acids reduces the overall desirability of the hydrogenated oil (Mensink et al., New England J. Medicine (1990) N323: 439–445). Similar problems exist with soybean and corn oils.

For specialized uses, high levels of poly-unsaturates can be desirable. Linoleate and linolenate are essential fatty acids in human diets, and an edible oil high in these fatty acids can be used for nutritional supplements, for example in baby foods. Linseed oil, derived from the Flax plant (Linum usitatissimum), contains over 50% linolenic acid and has widespread use in domestic and industrial coatings since the double bonds of the fatty acids react rapidly with oxygen to polymerize into a soft and flexible film. Although the oil content of flax is comparable to canola (around 40% dry weight of seed), high yields are only obtained in warm temperatures or subtropical climates. In the USA flax is highly susceptible to rust infection. It will be commercially useful if a crop such as soybean or canola could be genetically transformed by the appropriate desaturase gene(s) to synthesize oils with a high linolenic acid content.

Mutation-breeding programs have met with some success in altering the levels of poly-unsaturated fatty acid levels found in the edible oils of agronomic species. Examples of commercially grown varieties are high (85%) oleic sunflower and low (2%) linolenic flax (Knowles, (1980) pp. 35–38 In: Applewhite, T. E., Ed., World Conference on Biotechnology for the Fats and Oils Industry Proceedings, American Oil Chemists' Society). Similar commercial progress with the other plants shown in Table 1 has been largely elusive due to the difficult nature of the procedure and the pleiotropic effects of the mutational regime on plant hardiness and yield potential.

The biosynthesis of the major plant lipids has been the focus of much research (Browse et al., Ann. Rev. Plant Physiol. Mol. Biol. (1991) 42:467–506). These studies show that, with the notable exception of the soluble stearoyl-acyl carrier protein desaturase, the controlling steps in the production of unsaturated fatty acids are largely catalyzed by membrane-associated fatty acid desaturases. Desaturation reactions occur in plastids and in the endoplasmic reticulum using a variety of substrates including galactolipids, sulfolipids, and phospholipids. Genetic and physiological analyses of *Arabidopsis thaliana* nuclear mutants defective in various fatty acid desaturation reactions indicates that most of these reactions are catalyzed by enzymes encoded at single genetic loci in the plant. The analyses show further that the different defects in fatty acid desaturation can have profound and different effects on the ultra-structural morphology, cold sensitivity, and photosynthetic capacity of the plants (Ohlrogge, et al., Biochim. Biophys. Acta (1991) 1082:1–26). However, biochemical characterization of the desaturase reactions has been meager. The instability of the enzymes and the intractability of their proper assay has largely limited researchers to investigations of enzyme activities in crude membrane preparations. These investigations have, however, demonstrated the role of delta-12 desaturase and delta-15 desaturase activities in the production of linoleate and linolenate from 2-oleoyl-phosphatidylcholine and 2-linoleoyl-phosphatidylcholine, respectively (Wang et al., Plant Physiol. Biochem. (1988) 26:777–792). Thus, modification of the activities of these enzymes represents an attractive target for altering the levels of lipid unsaturation by genetic engineering.

Genes from plants for stearoyl-acyl carrier protein desaturase, the only soluble fatty acid desaturase known, have been described (Thompson, et al., Proc. Natl. Acad. Sci. U.S.A. (1991) 88:2578–2582; Shanklin et al., Proc. Natl. Acad. Sci. USA (1991) 88:2510–2514). Stearoyl-coenzyme-A desaturase genes from yeast, rat, and mice have also been described (Stukey, et al., J. Biol. Chem.(1990) 265:20144–20149; Thiede, et al., J. Biol. Chem. (1986) 261:13230–13235; Kaestner, et al., J. Biol. Chem. (1989) 264:14755–1476). No evidence exists in the public art that describes the isolation of fatty acid desaturases other than stearoyl-ACP desaturases from higher plants or their corresponding genes. A fatty acid desaturase gene from the cyanobacterium, Synechocystis PCC 6803, has also been described (Wada, et al., Nature (1990) 347:200–203). This gene encodes a fatty acid desaturase, designated des A, that catalyzes the conversion of oleic acid at the 1 position of galactolipids to linoleic acid. However, these genes have not proven useful for isolating plant fatty acid desaturases other than stearoyl-ACP desaturase via sequence-dependent protocols, and the present art does not indicate how to obtain plant fatty acid desaturases other than stearoyl-ACP desaturases or how to obtain fatty acid desaturase-related enzymes. Thus, the present art does not teach how to obtain glycerolipid desaturases from plants. Furthermore, there is no evidence that a method to control the nature and levels of unsaturated fatty acids in plants using nucleic acids encoding fatty acid desaturases other than stearoyl-ACP desaturase is known in the art.

The biosynthesis of the minor plant lipids has been less well studied. While hundreds of different fatty acids have been found, many from the plant kingdom, only a tiny fraction of all plants have been surveyed for their lipid content (Gunstone, et al., Eds., (1986) The Lipids Handbook, Chapman and Hall Ltd., Cambridge). Accordingly, little is known about the biosynthesis of these unusual fatty acids and fatty acid derivatives. Interesting chemical features found in such fatty acids include, for example, allenic and conjugated double bonds, acetylenic bonds, trans double bonds, multiple double bonds, and single double bonds in a wide number of positions and configurations along the fatty acid chain. Similarly, many of the structural modifications found in unusual lipids (e.g., hydroxylation, epoxidation, cyclization, etc.) are probably produced via further metabolism following chemical activation of the fatty acid by desaturation or they involve a chemical reaction that is mechanistically similar to desaturation. For example, evidence for the mechanism of hydroxylation of fatty acids being part of a general mechanism of enzyme-catalyzed desaturation in eukaryotes has been obtained by substituting a sulfur atom in the place of carbon at the delta-9 position of stearic acid. When incubated with yeast cell extracts the thiostearate was converted to a 9-sulfoxide (Buist et al. (1987) Tetrahedron Letters 28:857–860). This sulfoxidation was specific for sulfur at the delta-9 position and did not occur in a yeast delta-9-desaturase deficient mutant (Buist & Marecak (1991) Tetrahedron Letters 32:891–894). The 9-sulfoxide is the sulfur analogue of 9-hydroxyoctadecastearate, the proposed intermediate of stearate desaturation. Thus fatty-acid desaturase cDNAs may serve as useful probes for cDNAs encoding fatty-acid hydroxylases and other cDNAs which encode enzymes with reaction mechanisms similar to fatty-acid desaturation. Many of these fatty acids and derivatives having such features within their structure could prove commercially useful if an agronomically viable species could be induced to synthesize them by introduction of a gene encoding the appropriate desaturase.

SUMMARY OF THE INVENTION

Applicants have discovered a means to control the nature and levels of unsaturated fatty acids in plants. Nucleic acid fragments from glycerolipid desaturase cDNAs or genes are used to create chimeric genes. The chimeric genes may be used to transform various plants to modify the fatty acid composition of the plant or the oil produced by the plant. More specifically, one embodiment of the invention is an isolated nucleic acid fragment comprising a nucleotide sequence encoding a plant delta-15 fatty acid desaturase or a fatty acid desaturase-related enzyme with an amino acid identity of 50%, 65%, 90% or greater to the polypeptide encoded by SEQ ID NOS:1, 4, 6, 8, 10, 12, 14, or 16. The isolated fragment in these embodiments is isolated from a plant selected from the group consisting of soybean, oilseed Brassica species, *Arabidopsis thaliana* and corn.

Another embodiment of this invention involves the use of these nucleic acid fragments in sequence-dependent protocols. Examples include use of the fragments as hybridization probes to isolate other glycerolipid desaturase cDNAs or genes. A related embodiment involves using the disclosed sequences for amplification of DNA fragments encoding other glycerolipid desaturases.

Another aspect of this invention involves chimeric genes capable of causing altered levels of the linolenic acid in a transformed plant cell, the gene comprising nucleic acid fragments encoding encoding a plant delta-15 fatty acid desaturase or a fatty acid desaturase-related enzyme with an amino acid identity of 50%, 65%, 90% or greater to the polypeptide encoded by SEQ ID NOS:1, 4, 6, 8, 10, 12, 14, or 16 operably linked in suitable orientation to suitable regulatory sequences. Preferred are those chimeric genes which incorporate nucleic acid fragments encoding delta-15 fatty acid desaturase cDNAs or genes. Plants and oil from seeds of plants containing the chimeric genes described are also claimed.

Yet another embodiment of the invention involves a method of producing seed oil containing altered levels of linolenic (18:3) acid comprising: (a) transforming a plant cell with a chimeric gene described above; (b) growing fertile plants from the transformed plant cells of step (a); (c) screening progeny seeds from the fertile plants of step (b) for the desired levels of linolenic (18:3) acid, and (d) processing the progeny seed of step (c) to obtain seed oil containing altered levels of the unsaturated fatty acids. Preferred plant cells and oils are derived from soybean, rapeseed, sunflower, cotton, cocoa, peanut, safflower, coconut, flax, oil palm, and corn. Preferred methods of transforming such plant cells would include the use of Ti and Ri plasmids of Agrobacterium, electroporation, and high-velocity ballistic bombardment.

The invention also is embodied in a method of breeding plant species to obtain altered levels of poly-unsaturated fatty acids, specifically linolenic (18:3) acid in seed oil of oil-producing plants. This method involves (a) making a cross between two varieties of an oilseed plant differing in the linolenic acid trait; (b) making a Southern blot of restriction enzyme digested genomic DNA isolated from several progeny plants resulting from the cross of step (a); and (c) hybridizing the Southern blot with the radiolabeled nucleic acid fragments encoding the claimed glycerolipid desaturases.

The invention is also embodied in a method of RFLP mapping that uses the isolated *Arabidopsis thaliana* delta-15 desaturase sequences described herein.

The invention is also embodied in plants capable of producing altered levels of glycerolipid desaturase by virtue of containing the chimeric genes described herein. Further, the invention is embodied by seed oil obtained from such plants.

The invention is also embodied in a method of RFLP mapping ina genomic RFLP marker comprising (a) making a cross between two varieties of plants; (b) making a Southern blot of restriction enzyme digested genomic DNA isolated from several progeny plants resulting from the cross of step (a); and (c) hybridizing the Southern blot with a radiolabelled nucleic acid fragments of the claimed fragments.

The invention is also embodied in a method to isolate nucleic acid fragments encoding fatty acid desaturases and fatty acid desaturase-related enzymes, comprising (a)comparing SEQ ID NOS:2, 5, 7, 9, 11, 13, 15 and 17 with other fatty acid desaturase polypeptide sequences; (b) identifying the conserved sequence(s) of 4 or more amino acids obtained in step a; (c) making region-specific nucleotide probe(s) or oligomer(s) based on the conserved sequences identified in step b; and d) using the nucleotide probe(s) or oligomers(s) of step c to isolate sequences encoding fatty acid desaturases and fatty-acid desaturase-related enzymes by sequence-dependent protocols. The product of the method of isolation method described is also part of the invention.

BRIEF DESCRIPTION OF THE SEQUENCE DESCRIPTIONS

The invention can be more fully understood from the following detailed description and the Sequence Descriptions which form a part of this application. The Sequence Descriptions contain the one letter code for nucleotide sequence characters and the three letter code for amino acids in conformity with the IUPAC-IUB standard described in Nucleic Acids Research 13:3021–3030 (19085) and 37 C.F.R. 1.822 which are incorporated herein by reference.

SEQ ID NO:1 shows the complete 5' to 3' nucleotide sequence of 1350 base pairs of the Arabidopsis cDNA which encodes delta-15 desaturase in plasmid pCF3. Nucleotides 46 to 48 are the putative initiation codon of the open reading frame (nucleotides 46 to 1206). Nucleotides 1204 to 1206 are the termination codon. Nucleotides 1 to 45 and 1207 to 1350 are the 5' and 3' untranslated nucleotides, respectively. The 386 amino acid protein sequence in SEQ ID NO:1 is that deduced from the open reading frame.

SEQ ID NO:2 is the deduced peptide of the open-reading frame of SEQ ID NO:1.

SEQ ID NO:3 is a partial nucleotide sequence of the Arabidopsis genomic DNA insert in plasmid pF1 which shows the genomic sequence in the region of the Arabidopsis genome that encodes delta-15 desaturase. Nucleotides 68–255 are identical to nucleotides 1–188 of SEQ ID NO:1. Nucleotides 47 to 49 and 56 to 58 are termination codons in the same reading frame as the open reading frame in SEQ ID NO:1.

SEQ ID NO:4 shows the 5' to 3' nucleotide sequence of the insert in plasmid pACF2-2 of 1525 base pairs of the Arabidopsis thaliana cDNA that encodes a plastid delta-15 fatty acid desaturase. Nucleotides 10–12 and nucleotides 1348 to 1350 are, respectively, the putative initiation codon and the termination codon of the open reading frame (nucleotides 10 to 1350). Nucleotides 1 to 9 and 1351 to 1525 are, respectively, the 5' and 3' untranslated nucleotides.

SEQ ID NO:5 is the deduced peptide of the open reading frame of SEQ ID NO:4.

SEQ ID NO:6 shows the complete 5' to 3' nucleotide sequence of 1336 base pairs of the *Brassica napus* seed cDNA, found in plasmid pBNSF3-2, which encodes a microsomal delta-15 glycerolipid desaturase. Nucleotides 79 to 82 are the putative initiation codon of the open reading frame (nucleotides 79 to 1212). Nucleotides 1210 to 1212 are the termination codon. Nucleotides 1 to 78 and 1213 to 1336 are the 5' and 3' unstranslated nucleotides respectively.

SEQ ID NO:7 is the deduced peptide of the open reading frame of SEQ ID NO:6.

SEQ ID NO:8 is the complete 5' to 3' nucleotide sequence of 1416 base pairs of the *Brassica napus* seed cDNA found in plasmid pBNSFd-2 which encodes a plastid delta-15 glycerolipid desaturase. Nucleotides 1 to 1215 correspond to a continuous open reading frame of 404 amino acids. Nucleotides 1213 to 1215 are the termination codon. Nucleotides 1215 to 1416 are the 3' untranslated nucleotides.

SEQ ID NO:9 is the deduced peptide of the open reading frame of SEQ ID NO:8.

SEQ ID NO:10 is the complete nucleotide sequence of the soybean (glycine max) microsomal delta-15 desaturase cDNA, found in plasmid pXF1, which the 2184 nucleotides of this sequence contain-both the coding sequence and the 5' and 3' non-translated regions of the cDNA. Nucleotides 855 to 857 are the putative initiation codon of the open reading frame (nucleotides 855 to 2000). Nucleotides 1995 to 1997 are the termination codon. Nucleotides 1 to 854 and 1998 to 2184 are the 5' and 3' unstranslated nucleotides respectively. The 380 amino acid protein sequence in SEQ ID NO:7 is that deduced from the open reading frame.

SEQ ID NO:11 is the deduced peptide of the open reading frame in SEQ ID NO:10.

SEQ ID NO:12 is the complete 5' to 3' nucleotide sequence of 1676 base pairs of the soybean (*Glycine max*) seed cDNA found in plasmid pSFD-118bwp which encodes a soybean plastid delta-15 desaturase. Nucleotides 169 to 1530 correspond to a continuous open reading frame of 453 amino acids. Nucleotides 169 to 171 are the putative initiation codon of the open reading frame. Nucleotides 1528 to 1530 are the termination codon. Nucleotides 1531 to 1676 are the 3' untranslated nucleotides. Nucleotides 169 to 382 encode the putative plastid transit peptide, based on comparison of the deduced peptide with the soybean microsomal delta-15 peptide.

SEQ ID NO:13 is the deduced peptide of the open reading frame in SEQ ID NO:12.

SEQ ID NO:14 is the complete nucleotide sequence of a 396 bp polymerase chain reaction product derived from corn seed mRNA that is found in the insert of plasmid pPCR20. Nucleotides 1 to 31 and 364 to 396 correspond to the amplification primers described in SEQ ID NO:18 and SEQ ID NO:19, respectively. Nucleotides 31 to 363 encode an internal region of a corn seed delta-15 desaturase that is 61.9% identical to the region between amino acids 137 and 249 of the Brassica napus delta-15 desaturase peptide sequence shown in SEQ ID NO:7.

SEQ ID NO:15 is the deduced amino acid sequence of SEQ ID NO:14.

SEQ ID NO:16 shows the partial composite 5' to 3' nucleotide sequence of 472 bp derived from the inserts in plasmids pFadx-2 and pYacp7 for *Arabidopsis thaliana* cDNA that encodes a plastid delta-15 fatty acid desaturase. Nucleotides 2–4 and nucleotides 468 to 470 are, respectively, the first and the last codons in the open reading frame.

SEQ ID NO:17 is deduced partial peptide sequence of the open reading frame in SEQ ID NO:16.

SEQ ID NO:18 One hundred and twenty eight fold degenerate sense 31-mer PCR primer. Nucleotides 1 to 8 correspond to the Bam H1 restriction enzyme recognition sequence. Nucleotides 9 to 137 correspond to amino acid residues 130 to 137 of SEQ ID NO:6 with a deoxyinosine base at nucleotide 11.

SEQ ID NO:19 Two thousand and forty eight-fold degenerate antisense 35-mer PCR primer. Nucleotides 1 to 8 correspond to the Bam H1 restriction enzyme recognition sequence. Nucleotides 9 to 35 correspond to amino acid residues 249 to 256 of SEQ ID NO:6 with a deoxyinosine base at nucleotide 15.

SEQ ID NO:20 Sixteen-fold degenerate sense 36-mers made to amino acid residues 97–108 in SEQ ID NO:2.

SEQ ID NO:21 Sixteen-fold degenerate sense 36-mers made to amino acid residues 97–108 in SEQ ID NO:2.

SEQ ID NO:22 Seventy two-fold degenerate sense 18-mers made to amino acid residues 100–105 in SEQ ID NO:2.

SEQ ID NO:23 Seventy two-fold degenerate sense 18-mers made to amino acid residues 100–105 in SEQ ID NO:2.

SEQ ID NO:24 Seventy two-fold degenerate antisense 18-mers made to amino acid residues 299–304 in SEQ ID NO:2.

SEQ ID NO:25 Seventy two-fold degenerate antisense 18-mers made to amino acid residues 299–304 in SEQ ID NO:2.

SEQ ID NO:26 Seventy two-fold degenerate antisense 18-mers made to amino acid residues 304–309 in SEQ ID NO:2.

SEQ ID NO:27 Seventy two-fold degenerate antisense 18-mers made to amino acid residues 304–309 in SEQ ID NO:2.

SEQ ID NO:28 Sixteen-fold degenerate sense 36-mers made to amino acid residues 97–108 in SEQ ID NO:2.

SEQ ID NO:29 Sixteen-fold degenerate sense 36-mers made to amino acid residues 97–108 in SEQ ID NO:2.

SEQ ID NO:30 Sixty four-fold degenerate antisense 38-mers made to amino acid residues 299–311 in SEQ ID NO:2.

SEQ ID NO:31 Sixty four-fold degenerate antisense 38-mers made to amino acid residues 299–311 in SEQ ID NO:2.

SEQ ID NO:32 A 135-mer made as an antisense strand to amino acid residues 97–141 in SEQ ID NO:2.

DETAILED DESCRIPTION OF THE INVENTION

Applicants have isolated nucleic acid fragments that encode plant fatty acid desaturases and that are useful in modifying fatty acid composition in oil-producing species by transformation.

Thus, transfer of the nucleic acid fragments of the invention or a part thereof that encodes a functional enzyme, along with suitable regulatory sequences that direct the transcription of their mRNA, into a living cell will result in the production or over-production of plant fatty acid desaturases and will result in increased levels of unsaturated fatty acids in cellular lipids, including triacylglycerols.

Transfer of the nucleic acid fragments of the invention or a part thereof, along with suitable regulatory sequences that direct the transcription of their antisense RNA, into plants will result in the inhibition of expression of the endogenous fatty acid desaturase that is substantially homologous with the transferred nucleic acid fragment and will result in decreased levels of unsaturated fatty acids in cellular lipids, including triacylglycerols.

Transfer of the nucleic acid fragments of the invention or a part thereof, along with suitable regulatory sequences that direct the transcription of their mRNA, into plants may result in inhibition by cosuppression of the expression of the endogenous fatty acid desaturase gene that is substantially homologous with the transferred nucleic acid fragment and may result in decreased levels of unsaturated fatty acids in cellular lipids, including triacylglycerols.

The nucleic acid fragments of the invention can also be used as restriction fragment length polymorphism (RFLP) markers in Arabidopsis genetic mapping and plant breeding programs.

The nucleic acid fragments of the invention or oligomers derived therefrom can also be used to isolate other related glycerolipid desaturase genes using DNA, RNA, or a library of cloned nucleotide sequences from the same or different species by well known sequence-dependent protocols, including, for example, methods of nucleic acid hybridization and amplification by the polymerase chain reaction.

Definitions

In the context of this disclosure, a number of terms shall be used. The term "fatty acid desaturase" used herein refers to an enzyme which catalyzes the breakage of a carbon-hydrogen bond and the introduction of a carbon-carbon double bond into a fatty acid molecule. The fatty acid may be free or esterified to another molecule including, but not limited to, acyl-carrier protein, coenzyme A, sterols and the glycerol moiety of glycerolipids. The term "glycerolipid desaturases" used herein refers to a subset of the fatty acid desaturases that act on fatty acyl moieties esterified to a glycerol backbone. "Delta-12 desaturase" refers to a fatty acid desaturase that catalyzes the formation of a double bond between carbon positions 6 and 7 (numbered from the methyl end), (i.e., those that correspond to carbon positions 12 and 13 (numbered from the carbonyl carbon) of an 18 carbon-long fatty acyl chain or carbon positions 10 and 11 (numbered from the carbonyl carbon) of a 16 carbon-long fatty acyl chain). "Delta-15 desaturase" refers to a fatty acid desaturase that catalyzes the formation of a double bond between carbon positions 3 and 4 (numbered from the methyl end), (i.e., those that correspond to carbon positions 15 and 16 (numbered from the carbonyl carbon) of an 18 carbon-long fatty acyl chain and carbon positions 13 and 14 (numbered from the carbonyl carbon) of a 16 carbon-long fatty acyl chain). Examples of fatty acid desaturases include, but are not limited to, the microsomal delta-12 and delta-15 desaturases that act on phosphatidylcholine lipid substrates; the chloroplastic delta-12 and delta-15 desaturases that act on phosphatidyl glycerol and galactolipids; and other desaturases that act on such fatty acid substrates such as phospholipids, galactolipids, and sulfolipids. "Microsomal desaturase" refers to the cytoplasmic location of the enzyme, while "chloroplast desaturase" and "plastid desaturase" refer to the plastid location of the enzyme. These fatty acid desaturases may be found in a variety of organisms including, but not limited to, higher plants, diatoms, and various eukaryotic and prokaryotic microorganisms such as fungi and photosynthetic bacteria and algae. The term "homologous fatty acid desaturases" refers to fatty acid desaturases that catalyze the same desaturation on the same lipid substrate. Thus, microsomal delta-15 desaturases, even from different plant species, are homologous fatty acid desaturases. The term "heterologous fatty acid desaturases" refers to fatty acid desaturases that catalyze desaturations at different positions and/or on different lipid substrates. Thus, for example, microsomal delta-12 and delta-15 desaturases, which act on phosphatidylcholine lipids, are heterologous fatty acid desaturases, even when from the same plant. Similarly, microsomal delta-15 desaturase, which acts on phosphatidylcholine lipids, and chloroplast delta-15 desaturase, which acts on galactolipids, are heterologous fatty acid desaturases, even when from the same plant. It should be noted that these fatty acid desaturases have never been isolated and characterized as proteins. Accordingly the terms such as "delta-12 desaturase" and "delta-15 desaturase" are used as a convenience to describe the proteins encoded by nucleic acid fragments that have been isolated based on the phenotypic effects caused by their disruption. The term "fatty acid desaturase-related enzyme" refers to enzymes whose catalytic product may not be a carbon-carbon double bond but whose mechanism of action is similar to that of a fatty acid desaturase (that is, catalysis of the displacement of a carbon-hydrogen bond of a fatty acid chain to form a fatty-hydroxyacyl intermediate or end-product). This term is different from "related fatty acid desaturases", which refers to structural similarities between fatty acid desaturases.

The term "nucleic acid" refers to a large molecule which can be single-stranded or double-stranded, composed of monomers (nucleotides) containing a sugar, a phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to the sequence of DNA or RNA polymers, which can be single- or double-stranded, optionally containing synthetic, non-natural or altered nucleotide bases capable of incorporation into DNA or RNA polymers. The term "oligomer" refers to short nucleotide sequences, usually up to 150 bases long. "Region-specific nucleotide probes" refers to isolated nucleic acid fragments derived from a cDNA or gene using a knowledge of the amino acid regions conserved between different fatty-acid desaturases which may be used to isolate cDNAS or genes for other fatty-acid desaturases or fatty acid desaturase-related enzymes using sequence dependent protocols. As used herein, the term "homologous to" refers to the relatedness between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.); or by the comparison of sequence similarity between two nucleic acids or proteins, such as by the method of Needleman et al. (J. Mol. Biol. (1970) 48:443–453). As used herein, "substantially homologous" refers to nucleotide sequences that have more than 90% overall identity at the nucleotide level with the coding region of the claimed sequence, such as genes and pseudo-genes corresponding to the coding regions. The nucleic acid fragments described herein include molecules which comprise possible variations, both man-made and natural, such as but not limited to (a) those that involve base changes that do not cause a change in an encoded amino acid, or (b) which involve base changes that alter an amino acid but do not affect the functional properties of the protein encoded by the DNA sequence, (c) those derived from deletions, rearrangements, amplifications, random or controlled mutagenesis of the nucleic acid fragment, and (d) even occasional nucleotide sequencing errors.

"Gene" refers to a nucleic acid fragment that expresses a specific protein, including regulatory sequences preceding (5' non-coding) and following (3' non-coding) the coding region. "Fatty acid desaturase gene" refers to a nucleic acid fragment that expresses a protein with fatty acid desaturase activity. "Native" gene refers to an isolated gene with its own regulatory sequences as found in nature. "Chimeric gene" refers to a gene that comprises heterogeneous regulatory and coding sequences not found in nature. "Endogenous" gene refers to the native gene normally found in its natural location in the genome and is not isolated. A "foreign" gene refers to a gene not normally found in the host organism but that is instead introduced by gene transfer. "Pseudo-gene" refers to a genomic nucleotide sequence that does not encode a functional enzyme.

"Coding sequence" refers to a DNA sequence that codes for a specific protein and excludes the non-coding sequences. It may constitute an "uninterrupted coding sequence", i.e., lacking an intron or it may include one or more introns bounded by appropriate splice junctions. An "intron" is a nucleotide sequence that is transcribed in the primary transcript but that is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination respectively, of protein synthesis (mRNA translation). "Open reading frame" refers to the coding sequence uninterrupted by introns between initiation and termination codons that encodes an amino acid sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases.

As used herein, "suitable regulatory sequences" refer to nucleotide sequences in native or chimeric genes that are located upstream (5'), within, and/or downstream (3') to the nucleic acid fragments of the invention, which control the expression of the nucleic acid fragments of the invention. The term "expression", as used herein, refers to the transcription and stable accumulation of the sense (mRNA) or the antisense RNA derived from the nucleic acid fragment(s) of the invention that, in conjunction with the protein apparatus of the cell, results in altered levels of the fatty acid desaturase(s). Expression or overexpression of the gene involves transcription of the gene and translation of the mRNA into precursor or mature fatty acid desaturase proteins. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a foreign gene which has substantial homology to an endogenous gene resulting in the suppression of expression of both the foreign and the endogenous gene. "Altered levels" refers to the production of gene product(s) in transgenic organisms in amounts or proportions that differ from that of normal or non-transformed organisms.

"Promoter" refers to a DNA sequence in a gene, usually upstream (5') to its coding sequence, which controls the expression of the coding sequence by providing the recognition for RNA polymerase and other factors required for proper transcription. In artificial DNA constructs promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryo-genesis, respectively.

The "3' non-coding sequences" refers to the DNA sequence portion of a gene that contains a poly-adenylation signal and any other regulatory signal capable of affecting mRNA processing or gene expression. The polyadenylation signal is usually characterized by affecting the addition of polyadenylic acid tracts to the 3' end of the mRNA precursor.

The term "Transit Peptide" refers to the N-terminal extension of a protein that serves as a signal for uptake and transport of that protein into an organelle such as a plastid or mitochondrion.

"Transformation" herein refers to the transfer of a foreign gene into the genome of a host organism and its genetically stable inheritance. "Restriction fragment length polymorphism" refers to different sized restriction fragment lengths due to altered nucleotide sequences in or around variant forms of genes. "Fertile" refers to plants that are able to propagate sexually.

"Oil-producing species" herein refers to plant species which produce and store triacylglycerol in specific organs, primarily in seeds. Such species include soybean (*Glycine max*), rapeseed and canola (including *Brassica napus*, *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling Brassica species, and *Arabidopsis thaliana*, and wild species which may be a source of unique fatty acids.

"Sequence-dependent protocols" refer to techniques that rely on a nucleotide sequence for their utility. Examples of sequence-dependent protocols include, but are not limited to, the methods of nucleic acid and oligomer hybridization and methods of DNA and RNA amplification such as are exemplified in various uses of the polymerase chain reaction. "PCR product" refers to the DNA product obtained through polymerase chain reaction.

Various solutions used in the experimental manipulations are referred to by their common names such as "SSC", "SSPE", "Denhardt's solution", etc. The composition of these solutions may be found by reference to Appendix B of Sambrook, et al. (Molecular Cloning, A Laboratory Manual, 2nd ed. (1989), Cold Spring Harbor Laboratory Press).

T-DNA Mutagenesis and Identification of an Arabidopsis Mutant Defective in Delta-15 Desaturation In T-DNA mutagenesis (Feldmann, et al., Science (1989) 243:1351–1354), the integration of T-DNA in the genome can interrupt normal expression of the gene at or near the site of the integration. If the resultant mutant phenotype can be detected and shown genetically to be tightly linked to the T-DNA insertion, then the "tagged" locus and its wild type counterpart can be readily isolated by molecular cloning by one skilled in the art.

*Armbidopsis thaliana* seeds were transformed by *Agrobacterium tumefaciens* C58C1rif strain harboring the avirulent Ti-plasmid pGV3850::pAK1003 that has the T-DNA region between the left and right T-DNA borders replaced by the origin of replication region and ampicillin resistance gene of plasmid pBR322, a bacterial kanamycin resistance gene, and a plant kanamycin resistance gene (Feldmann, et al., Mol. Gen. Genetics (1987) 208:1–9). Plants from the treated seeds were self-fertilized and the resultant progeny seeds, germinated in the presence of kanamycin, were self-fertilized to give rise to a population, designated T3, that was segregating for T-DNA insertions. T3 seeds from approximately 6000 T2 plants were analyzed for fatty acid composition. One line, designated 3707, showed a reduced level of linolenic acid (18:3). One more round of self-fertilization of mutant line 3707 produced T4 progeny seeds. The ratio of 18:2/18:3 in seeds of the homogyzous mutant in T4 population was ca. 14; this ratio is ca 1.8 and ca. 23, respectively, in wild-type Arabidopsis and Arabidopsis fad 3 mutant [Lemieux et al. (1990) Theor. App. Gen. 80:234–240] obtained via chemical mutagenesis. These seeds were planted and 263 individual plants were analyzed for the presence of nopaline in leaf extracts. T5 seeds from these plants were further analyzed for fatty acid composition and the ability to germinate in the presence of kanamycin. The mutant fatty acid phenotype was found to segregate in a 1:2:1 ratio, as was germinability on kanamycin. Nopaline was found in all plants with an altered fatty acid phenotype, but not in wild type segregants. These results provided evidence that the locus controlling delta-15 desaturation was interrupted by T-DNA in mutant line 3707.

Isolation of Arabidopsis Genomic DNA Containing the Gene Controlling Delta-15 Desaturation In order to isolate the gene controlling delta-15 desaturation from wild-type Arabidopsis, a T-DNA-plant DNA "junction" fragment containing a T-DNA border integrated into the host plant DNA was isolated from Arabidopsis mutant 3707. For this, genomic DNA from the mutant plant was isolated and completely digested by either Bam HI or Sal I restriction enzymes. In each case, one of the resultant fragments was expected to contain the origin of replication and ampicillin-resistance gene of pBR322 as well as the left T-DNA-plant DNA junction fragment. Such fragments were rescued as plasmids by ligating the digested genomic DNA fragments at a dilute concentration to facilitate self-ligation and then using the ligated fragments to transform *E. coli* cells. Ampicillin-resistant *E. coli* transformants were isolated and screened by colony hybridization to fragments containing either the left or the right T-DNA border. Of the 192 colonies obtained from the plasmid rescue of Sal I digested genomic DNA, 31 hybridized with the left T-DNA border fragment, 4 hybridized to the right T-DNA border fragment, and none hybridized to both. Of the 85 colonies obtained from the plasmid rescue of Bam HI digested genomic DNA, 63 hybridized to the left border and none to the right border. Restriction analysis of seven rescued plasmids that were obtained from the Bam HI digestion and that hybridized to the left T-DNA border showed that they were indistinguishable and contained 1.4 kb of putative, flanking plant DNA. Restriction analysis of another rescued plasmid, pS1, that was obtained from the Sal I digestion and hybridized only to the left T-DNA border, showed that it contained 2.9 kb of putative, flanking plant DNA. This flanking DNA had a Bam HI site and a Hind III site 1.4 kb and 2.2 kb, respectively, away from the left T-DNA border, suggesting that the 1.4 kb putative plant DNA in Bam HI rescued plasmids was contained within the 2.9 kb putative plant DNA in the Sal I rescued plasmids. Southern blot analysis of wild type and mutant 3707 Arabidopsis genomic DNA using the radiolabeled 1.4 kb DNA fragment as the hybridization probe confirmed that this fragment contained plant DNA and that the T-DNA integration site was in a 2.8 kb Bam HI, a 5.2 kb Hind III, a 3.5 kb Sal I, a 5.5 kb Eco RI, and an approximately 9 kb Cla I fragment of wild type Arabidopsis DNA. Nucleotide sequencing of plasmid pS1 with a primer made to a left T-DNA border sequence revealed that pS1 was colinear with the sequence of the left T-DNA border (Yadav et al., Proc. Natl. Acad. Sci. USA (1982) 79:6322–6326) up to nucleotide position 65, which is in the T-DNA border repeats. Approximately 800 bp of additional sequence in pS1 beyond the T-DNA-plant DNA junction, that is, in the plant DNA adjoining the left T-DNA border, showed no significant homology to the T-DNA of pGV3850::pAK1003 and no significant open reading frame.

The nucleic acid fragment from wild-type Arabidopsis corresponding to the plant DNA flanking T-DNA in the line 3707 was isolated by screening a lambda phage *Arabidopsis thaliana* genomic library with the 1.4 kb plant DNA isolated from the rescued plasmids as a hybridization probe. Seven positively-hybridizing genomic clones were isolated that fell in one of five classes based on partial restriction mapping. While their average insert size was approximately 15 kb, taken together they spanned a total of approximately 40 kb of genomic DNA. A combination of restriction and Southern analyses revealed that the five clones overlapped the site of integration of the left border of the T-DNA and that there was no detectable rearrangement of plant DNA in the rescued plasmids as compared to that in the wild type genomic plant DNA. One of these lambda phage clones, designated 1111, was representative of the recovered clones and contained an approximately 20 kb genomic DNA insert which was more or less symmetrically arranged around the site of insertion of the left border of the T-DNA. This clone was deposited on November 27, 1991 with the American Type Culture Collection of Rockville, Maryland under the provisions of the Budapest Treaty and bears accession number ATCC 75167.

Isolation of Arabidopsis Delta-15 Desaturase cDNA

A 5.2 kb Hind III fragment containing wild-type genomic DNA, which hybridized to the 1.4 kb flanking plant DNA recovered from line 3707 and which was interrupted near its middle by the T-DNA insertion in line 3707, was isolated from lambda phage clone 41A1 and cloned into the Hind III site of the pBluescript SK vector (Stratagene) by standard cloning procedures described in Sambrook et al., Molecular Cloning, A Laboratory Manual, 2nd ed. (1989), Cold Spring Harbor Laboratory Press). The resultant plasmid was designated pF1. The isolated 5.2 kb Hind III fragment was also used as a radiolabeled hybridization probe to screen a cDNA library made to poly $A^+$ mRNA from 3-day-old etiolated *Arabidopsis thaliana* (ecotype Columbia) seedling hypocotyls in a lambda ZAP II vector (Stratagene). Of the several positively-hybridizing plaques, four strongly-hybridizing ones were subjected to plaque purification. Sequences of the pBluescript (Stratagene) vector, including the cDNA inserts, from each of the purified phage stocks were excised in the presence of a helper phage. The resultant phagemids were used to infect *E. coli* cells which yielded double-stranded plasmids, pCF1, pCF2, pCF3, and pCF4. All four were shown to contain at least one approximately 1.3 to 1.4 kb Not I insert fragment (Not I/Eco RI adaptors were used in the preparation of the cDNA library) which hybridized to the same region of wild-type plant genomic DNA present in the isolated phage clones. This region, which was near the site of integration of the left T-DNA border in line 3707, was on the side of the T-DNA insertion opposite to that of the plant DNA flanking the left T-DNA border isolated previously via plasmid rescue. Partial sequence determination of the different cDNAs revealed common identity. Since multiple versions of only one type of cDNA were obtained from a cDNA library made from etiolated tissue which is expected to express delta-15 desaturation, and since these cDNAs hybridized to the genomic DNA that corresponds to the site of T-DNA integration in line 3707 which had a high linoleic acid/low linolenic acid phenotype, Applicants were lead to conclude that the T-DNA in line 3707 interrupted the normal expression of the gene encoding delta-15 desaturase. The complete nucleotide sequence of one cDNA, designated pCF3, was determined and is shown as SEQ ID NO:1. It reveals an open reading frame that encodes a 386 amino acid polypeptide. One of the sequencing primers made to the pCF3 insert was also used to obtain 255 bp of sequence from pF1 that is shown as SEQ ID NO:3. Nucleotides 68 to 255 of the genomic DNA in pF1 (SEQ ID NO:3) are identical to nucleotides 1 to 188 of the cDNA (SEQ ID NO:1), which shows that they are colinear and that the cDNA is encoded for by the gene in the isolated genomic DNA. Nucleotides 113 to 115 in SEQ ID NO:3 are the initiation codon of the largest open reading frame corresponding to nucleotides 46–48 in SEQ ID NO:1. This is evident from the presence of in-frame termination codons at nucleotides 47 to 49 and nucleotides 56 to SB and the absence of observable intron splice junctions in SEQ ID NO:3. The identification of the 386 amino acid polypeptide as a desaturase was confirmed by comparing its amino acid sequence with all the protein sequences found in Release 19.0 of the SWISSPROTEIN database using the FASTA algorithm of Pearson and Lipman (Proc. Natl. Acad. Sci. USA (1988) 85:2444–2448) and the BLAST program (Altschul et al., J. Mol. Biol. (1990) 215:403–410). The most homologous protein found in both searches was the desA fatty acid desaturase from the cyanobacterium Synechocystis PCC6803 (Wada, et al., Nature (1990) 347:200–203; Genbank ID:CSDESA; GenBank Accession No:X53508). The 386 amino acid peptide in SEQ ID NO:1 was also compared to the 351 amino acid sequence of desA by the method of Needleman et al. (J. Mol. Biol. (1970) 48:443–453). Over their entire length, these proteins were 26% identical, the comparison imposing four major gaps in the desA protein sequence. While this overall homology is poor, homology in shorter stretches was better. For instance, in a stretch of 78 amino acids the Arabidopsis delta-15 desaturase (amino acids 78 to 155 in SEQ ID NO:1) and the desA protein (amino acids 67 to 144) showed 40% identity and 66% similarity. Homology in yet shorter stretches was even greater as shown in Table 2.

TABLE 2

| Peptide Length | AA positions in SEQ ID NO: 1 | AA positions in desA | Percent Identity |
|---|---|---|---|
| 12 | 97–108 | 86–97 | 83 |
| 7 | 115–121 | 104–110 | 71 |
| 9 | 133–141 | 22–130 | 56 |
| 11 | 299–309 | 282–292 | 64 |

These high percent identities in short stretches of amino acids between the cyanobacterial desaturase polypeptide and SEQ ID NO:2 suggests significant relatedness between the two.

To analyse the developmental expression of the gene encoding mRNA coresponding to SEQ ID NO:1, the cDNA insert in plasmid pCF3 was used as a radiolabeled hybridization probe on mRNA samples from leaf, root, germinating seedling, and developing siliques from both wild type amd mutant 3707 Arabidopsis plants, essentially as described in Maniatis et al., Molecular Cloning, A Laboratory Manual (1982) Cold Spring Harbor Laboratory Press. The results indicated that while the mRNA corresponding to SEQ ID NO:1 is detected in all tissues from the mutant plant, its levels are lower than in wild-type tissues. This is consistent with the observation that the fatty acid mutation in line 3707 is leaky relative to the known Arabidosis fad 3 mutant obtained via chemical mutagenesis. These results confirmed that the T-DNA in line 3707 had interrupted the normal expression of a fatty acid desaturase gene. Based on the fatty acid phenotype of homozygous mutant line 3707, Applicants concluded that the cDNA insert in pCF3 encoded the delta-15 desaturase. Further, Applicants concluded that it was the microsomal delta-15 desaturase, and not the chloroplastic delta-15 desaturase, since: a) the mutant phenotype was expressed strongly in the seed but expressed poorly, if at all, in the leaf of line 3707, and b) the delta-15 desaturase polypeptide, by comparison to the desA polypeptide, did not have an N-terminal extension of a transit peptide expected for a nuclear-encoded chloroplast desaturase.

The identity of SEQ ID NO:2 as the Arabidopsis microsomal delta-15 desaturase was confirmed by its biological overexpression in plant tissues. For this, the 1.4 kB Not I fragment of plasmid pCF3 containing the delta-15 desaturase cDNA was placed in the sense orientation behind either the CaMV 35S promotor, to provide constituitive expression, or behind the promotor for the gene encoding soybean a' subunit of the β-conglycinin (75) seed storage protein, to provide embryo-specific expression. The chimeric genes 35S promoter/sense SEQ ID NO:1/3' nopaline synthase and β-conglycinin/sense SEQ ID NO:1/3' phaseolin were then transformed into plant cells by *Agrobacterium tumefaciens's* binary Ti plasmid vector system [Hoekema et al. (1983) Nature 303:179–180; Bevan (1984) Nucl. Acids Res. 12:8711–8720).

To confirm the identity of SEQ ID NO:1 and to test the biological effect of its overexpression in a heterologous plant species, the chimeric genes 35S promoter/sense SEQ ID NO:1/3' nopaline synthase was transformed into a binary vector, which was then transferred into *Agrobacterium tumefaciens* strain R1000, carrying the Ri plasmid pRiA4b from *Agrobacterium rhizogenes* [Moore et al. (1979) Plasmid 2:617–626]. Carrot (*Daucus carota* L.) cells were transformed by co-cultivation of carrot root disks with strain R1000 carrying the chimeric gene by the method of Petit et al. (1986) [Mol. Gen. Genet. 202:388–393]. Fatty acid analyses of transgenic carrot "hairy" roots show that overexpression of Arabidopsis microsomal delta-15 desaturase can result in over 10-fold increase in 18:3 at the expense of 18:2.

To complement the delta-15 desaturation mutation in the T-DNA mutant line 3707 and to test the biological effect of overexpression of SEQ ID NO:1 in seed, the embryo-specific promoter/SEQ ID NO:1/3' phaseolin chimeric gene was transformed into a binary vector, which was then transformed into the avirulent Agrobacterium strain LBA4404/pAL4404 [Hoekema et al. (1983) Nature 303:179–180]. Roots of line 3707 were transformed by the engineered Agrobacterium, transformed plants were selected and grown to give rise to seeds. Fatty acid analysis of the seeds from two plants showed that the one out of six seeds in each plant showed the mutant fatty acid phenotype, while the remaining seeds show more than 10-fold increase in 18:3 to ca. 55%. While the sample size is small, this segregation suggests Mendelian inheritance of the fatty acid phenotype. While most of the increase occurs at the expense of 18:2, some of it also occurs at the expense of 18:1. Thus, overexpression of this gene in oils crops, especially canola, which is a close relative of Arabidopsis, is also expected to result in the high levels of 18:3 that are found in specialty oil of linseed.

Comparisons of the sequence of the 386 amino acid polypeptide by the method of Needleman et al. (J. Mol. Biol. (1970) 48:443–453) with those for the microsomal stearoyl-CoA (delta-9) desaturases from rat, mouse and yeast revealed 21%, 19%, and 17% identities, respectively. While the membrane-associated Arabidopsis delta-15 desaturase protein showed significant but limited homology to the desA protein, it showed no significant homology to the soluble stearoyl-ACP (delta-9) desaturases from higher plants, including one from Arabidopsis.

Comparison of partial nucleotide sequences of plasmids pF1 and pS1 showed that the left T-DNA border:plant DNA junction is ca. 700 bp from the initiaton codon in SEQ ID NO:1. To determine the position of the other T-DNA:plant DNA junction with respect to the pF1 sequence, the T-DNA:plant DNA junction fragment was isolated.

Genomic DNA from mutant line 3707, isolated as described previously, was partially digested by restriction enzyme Mbo I to give an average fragment size of ca. 15 kB. The fragment ends were partially-filled with dGTP and gATP by Klenow and cloned into Xho I half-sites of LambdaGEM®-11 (Promega Corporation) following the manufacturer's protocol. The phage library was titered and used essentially as described in Ausubel et al. (Current Protocols in Molecular Biology (1989) John Wiley & Sons]. The genomic phage library was screened with radiolabeled PCR product, ca. 0.6 kB, derived from 5' end of the gene in pF1. This product spans from 3 bp to the right of where the left-T-DNA border inserted to 15 bp to the left of nucleotide position 1 in SEQ ID NO:1. Southern blot analysis of DNA from one of the purified, positively-hybridizing phages following Eco RI restriction digestion and electrophoresis showed that a 4 kB Eco RI fragment hybridized to the 0.6 kB PCR product. The Eco RI fragment was subcloned and subject to sequence analyses. Comparison of the sequences derived from this fragment, pF1 and pS1 showed that the insertion of T-DNA resulted in a 56 bp deletion at the site of insertion and that the T-DNA interrupted the Arabidopsis gene 711 bp 5' to the initiaton codon in SEQ ID NO:1. Thus, the T-DNA inserts 5' to the open reading frame, consistent with the leaky expresssion of the gene encoding SEQ ID NO:1 and the leaky fatty acid phenotype in mutant 3707. While the left T-DNA:plant DNA junction is precise, that is without any sequence rearrangement in either the left T-DNA border or the flanking plant DNA, the other T-DNA:plant DNA junction is complex and not fully characterized.

Plasmid pCF3 was deposited on Dec. 3, 1991 with the American Type Culture Collection of Rockville, Md. under the provisions of the Budapest Treaty and bears accession number ATCC 68875.

Using Arabidopsis Delta-15 Desaturase cDNA as a Hybridization Probe to Isolate cDNAs Encoding Related Desaturases from Arabidopsis The 1.4 kb Not I insert fragment isolated from plasmid pCF3 was purified, radiolabeled, and used to screen approximately 80,000 clones from the cDNA library made to poly $A^+$ mRNA from 3-day-old etiolated *Arabidopsis thaliana* as described above, except that lower stringency hybridizations (1 M NaCl, 50 mM Tris-HCl, pH 7.5, 1% SDS, 5% dextran sulfate, 0.1 mg/mL denatured salmon sperm DNA and 50° C.) and washes (sequentially with 2X SSPE, 0.1% SDS at room temperature for 5 min and then again with fresh solution for 10 min, and finally with 0.5X SSPE, 0.1% SDS at 50° C. for 5 min.) were used. Approximately 17 strongly-hybridizing and 17 weakly-hybridizing plaques were identified in the primary screen. Four of the weakly-hybridizing plaques were picked and subjected to one or two further rounds of screening with the radiolabeled probe as above until they were pure. To ensure that these were not delta-15 desaturase clones, they were further analyzed to determine whether they hybridized to an 18 bp oligomer specific to the 3' non-coding region of delta-15 desaturase cDNA (pCF3). After autoradiography of the filters, one of the clones was found not to hybridize to this probe. This clone was picked, and a plasmid clone containing the cDNA insert was obtained as described above. Restriction analysis of this plasmid, designated pCM2, showed that it had an approximately 1.3 kb cDNA insert which lacked a 0.7 kb Nco I—Bgl II fragment characteristic of the Arabidopsis delta-15 desaturase cDNA of pCF3. (This fragment corresponds to the DNA located between the Nco I site at nucleotides 474 to 479 and the Bgl II site at nucleotides 1164 to 1169 in SEQ ID NO:1). Partial nucleotide sequences of single strands from the 5' region and 3' region of pCM2 revealed that the cDNA insert was incomplete and that it encoded a polypeptide that is similar to, but distinct from, that encoded by the cDNA in pCF3. In order to isolate a full-length version of the cDNA in plasmid pCM2, the 1.3 kB Not I fragment from plasmid pCM2 containing the cDNA insert was isolated and used as a radiolabeled hybridization probe to rescreen the same Arabidopsis cDNA library as above. Three strongly hybridizing plaques were purified and the plasmids excised as described previously. The three resultant plasmids were digested by Not I restriction enzyme and shown to contain cDNA inserts ranging in size between 1 kB and 1.5 kB. Complete nucleotide sequence determination of the cDNA insert in one of these plasmids, designated pACF2-2, is shown in SEQ ID NO:4. SEQ ID NO:4 shows the 5' to 3' nucleotide sequence of base pairs of the *Arabidopsis thaliana* cDNA which encodes a fatty acid desaturase. Nucleotides 10–12 and nucleotides 1358 to 1350 are, respectively, the putative initiation codon and the termination codon of the open reading frame (nucleotides 10 to 1350). The open reading frame was confirmed by comparison of its deduced amino acid sequences with that of the related delta-15 fatty acid desaturase from soybean in this application. Nucleotides 1 to 9 and 1351 to 1525 are, respectively, the 5' and 3' untranslated nucleotides. The 446 amino acid protein sequence in SEQ ID NO:5 is that deduced from the open reading frame in SEQ ID NO:4 and has an estimated molecular weight of 51 kD. Alignment of SEQ ID NOS:2 and 5 shows an overall homology of approximately 80% and that the former has an approximately 55 amino acid long N-terminal extension, which is deduced to be a transit peptide found in nuclear-encoded plastid proteins.

To analyse the developmental expression of the gene corresponding to SEQ ID NO:4, this sequence was used as a radiolabeled hybridization probe on mRNA samples from leaf, root, germinating seedling, and developing siliques from both wild type and mutant line 3707 Arabidopsis plants, essentially as described in Maniatis et al. [Molecular Cloning, A Laboratory Manual (1982) Cold Spring Harbor Laboratory Press]. The results indicated that, in contrast to the constitutive expression of the gene encoding SEQ ID NO:1, the mRNA corresponding to SEQ ID NO:4 is abundant in green tissues, rare in roots and leaves, and is about three-fold more abundant in leaf than that of SEQ ID NO:1. The cDNA in plasmid pCM2 was also shown to hybridize polymorphically to genomic DNA from *Arabidopsis thaliana* (ecotype Wassileskija and marker line W100 ecotype Landesberg background) digested with Eco RI. It was used as a RFLP marker to map the genetic locus for the gene encoding this fatty acid desaturase in Arabidopsis. A single genetic locus was positioned corresponding to this desaturase cDNA. Its location was thus determined to be on chromosome 3 between the lambda AT228 and cosmid c3838 RFLP markers, "north" of the glabrous locus (Chang et al., Proc. Natl. Acad. Sci. USA (1988) 85:6856–6860; Nam et al., Plant Cell (1989) 1:699–705). This approximates the region to which Arabidopsis fatty acid desaturase fad 2, fad D, and fad B mutations map [Somerville et al., (1992) in press]. Unsuccessful efforts to clone the microsomal delta-12 fatty acid desaturase using cDNA inserts of pCF3 and pACF2-2 alongwith the above data led Applicants to conclude that the cDNA in pACF2-2 encodes a plastid delta-15 fatty acid desaturase that corresponds to the fad D locus. This conclusion will be confirmed by biological expression of the cDNA in pACF2-2.

Plasmid pCM2 was deposited on Nov. 27, 1991 with the American Type Culture Collection of Rockville, Md. under the provisions of the Budapest Treaty and bears accession number ATCC 68852.

The 1.4 kb, 1.3 kB, and 1.5 kB Not I cDNA insert fragments isolated from plasmids pCF3, pCM2 and pACF2-2 were purified, radiolabeled, and used several times to screen at low stringency as described above two different cDNA libraries: one was made to poly $A^+$ mRNA from 3-day-old etiolated *Arabidopsis thaliana* ("etiolated" library) as described above and one made to polyA$^+$ mRNA from the above-ground parts of *Arabidopsis thaliana* plants, which varied in size from those that had just opened their primary leaves to plants which had bolted and were flowering [Elledge et al. (1991) Proc. Natl. Acad Sci. USA 88:1731–1735]. The cDNA inserts in the library were made into an Xho I site flanked by Eco RI sites in lambda Yes vector [Elledge et al. (1991) Proc. Natl. Acad Sci. USA 88:1731–1735] ("leaf" library). Several plaques from both libraries that hybridized weakly and in duplicate lifts to both SEQ ID NOS:1 and 4 were subjected to plaque purification. Phagemids were excised from the pure phages from "etiolated" library as described above. Plasmids were excised from the purified phages of the "leaf" library by site-specific recombination using the cre-lox recombination system in *E. coli* strain BNN132 [Elledge et al. (1991) Proc. Natl. Acad Sci. USA 88:1731–1735]. In all cases, nucleotide sequencing of the cloned DNA revealed clones either identical to SEQ ID NOS:1 or 4 or unrecognizable sequences.

In another set of experiments ca. 400,000 phages in the "leaf" library was screened with SEQ ID NOS:1 and 4 at low stringency (26 C, 1 M Na$^+$, 50% formamide) and high stringency (42 C, 1 M Na$^+$, 50% formamide). Of the several positive signals on the primary plaque lifts, 11 showed high stringency hybridization to SEQ ID NO:1, 35 showed high stringency hybridization to SEQ ID NO:4, and 39 hybridized to both at low stringency only. Twenty seven plaques of the low stringency signals came through a secondary low-stringency screen, 17 of which were used to make DNA from excised plasmids. Of the 7 plasmid DNA were sequenced, 8 were unrecognizable sequences, 5 were identical to SEQ ID NO:1, 2 were identical to SEQ ID NO:2, and 2 were identical to one another and related but distinct to SEQ ID NOS:1 and 4. The novel desaturase sequence, designated pFad-x2, was also isolated from the "leaf" library independently by using as a hybridization probe a 0.6 kB PCR product derived by polymerase chain reaction on poly A$^+$ RNA made from both canola seed as well as Arabidopsis leaves, as described elsewhere in this application, using degenerate oligomers made to conserved sequences between plant delta-15 desaturases and the cyanobacterial des A desaturase. The PCR-derived plasmid, designated pYacp7, was sequenced partially from both ends. Comparison of the sequences of pFad-x2 and pYacp7 revealed that the two independently cloned cDNAs contained an identical sequence that was related to the other delta-15 desaturases and that both were incomplete cDNAs. A partial composite sequence derived from both plasmids, pFadx-2 and pYacp7, is shown in SEQ ID NO:16 as a 5' to 3' nucleotide sequence of 472 bp. Nucleotides 2–4 and nucleotides 468 to 470 are, respectively, the first and the last codons in the open reading frame. This open reading frame is shown in SEQ ID NO:17. Comparison of SEQ ID NO:17 to the other delta-15 desaturase polypeptides disclosed in this application by the method of Needleman et al. [J. Mol. Biol. (1970) 48:443–453)] using gap weight and gap length weight values of 3.0 and 0.1, respectively. The overall identities are between 65% and 68% between SEQ ID NO:17 and the microsomal delta-15 desaturases from Arabidopsis, canola and soybean and the overall identities are between 77% and 87% between SEQ ID NO:17 and the plastid delta-15 desaturases from Arabidopsis, canola and soybean. In addition SEQ ID NO:17 has an N-terminal peptide extension compared to the microsomal delta-15 desaturases that shows homology of the transit peptide sequence in Arabidopsis plastid delta-15 desaturase. On the basis of these comparisons it is deduced that SEQ ID NO:16 encodes a plastid delta-15 desaturase. There is genetic data in Arabidopsis suggesting the presence of two loci for plastid delta-15 desaturase. The full-length version of SEQ ID NO:16 can be readily isolated by one skilled in the art. The biological effect of introducing SEQ ID NO:16 or its full-length version into plants will be used to confirm its identity.

Plasmid pYacp7 was deposited on Nov. 20, 1992 with the American Type Culture Collection of Rockville, Maryland under the provisions of the Budapest Treaty and bears accession number ATCC 69129.

Using Arabidopsis Delta-15 Desaturase cDNAs as Hybridization Probes to Isolate Delta-15 Desaturase cDNAs from Other Plant Species For the purpose of cloning the *Brassica napus* seed cDNAs encoding delta-15 fatty acid desaturases, the cDNA inserts from pCF3 and pCM2 were isolated by polymerase chain reaction from the respective plasmids, radiolabeled, and used as hybridization probes to screen a lambda phage cDNA library made with poly A$^+$ mRNA from developing *Brassica napus* seeds 20–21 days after pollination. This cDNA library was screened several times at low stringency, using the Arabidopsis cDNA probes mentioned above. One of the *Brassica napus* cDNAs obtained in the initial screens was used as probe in a subsequent high stringency screen.

Arabidopsis pCM2 insert was radiolabeled and used as probe to screen approximately 300,000 plaques under low stringency hybridization conditions. The filter hybridizations were performed in 50 mM Tris pH 7.6, 6X SSC, 5X Denhardt's, 0.5% SDS, 100 ug denatured calf thymus DNA at 50° C. overnight, and the posthybridization washes were carried out in 6X SSC, 0.5% SDS at room temperature for 15 min, then repeated with 2X SSC, 0.5% SDS at 45° C. for 30 min, and then repeated twice with 0.2X SSC, 0.5% SDS at 50° C. for 30 min. Five strongly-hybridizing phages were obtained. These were plaque purified and used to excise the phagemids as described in the manual of the pBluescriptII Phagemid Kit from Stratagene (Stratagene 1991 catalogue, item 212205). One of these, designated pBNSF3-2, contained a 1.3 kb insert. pBNSF3-f2 was sequenced completely on both strands and the nucleotide sequence is shown in SEQ ID NO:6. Plasmid pBNSF3-2 was deposited on Nov. 27, 1991 with the American Type Culture Collection of Rockville Md., USA under the provisions of the Budapest Treaty and bears the accession number 68854.

An additional low stringency screen using pCM2 probe provided eight strongly hybridizing phages. One of these, designated pBNSFd 8, contained a 0.4kb insert. pBNSFd-8 was sequenced completely on one strand, this nucleotide sequence showed significant divergence from the sequence SEQ ID NO:6 in the homologous region, which suggested that it corresponded to a novel *Brassica napus* seed desaturase different from that shown in SEQ ID NO:6. pBNSFd-8 insert was radiolabelled and used as hybridization probe in a high stringency screen of the *Brassica napus* seed cDNA library. The hybridization conditions were identical to those of the low stringency screen described above except for the temperature of the final two 30 min posthybridization washes in 0.2×SSC, 0.5% SDS was increased to 60° C. This screen resulted in three strongly hybridizing phages that were purified and excised. One of the excised plasmids pBNSFd-3 contained a 1.4 kb insert that was sequenced completely on both strands. SEQ ID NO:8 shows the complete nucleotide sequence of pBNSFd-2.

Using Arabidopsis Delta-15 Desaturase cDNA as a Hybridization Probe to Isolate a Glycerolipid Desaturase cDNA from Soybean A cDNA library was made to poly A+ mRNA isolated from developing soybean seeds, and screened essentially as described above, except that filters were prehybridized in 25 mL of hybridization buffer consisting of 50 mM Tris-HCl, pH 7.5, 1 M NaCl, 1% SDS, 5% dextran sulfate and 0.1 mg/mL denatured salmon sperm DNA (Sigma Chemical Co.) at 50° C. for 2 h. Radiolabeled probe prepared from pCF3 as described above was added, and allowed to hybridize for 18 h at 50° C. The probes were washed twice at room temperature with 2X SSPE, 1% SDS for five min followed by washing for 5 min at 50° C. in 0.2X SSPE, 1% SDS. Autoradiography of the filters indicated that there was one strongly hybridizing plaque, and approximately five weakly hybridizing plaques. The more strongly hybridizing plaque was subjected to a second round of screening as before, except that the final wash was for 5 min at 60° C. in 0.2X SSPE, 1% SDS. Numerous, strongly hybridizing plaques were observed, and one, well-isolated from other phage, was picked for further analysis.

Sequences of the pbluescript vector from the purified phage, including the cDNA insert, were excised in the presence of a helper phage and the resultant phagemid was used to infect E. coli XL-1 Blue cells. DNA from the plasmid, designated pXF1, was made by the alkaline lysis miniprep procedure described in Sambrook et al. (Molecular Cloning, A Laboratory Manual, 2nd ed. (1989) Cold Spring Harbor Laboratory Press). The alkali-denatured double-stranded DNA from pXF1 was completely sequenced on both strands. The insert of pXF1 contained a stretch of 1783 nucleotides which contained an unknown open-reading frame and also contained a poly-A stretch of 16 nucleotides 3' to the open reading frame, from nucleotides 1767 to 1783, followed by an Eco RI restriction site. The 2184 bases that followed this Eco RI site contained a 1145 bp open reading frame which encoded a polypeptide of about 68% identity to, and colinear with, the Arabidopsis delta-15 desaturase polypeptide listed in SEQ ID No:2. The putative start methionine of the 1145 bp open-reading frame corresponded to the start methionine of the Arabidopsis microsomal delta-15 peptide and there were no amino acids corresponding to a plastid transit peptide 5' to this methionine. When the insert in pXF1 was digested with Eco RI four fragments were observed, fragments of approximately 370 bp and 1400 bp fragments, derived from the first 1783 bp of the insert in pxF1, and fragments of approximately 600 bp and 1600 bp derived from the the other 2184 nucleotides of the insert in pXF1. Only the 600 bp and 1600 bp fragments hybridized with probe derived from pCF3 on Southern blots. It was deduced that pXF1 contained two different cDNA inserts separated by an Eco RI site and the second of these inserts was a 2184 bp cDNA encoding a soybean microsomal delta-15 desaturase. The complete nucleotide sequence of the 2184 bp soybean microsomal delta-15 cDNA contained in plasmid pXF1 is listed in SEQ ID No:10. Plasmid pXF1 was deposited on Dec. 3, 1991 with the American Type Culture Collection of Rockville, Md. under the provisions of the Budapest Treaty and bears accession number ATCC 68874.

Using Soybean Microsomal Delta-15 Desaturase cDNA as a Hybridization Probe to Isolate cDNAs Encoding Related Desaturases from Soybean A 1.0 kb fragment of DNA corresponding to part of the coding region of the soybean microsomal delta-15 desaturase cDNA contained in plasmid pXF1, was excised with the restriction enzyme Hha I and gel purified. The fragment was labeled with $^{32}p$ as described above and used to probe a soybean cDNA library as described above. Autoradiography of the filters indicated that there were eight hybridizing plaques and these were subjected to a second round of screening. Sequences of the pbluescript vector from all eight of the purified phages, including the cDNA inserts, were excised in the presence of a helper phage and the resultant phagemids were used to infect E. coli XL-1 Blue cells. DNA from the plasmids was made by the alkaline lysis miniprep procedure described in Sambrook et al. (Molecular Cloning, A Laboratory Manual, 2nd ed. (1989) Cold Spring Harbor Laboratory Press). Restriction analysis showed they contained inserts ranging from 1.0 kb to 3.0 kb in size. One of these inserts, designated pSFD-118bwp, contained an insert of about 1700 bp. The alkali-denatured double-stranded DNA from pSFD-118bwp was completely sequenced on both strands, shown in SEQ ID NO:12. The insert of pSFD-118bwp contained a stretch of 1675 nucleotides which contained an open-reading frame encoding a polypeptide, shown in SEQ ID NO:13, of about 80% identity with, and colinear with, the Arabidopsis plastid delta-15 desaturase polypeptide listed in SEQ ID No:5. The open-reading frame also encoded amino acids corresponding to a plastid transit peptide at the 5' end of the open-reading frame. The transit peptide was colinear with, and shared some homology to, the transit peptide described for the Arabidopsis plastid delta-15 glycerolipid desaturase. The complete nucleotide sequence of the 1675 bp soybean plastid delta-15 glycerolipid desaturase cDNA is listed in SEQ ID No:12.

Comparison of the different delta-15 desaturase sequences disclosed in the application by the method of Needleman et al. (J. Mol. Biol. (1970) 48:443–453) using gap weight and gap length weight values of 3.0 and 0.1, respectively, reveals the relatedness between them as shown in Table 3.

TABLE 3

Percent Identities Between Different Delta-15 Fatty Acid Desaturases at the Amino Acid Level

|    | aD | c3 | cD | s3 | sD |
|----|----|----|----|----|----|
| a3 | 66 | 93 | 66 | 68 | 67 |
| aD | —  | 67 | 90 | 67 | 69 |
| c3 | —  | —  | 68 | 68 | 68 |
| cD | —  | —  | —  | 68 | 74 | a3, ad, c3, cD, s3 and sD refer, respectively, to SEQ ID NO:2 (Arabidopsis microsomal delta-15 desaturase), SEQ ID NO:5 (Arabidopsis plastid delta-15 desaturase), SEQ ID NO:7 (canola microsomal delta-15 desaturase), SEQ ID NO:9 (canola plastid delta-15 desaturase), SEQ ID NO:11 (soybean microsomal delta-15 desaturase), and SEQ ID NO:13 (soybean plastid delta-15 desaturase). Based on these comparisons, the delta-15 desaturases, of both microsomal Isolation of Nucleotide Sequences Encoding Homologous and Heterologous Glycerolipid Desaturases Fragments of the instant invention may be used to isolate cDNAs and genes of homologous and heterologous glycerolipid desaturases from the same species as the fragment of the invention or from different species. Isolation of homologous genes using sequence-dependent protocols is well-known in the art. Southern blot analysis revealed that the Arabidopsis microsomal delta-15 desaturase cDNA (SEQ ID NO:1) hybridized to genomic DNA fragments of corn and soybean. In addition, Applicants have demonstrated that it can be used to isolate cDNAs encoding seed microsomal delta-15 desaturases from *Brassica napus* (SEQ ID NO:6) and soybean (SEQ ID NO:10). Thus, one can isolate cDNAs and genes for homologous glycerolipid desaturases from the same or different higher plant species, especially from the oil-producing species.

More importantly, one can use the fragments of the invention to isolate cDNAs and genes for heterologous glycerolipid desaturases, including those found in plastids. Thus, Arabidopsis microsomal delta-15 desaturase cDNA (SEQ ID NO:1) was successfully used as a hybridization probe to isolate cDNAs encoding the related plastid delta-15 desaturases from Arabidopsis (SEQ ID NO:4) and *Brassica napus* (SEQ ID NO: 8), and the soybean microsomal delta-15 soybean (SEQ ID NO:10) was successfully used to isolate soybean cDNA encoding plastid delta-15 desaturase (SEQ ID NO:12).

In a particular embodiment of the present invention, regions of the nucleic acid fragments of the invention that are conserved between different desaturases may be used by one skilled in the art to design a mixture of degenerate oligomers for use in sequence-dependent protocols aimed at isolating nucleic acid fragments encoding other homologous or heterologous glycerolipid desaturase cDNA's or genes. For example, by comparing all desaturase polypeptides one can identify stretches of amino acids that are conserved between them, and then use the conserved amino acid sequence to design oligomers, both short degenerate or long ones, or "guessmers" as known by one skilled in the art (see Sambrook et al., (Molecular Cloning, A Laboratory Manual, 2nd ed. (1989), Cold Spring Harbor Laboratory Press). Such oligomers and "quessmers" may be used as hybridization-probes as known to one skilled in the art.

For example, comparison of cyanobacterial desA and plant delta-15 desaturases revealed a particularly well conserved stretch of amino acids (amino acids 97–108 in SEQ ID NO:1). SEQ ID NOS:20 and 21 represent two sets of 36-mers each 16-fold degenerate made to this region. End-labeled oligomers represented in SEQ ID NOS:20 and 21 were mixed and used as hybridzation probes to screen Arabidopsis cDNA libraries. Most of the positively-hybridizing plaques also hybridized to cDNAs encoding Arabidopsis microsomal and plastid delta-15 desaturases (SEQ ID NOS:1 and 4). However, the use of SEQ ID NOS:20 and 21 did not give consistent and reproducible results. A 135 base-long oligomer (SEQ ID NO:32) was also made as an antisense strand to a longer stretch of the same conserved region, amino acids 97 to 141 in SEQ ID NO:1 (FVLGHDCGHGSFSDIPLLNSVVGHILHSFILVPYHG-WRISHRTHH). At positions of ambiguity, the design used either deoxyinosines or most frequently used codons based on the codon usage in Arabidopsis genes. When used as a hybridization probe, the 135-mer hybridized to all plaques that also hybridized to cDNAs encoding Arabidopsis microsomal and plastid delta-15 desaturases (SEQ ID NOS:1 and 4). In addition, it also hybridized to plaques that did not hybridize to SEQ ID NOS:1 and 4). The latter were purified and excised as described previously. Nucleotide sequencing of the cDNA inserts in the resultant plasmids revealed DNA sequences that did not show any relatedness to any desaturase.

For another example, in the polymerase chain reaction (Innis, et al., Eds, (1990) PCR Protocols: A Guide to Methods and Applications, Academic Press, San Diego), two short pieces of the present fragment of the invention can be used to amplify a longer glycerolipid desaturase DNA fragment from DNA or RNA. The polymerase chain reaction may also be performed on a library of cloned nucleotide sequences with one primer based on the fragment of the invention and the other on either the poly $A^+$ tail or a vector sequence. These oligomers may be unique sequences or degenerate sequences derived from the nucleic acid fragments of the invention. The longer piece of homologous glycerolipid desaturase DNA generated by this method could then be used as a probe for isolating related glycerolipid desaturase genes or cDNAs from Arabidopsis or other species. The design of oligomers, including long oligomers using deoxyinosine, and "guessmers" for hybridization or for the polymerase chain reaction are known to one skilled in the art and discussed in Sambrook et al., (Molecular Cloning, A Laboratory Manual, 2nd ed. (1989), Cold Spring Harbor Laboratory Press). Stretches of conserved amino acids between delta-15 desaturase and other desaturases, especially desA, allow for the design of such oligomers. For example, conserved stretches of amino acids between desA and delta-15 desaturase, discussed above, are useful in designing long oligomers for hybridization as well as shorter ones for use as primers in the polymerase chain reaction. In this regard, the conserved amino acid stretch of amino acids 97 to 108 of SEQ ID NO:2 is particularly useful. Other conserved regions in SEQ ID NO:2 useful for this purpose are amino acids 299 to 309, amino acids 115 to 121, and amino acids 133 to 141. Amino acid stretch 133 to 141 in SEQ ID NO:2 shows especially good homology to several desaturases. For example, in this stretch, amino acids 133, 137, 138, 140 and 141 are conserved in plant delta-15 desaturases, cyanobacterial desA, yeast and mammalian microsomal stearoyl-CoA desaturases. Comparison of cyanobacterial des A and plant delta-15 desaturases revealed two-particularly well conserved stretch of amino acids (amino acids 97–108 and amino acids 299–311 in SEQ ID NO:1) that can be used for PCR. The following sets of PCR primers were made to these regions:

| SEQ ID NO | Length | Fold Degeneracy | AA positions in SEQ ID NO: 2 | AA Sequence |
|---|---|---|---|---|
| 20 | 36 | 16 | 97–108 (S) | FVLGHDCGHGSF |
| 21 | 36 | 16 | 97–108 (S) | FVLGHDCGHGSF |
| 28 | 36 | 16 | 97–108 (S) | FVLGHDCGHGSF |
| 29 | 36 | 16 | 97–108 (S) | FVLGHDCGHGSF |
| 22 | 18 | 72 | 100–105 (S) | GHDCGH |
| 23 | 18 | 72 | 100–105 (S) | GHDCGH |
| 24 | 18 | 72 | 299–304 (AS) | HDIGTH |
| 25 | 18 | 72 | 299–304 (AS) | HDIGTH |
| 26 | 23 | 416 | 304–309 (AS) | HVIHHL |

-continued

| SEQ ID NO | Length | Fold Degeneracy | AA positions in SEQ ID NO: 2 | | AA Sequence |
|---|---|---|---|---|---|
| 27 | 23 | 416 | 304–309 | (AS) | HVIHHL |
| 30 | 38 | 64 | 299–311 | (AS) | HDIGTHVIHHLFP |
| 31 | 38 | 64 | 299–311 | (AS) | HDIGTHVIHHLFP |

In one experiment, PCRs were performed using SEQ ID NOS:22 and 23 as sense primers and either SEQ ID NOS:24 and 25 or SEQ ID NOS:26 and 27 as antisense primers on poly A⁺ RNA purified from both Arabidopsis leaf and canola developing seeds. All PCRs resulted in PCR products of the correct size (ca. 630 bp). The PCR products from Arabidopsis and canola were purified and used as radiolabeled hybridization probes to screen the Lambda Yes Arabidopsis cDNA library, as described above. This led to the isolation of a pure phage, which was excised to give plasmid pYacp7. The cDNA insert in pYacp7 was partially sequenced. It's sequence showed that it encoded an incomplete desaturase polypeptide that was identical to another cDNA (in plasmid pFadx-2) isolated by low-stringency hybridization as described previously. The composite sequence derived from the partial sequences from the cDNA inserts in pFadx-2 and pYacp7 is shown in SEQ ID NO:16 and the polypeptide encoded by it in SEQ ID NO:17. As discussed previously, SEQ ID NO:17 is a putative plastid delta-15 desaturase. This is further supported by Southern blot analysis using radiolabeled cDNA inserts from either pCF3, pACF2-2, or pYacp7 on Arabidopsis genomic DNA digested with one of several enzymes. It shows that the different inserts hybridize to different restriction fragments and that only the inserts from pACF2-2 and pYacp7 show some cross-hybridization.

In another PCR experiment, PCR was performed using ca. 80 pmoles each of SEQ ID NOS:28 and 29 as sense primers and ca. 94 pmoles each of SEQ ID NOS:30 and 31 as antisense primers on poly A⁺ RNA purified from Arabidopsis mutant line 3707. This was performed using GeneAmp® RNA PCR Kit (Perkin Elmer Cetus) following manufacturer's protocol and using the following program: a) 1 cycle of 2 min at 95° C., b) 35 cycles of 1 min at 95° C. (denaturation), 1 min at 50° C. (annealing) and 1 min at 65° C. (extension), and c) 1 cycle of 7 min at 65° C. The resulting PCR product, of the correct size (ca. 630 bp), was purified, radiolabeled, and used as a hybridization probe on a Southern blot of Arabidopsis genomic DNA as described above. While it hybridized to restriction fragments that also hybridized to SEQ ID NOS:1 (Arabidopsis microsomal delta-15 desaturase), 4 (Arabidopsis plastid delta-15 desaturase), and 16 (Arabidopsis plastid delta-15 desaturase), it also hybridized to novel fragments that did not hybridze to previously cloned desaturase cDNAs. However, even after several attempts, the radiolabeled PCR product did not hybridize to any novel cDNA clone when used as a probe on different Arabidopsis cDNA libraries: in all cases it hybridzed only to plaques that also hybridized to the known desaturase cDNAs. Furthermore, the PCR product was subcloned into a plasmid vector and after screening about a 100 of these, none gave rise to a clone with a novel desaturase sequence.

The isolation of other glycerolipid desaturases will become easier as more examples of glycerolipid desaturases are isolated using the fragments of the invention. Knowing the conserved amino acid sequences from diverse desaturases will also allow one to identify more and better consensus sequences. Such sequences can be used to make hybridization probes or amplification primers which will further aid in the isolation of different glycerolipid desaturases, including those from non-plant sources such as fungi, algae, and even cyanobacteria, as well as other membrane-associated desaturases from other organisms.

The function of the diverse nucleotide fragments encoding glycerolipid desaturases that can be isolated using the present invention can be identified by transforming plants with the isolated desaturase sequences, linked in sense or antisense orientation to suitable regulatory sequences required for plant expression, and observing the fatty acid phenotype of the resulting transgenic plants. Preferred target plants for the transformation are the same as the source of the isolated nucleotide fragments when the goal is to obtain inhibition of the corresponding endogenous gene by antisense inhibition or cosuppression. Preferred target plants for use in expression or overexpression of the isolated nucleic acid fragments are plants with known mutations in desaturation reactions, such as the Arabidopsis desaturase mutants, mutant flax deficient in delta-15 desaturation, or mutant sunflower deficient in delta-12 desaturation. Alternatively, the function of the isolated nucleic acid fragments can be determined similarly via transformation of other organisms, such as yeast or cyanobacteria, with chimeric genes containing the nucleic acid fragment and suitable regulatory sequences followed by analysis of fatty acid composition and/or enzyme activity.

Overexpression of the Glycerolipid Desaturase Enzymes in Transgenic Species

The nucleic acid fragment(s) of the instant invention encoding functional glycerolipid desaturase(s), with suitable regulatory sequences, can be used to overexpress the enzyme(s) in transgenic organisms. Such recombinant DNA constructs may include either the native glycerolipid desaturase gene or a chimeric glycerolipid desaturase gene isolated from the same or a different species as the host organism. For overexpression of glycerolipid desaturase(s), it is preferable that the introduced gene be from a different species to reduce the likelihood of cosuppression. For example, overexpression of delta-15 desaturase in soybean, rapeseed, or other oil-producing species to produce altered levels of polyunsaturated fatty acids may be achieved by expressing RNA from the entire cDNA found in pCF3. Similarly, the isolated nucleic acid fragments encoding glycerolipid desaturases from Arabidopsis, rapeseed, and soybean can also be used by one skilled in the art to obtain substantially homologous full-length cDNAs, if not already obtained, as well as the corresponding genes as fragments of the invention. These, in turn, may be used to overexpress the corresponding desaturases in plants. One skilled in the art can also isolate the coding sequencers) from the fragment(s) of the invention by using and/or creating sites for restriction endonucleases, as described in Sambrook et al., (Molecular Cloning, A Laboratory Manual, 2nd ed. (1989), Cold Spring Harbor Laboratory Press). For example, the fragment in SEQ ID NO:1 in plasmid pCF3 is flanked by Not I sites and can be isolated as a Not I fragment that can be introduced in the sense orientation relative to suitable plant regulatory sequences. Alternatively, sites for Nco I (5'-CCATGG-3') or Sph I (5'-GCATGC-3') that allow precise removal of coding sequences starting with the initiating codon "ATG" may be engineered into the fragment(s) of the invention. For example, for utilizing the coding sequence of delta-15 desaturase from pCF3, an Sph I site can be engineered by substituting nucleotides at positions 44, 45, and 49 of SEQ ID NO:1 with G, C, and C, respectively.

Inhibition of Plant Target Genes by Use of Antisense RNA

Antisense RNA has been used to inhibit plant target genes in a tissue-specific manner (see van der Krol et al., Biotechniques (1988) 6:958–976). Antisense inhibition has been shown using the entire cDNA sequence (Sheehy et al., Proc. Natl. Acad. Sci. USA (1988) 85:8805–8809) as well as a partial cDNA sequence (Cannon et al., Plant Molec. Biol. (1990) 15:39–47). There is also evidence that the 3' non-coding sequences (Ch'ng et al., Proc. Natl. Acad. Sci. USA (1989) 86:10006–10010) and fragments of 5' coding sequence, containing as few as 41 base-pairs of a 1.87 kb cDNA (Cannon et al., Plant Molec. Biol. (1990) 15:39–47), can play important roles in antisense inhibition.

The use of antisense inhibition of the glycerolipid desaturases may require isolation of the transcribed sequence for one or more target glycerolipid desaturase genes that are expressed in the target tissue of the target plant. The genes that are most highly expressed are the best targets for antisense inhibition. These genes may be identified by determining their levels of transcription by techniques, such as quantitative analysis of mRNA levels or nuclear run-off transcription, known to one skilled in the art.

For example, antisense inhibition of delta-15 desaturase in *Brassica napus* resulting in altered levels of polyunsaturated fatty acids may be achieved by expressing antisense RNA from the entire or partial cDNA found in pBNSF3-2.

Inhibition of Plant Target Genes by Cosuppression

The phenomenon of cosuppression has also been used to inhibit plant target genes in a tissue-specific manner. Cosuppression of an endogenous gene using the entire cDNA sequence (Napoli et al., The Plant Cell (1990) 2:279–289; van der Krol et al., The Plant Cell (1990) 2:291–299) as well as a partial cDNA sequence (730 bp of a 1770 bp cDNA) (Smith et al., Mol. Gen. Genetics (1990) 224:477–481) are known.

The nucleic acid fragments of the instant invention encoding glycerolipid desaturases, or parts thereof, with suitable regulatory sequences, can be used to reduce the level of glycerolipid desaturases, thereby altering fatty acid composition, in transgenic plants which contain an endogenous gene substantially homologous to the introduced nucleic acid fragment. The experimental procedures necessary for this are similar to those described above for the overexpression of the glycerolipid desaturase nucleic acid fragments. For example, cosuppression of delta-15 desaturase in *Brassica napus* resulting in altered levels of polyunsaturated fatty acids may be achieved by expressing in the sense orientation the entire or partial seed delta-15 desaturase cDNA found in pBNSF3-2.

Selection of Hosts. Promoters and Enhancers

A preferred class of heterologous hosts for the expression of the nucleic acid fragments of the invention are eukaryotic hosts, particularly the cells of higher plants. Particularly preferred among the higher plants are the oil-producing species, such as soybean (*Glycine max*), rapeseed (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), and peanut (*Arachis hypogaea*).

Expression in plants will use regulatory sequences functional in such plants. The expression of foreign genes in plants is well-established (De Blaere et al., Meth. Enzymol. (1987) 153:277–291). The source of the promoter chosen to drive the expression of the fragments of the invention is not critical provided it has sufficient transcriptional activity to accomplish the invention by increasing or decreasing, respectively, the level of translatable mRNA for the glycerolipid desaturases in the desired host tissue. Preferred promoters include (a) strong constitutive plant promoters, such as those directing the 19S and 35S transcripts in cauliflower mosaic virus (Odell et al., Nature (1985) 313:810–812; Hull et al., Virology (1987) 86:482–493), and (b) tissue- or developmentally-specific promoters. Examples of tissue-specific promoters are the light-inducible promoter of the small subunit of ribulose 1,5-bis-phosphate carboxylase (if expression is desired in photosynthetic tissues), the maize zein protein promoter (Matzke et al., EMBO J. (1984) 3:1525–1532), and the chlorophyll a/B binding protein promoter (Lampa et al., Nature (1986) 316:750–752).

Particularly preferred promoters are those that allow seed-specific expression. This may be especially useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., Ann. Rev. Plant Physiol. (1984) 35:191–221; Goldberg et al., Cell (1989) 56:149–160). Moreover, different seed storage proteins may be expressed at different stages of seed development.

Expression of seed-specific genes has been studied in great detail (See reviews by Goldberg et al., Cell (1989) 56:149–160 and Higgins et al., Ann. Rev. Plant Physiol. (1984) 35:191–221). There are currently numerous examples of seed-specific expression of seed storage protein genes in transgenic dicotyledonous plants. These include genes from dicotyledonous plants for bean b-phaseolin (Sengupta-Gopalan et al., Proc. Natl. Acad. Sci. USA (1985) 82:3320–3324; Hoffman et al., Plant Mol. Biol. (1988) 11:717–729), bean lectin (Voelker et al., EMBO J. (1987) 6:3571–3577), soybean lectin (Okamuro et al., Proc. Natl. Acad. Sci. USA (1986) 83:8240–8244), soybean Kunitz trypsin inhibitor (Perez-Grau et al., Plant Cell (1989) 1:095–1109), soybean b-conglycinin (Beachy et al., EMBO J. (1985) 4:3047–3053; pea vicilin (Higgins et al., Plant Mol. Biol. (1988) 11:683–695), pea convicilin (Newbigin et al., Planta (1990) 180:461–470), pea legumin (Shirsat et al., Mol. Gen. Genetics (1989) 215:326–331); rapeseed napin (Radke et al., Theor. Appl. Genet. (1988) 75:685–694) as well as genes from monocotyledonous plants such as for maize 15 kD zein (Hoffman et al., EMBO J. (1987) 6:3213–3221), maize 18 kD oleosin (Lee at al., Proc. Natl. Acad. Sci. USA (1991) 888:6181–6185), barley b-hordein (Marris et al., Plant Mol. Biol. (1988) 10:359–366) and wheat glutenin (Colot et al., EMBO J. (1987) 6:3559–3564). Moreover, promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopis* and *B. napus* seeds (Vandekerckhove et al., Bio/Technology (1989) 7:929–932), bean lectin and bean b-phaseolin promoters to express luciferase (Riggs et al., Plant Sci. (1989) 63:47–57), and wheat glutenin promoters to express chloramphenicol acetyl transferase (Colot et al., EMBO J. (1987) 6:3559–3564).

Of particular use in the expression of the nucleic acid fragment of the invention will be the heterologous promoters from several soybean seed storage protein genes such as those for the Kunitz trypsin inhibitor (Jofuku et al., Plant Cell (1989) 1:1079–1093; glycinin (Nielson et al., Plant Cell (1989) 1:313–328), and b-conglycinin (Harada et al., Plant Cell (1989) 1:415–425). Promoters of genes for a- and b-subunits of soybean β-conglycinin storage protein will be particularly useful in expressing the mRNA or the antisense RNA in the cotyledons at mid- to late-stages of seed development (Beachy et al., EMBO J. (1985) 4:3047–3053) in transgenic plants. This is because there is very little position effect on their expression in transgenic seeds, and the two promoters show different temporal regulation. The promoter for the a-subunit gene is expressed a few days before that for the b-subunit gene. This is important for transforming rapeseed where oil biosynthesis begins about a week before seed storage protein synthesis (Murphy et al., J. Plant Physiol. (1989) 135:63–69).

Also of particular use will be promoters of genes expressed during early embryogenesis and oil biosynthesis. The native regulatory sequences, including the native promoters, of the glycerolipid desaturase genes expressing the nucleic acid fragments of the invention can be used following their isolation by those skilled in the art. Heterologous promoters from other genes involved in seed oil biosynthesis, such as those for B. napus isocitrate lyase and malate synthase (Comai et al., Plant Cell (1989) 1:293–300), delta-9 desaturase from safflower (Thompson et al. Proc. Natl. Acad. Sci. USA (1991) 88:2578–2582) and castor (Shanklin et al., Proc. Natl. Acad. Sci. USA (1991) 88:2510–2514), acyl carrier protein (ACP) from Arabidopsis (Post-Beittenmiller et al., Nucl. Acids Res. (1989) 17:1777), B. napus (Safford et al., Eur. J. Biochem. (1988) 174:287–295),and B. campestris (Rose et al., Nucl. Acids Res. (1987) 15:7197), b-ketoacyl-ACP synthetase from barley (Siggaard-Andersen et al., Proc. Natl. Acad. Sci. USA (1991) 88:4114–4118), and oleosin from *Zea mays* (Lee et al., Proc. Natl. Acad. Sci. USA (1991) 88:6181–6185), soybean (Genbank Accession No: X60773) and B. napus (Lee et al., Plant Physiol. (1991) 96:1395–1397) will be of use. If the sequence of the corresponding genes is not disclosed or their promoter region is not identified, one skilled in the art can use the published sequence to isolate the corresponding gene and a fragment thereof containing the promoter. The partial protein sequences for the relatively-abundant enoyl-ACP reductase and acetyl-CoA carboxylase are also published (Slabas et al., Biochim. Biophys. Acta (1987) 877:271–280; Cottingham et al., Biochim. Biophys. Acta (1988) 954:201–207) and one skilled in the art can use these sequences to isolate the corresponding seed genes with their promoters. Similarly, the fragments of the present invention encoding glycerolipid desaturases can be used to obtain promoter regions of the corresponding genes for use in expressing chimeric genes.

Attaining the proper level of expression of the nucleic acid fragments of the invention may require the use of different chimeric genes utilizing different promoters. Such chimeric genes can be transferred into host plants either together in a single expression vector or sequentially using more than one vector.

It is envisioned that the introduction of enhancers or enhancer-like elements into the promoter regions of either the native or chimeric nucleic acid fragments of the invention will result in increased expression to accomplish the invention. This would include viral enhancers such as that found in the 35S promoter (Odell et al., Plant Mol. Biol. (1988) 10:263–272), enhancers from the opine genes (Fromm et al., Plant Cell (1989) 1:977–984), or enhancers from any other source that result in increased transcription when placed into a promoter operably linked to the nucleic acid fragment of the invention.

Of particular importance is the DNA sequence element isolated from the gene for the a-subunit of b-conglycinin that can confer 40-fold seed-specific enhancement to a constitutive promoter (Chen et al., Dev. Genet. (1989) 10:112–122). One skilled in the art can readily isolate this element and insert it within the promoter region of any gene in order to obtain seed-specific enhanced expression with the promoter in transgenic plants. Insertion of such an element in any seed-specific gene that is expressed at different times than the b-conglycinin gene will result in expression in transgenic plants for a longer period during seed development.

The invention can also be accomplished by a variety of other methods to obtain the desired end. In one form, the invention is based on modifying plants to produce increased levels of glycerolipid desaturases by virtue of introducing more than one copy of the foreign gene containing the nucleic acid fragments of the invention. In some cases, the desired level of polyunsaturated fatty acids may require introduction of foreign genes for more than one kind of glycerolipid desaturase.

Any 3' non-coding region capable of providing a polyadenylation signal and other regulatory sequences that may be required for the proper expression of the nucleic acid fragments of the invention can be used to accomplish the invention. This would include 3' ends of the native glycerolipid desaturase(s), viral genes such as from the 35S or the 19S cauliflower mosaic virus transcripts, from the opine synthesis genes, ribulose 1,5-bisphosphate carboxylase, or chlorophyll a/b binding protein. There are numerous examples in the art that teach the usefulness of different 3' non-coding regions.

Transformation Methods

Various methods of transforming cells of higher plants according to the present invention are available to those skilled in the art (see EPO Pub. 0 295 959 A2 and 0 318 341 A1). Such methods include those based on transformation vectors utilizing the Ti and Ri plasmids of *Agrobacterium spp*. It is particularly preferred to use the binary type of these vectors. Ti-derived vectors transform a wide variety of higher plants, including monocotyledonous and dicotyledonous plants (Sukhapinda et al., Plant Mol. Biol. (1987) 8:209–216; Potrykus, Mol. Gen. Genet. (1985) 199:183). Other transformation methods are available to those skilled in the art, such as direct uptake of foreign DNA constructs (see EPO Pub. 0 295 959 A2), techniques of electroporation (Fromm et al., Nature (1986) (London) 319:791) or high-velocity ballistic bombardment with metal particles coated with the nucleic acid constructs (Kline et al., Nature (1987) (London) 327:70). Once transformed, the cells can be regenerated by those skilled in the art.

Of particular relevance are the recently described methods to transform foreign genes into commercially important crops, such as rapeseed (De Block et al., Plant Physiol. (1989) 91:694–701), sunflower (Everett et al., Bio/Technology (1987) 5:1201), and soybean (Christou et al., Proc. Natl. Acad. Sci USA (1989) 86:7500–7504.

Application to RFLP Technology

The use of restriction fragment length polymorphism (RFLP) markers in plant breeding has been well-documented in the art (Tanksley et al., Bio/Technology (1989) 7:257–264). The nucleic acid fragments of the invention can be used as RFLP markers for traits linked to expression of glycerolipid desaturases. These traits will include altered levels of unsaturated fatty acids. The nucleic acid fragment of the invention can also be used to isolate the glycerolipid desaturase gene from variant (including mutant) plants with altered levels of unsaturated fatty acids. Sequencing of these genes will reveal nucleotide differences from the normal gene that cause the variation. Short oligonucleotides designed around these differences may be used as hybridization probes to follow the variation in polyunsaturates. Oligonucleotides based on differences that are linked to the variation may be used as molecular markers in breeding these variant oil traits.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Example 1

Isolation of Genomic DNA Flanking the T-DNA Site of Insertion in *Arabidopsis thaliana* Mutant Line 3707

Identification of an *Arabidopsis thaliana* T-DNA Mutant with Low Linolenic Acid Content A population of *Arabidopsis thaliana* (geographic race Wassilewskija) transformants containing the T-DNA of *Agrobacterium tumefaciens* was generated by seed transformation as described by Feldmann et al., (Mol. Gen. Genetics (1987) 208:1–9). In this population the transformants contain DNA sequences encoding the pBR322 bacterial vector, nopaline synthase, neomycin phosphotransferase (NPTII, confers kanamycin resistance), and b-lactamase (confers ampicillin resistance) within the T-DNA border sequences. The integration of the T-DNA into different areas of the chromosomes of individual transformants may cause a disruption of plant gene function at or near the site of insertion, and phenotypes associated with this loss of gene function can be analyzed by screening the population for the phenotype.

T3 seed was generated from the wild type seed treated with *Agrobacterium tumefaciens* by two rounds of self-fertilization as described by Feldmann et al., (Science (1989) 243:1351–1354). These progeny were segregating for the T-DNA insertion, and thus for any mutation resulting from the insertion. Approximately 100 seeds of each of 6000 lines were combined and the fatty acid content of each of the 6000 pooled samples was determined by gas chromatography of the fatty acyl methyl esters essentially as described by Browse et al., (Anal. Biochem. (1986) 152:141–145) except that 2.5% $H_2SO_4$ in methanol was used as the methylation reagent and samples were heated for 1.5 h at 80° C. to effect the methanolysis of the seed triglycerides. A line designated "3707" produced seeds that gave an altered fatty acid profile compared to that of the total population. T3 plants were grown from individual T3 seeds produced by line 3707 and self-fertilized to produce T4 seeds on individual plants that were either homozygous wild type, homozygous mutant, or heterozygous for the mutation. The percent fatty acid compositions of a representative subsample of the entire population, of the pooled 3707 T3 seeds, and of a homozygous T4 mutant segregant are shown in Table 4.

TABLE 4

| Fatty Acid Methyl Ester | T3 Pools from lines 3501–4000 average and (std. deviation) | 3707 T3 Pool | 3707 Homozygous T4 Segregant |
|---|---|---|---|
| palmitic | 7.4 (0.37) | 7.0 | 6.4 |
| stearic | 3.0 (0.22) | 2.9 | 3.0 |
| oleic | 17.0 (1.5) | 17.7 | 15.9 |
| linoleic | 29.3 (0.78) | 35.0 | 42.4 |
| linolenic | 16.1 (1.1) | 10.2 | 3.1 |
| eicosenoic | 20.2 (0.73) | 20.5 | 23.6 |

The phenotype of the segregating T3 pool of line 3707 (high linoleic acid, low linolenic acid) was intermediate between that of the population subsample and the homozygous T4 mutant seeds suggesting that line 3707 harbored a mutation at a locus which controls the conversion of linoleic to linolenic acid in the seed. Still, it was not apparent whether the mutant phenotype in line 3707 was the result of a T-DNA insertion. Therefore, Applicants checked a segregating T4 population to determine whether the mutant fatty acid phenotype cosegregated with the nopaline synthase activity and kanamycin resistance encoded by the T-DNA insert. A total of 263 T4 plants were grown and assayed for the presence of nopaline in leaf extracts (Errampalli et al., The Plant Cell (1991) 3:149–157). In addition, T5 seeds were collected from each of the T4 plants and samples of 10–50 seeds were taken to determine the seed fatty acid composition and to determine their ability to germinate in the presence of kanamycin (Feldmann, et al., (1989) Science 243:1351–1354). The 263 plants fell into 3 classes as in Table 5.

TABLE 5

| Number of Individuals | Phenotype |
|---|---|
| 63 | T4 plants: little or no nopaline present; T5 seeds: wild type fatty acid composition, all kanamycin sensitive |
| 134 | T4 plants: nopaline present; T5 seeds: heterozygous fatty acid composition similar to 3707 T3 pool, segregating for kanamycin resistance |
| 64 | T4 plants: nopaline present; T5 seeds homozygous mutant fatty acid composition, all kanamycin resistant |

The cosegregation of the fatty acid phenotype with the phenotypes conferred by T-DNA sequences in an approximately 1:2:1 pattern provided strong evidence that the mutation in line 3707 was the result of a T-DNA insertion. Further experiments were then conducted with the intent of using probes containing T-DNA sequences to clone the T-DNA insert and flanking genomic DNA from line 3707.

Preparation of Genomic DNA from Homozygous 3707 Plants

Seeds from a homozygous line derived from *Arabidopsis thaliana* (geographic race Wassilewskija (WS)) line 3707 were surface sterilized for 5 min at room temperature in a solution of 5.25% sodium hypochlorite (w/v)/0.15% Tween 20 (v/v), then washed several times in sterile distilled water, with a final rinse in 50% ethanol. Immediately following the ethanol wash, the seeds were transferred to sterile filter paper to dry. One to three seeds were then transferred to 250-mL flasks containing 50 mL of sterile Gamborgs B5 media (Gibco, 500–1153EA), pH 6.0. Cultures were incubated at 22° C., 70 $\mu$E·/m$^{-2}$·sec$^{-1}$ of continuous light for approximately three weeks, after which time the root tissue was harvested, made into 10 g aliquots (wet weight), lyophilized, and stored at −20° C.

Using a variation of the procedure of Shure et al., (Cell (1983) 35:225–233) genomic DNA was isolated from the root tissue. Two aliquots of lyophilized tissue were ground to a fine powder using a mortar and pestle. The ground tissue was added to a flask containing 85 mL of lysis buffer (7 M urea, 0.35 M NaCl, 0.05 M Tris-HCl, pH 8.0, 0.02 M EDTA, 1% Sarkosyl, 5% phenol) and mixed gently with a glass rod to obtain a homogeneous suspension. To this suspension an equal volume of phenol:chloroform:isoamyl alcohol (25:24:1) (equilibrated with 10 mM Tris, pH 8, 1 mM EDTA) was added. After the addition of 8.5 mL of 10% SDS the mixture was swirled on a rotating platform for 15 min at room temperature. After centrifugation at 2000×g for 15 min, the upper aqueous phase was removed to a new tube and extracted two more times, as above, but without the addition of SDS. To the final aqueous phase was added 1/20th the volume of 3 M potassium acetate, pH 5.5 and two times the volume of ice cold 100% ethanol. Precipitation of the DNA was facilitated by incubation at −20° C. for one hour followed by centrifugation at 12,000×g for 10 min. The resulting pellet was resuspended in 3 mL of 10 mM Tris, pH 8, 1 mM EDTA to which was added 0.95 g of cesium chloride (CsCl) and 21.4 $\mu$L of 10 mg/mL ethidium bromide (EtBr) per mL of solution. The DNA was then purified by centrifugation to equilibrium in a CsCl/EtBr density gradient for 16 h at 15° C., 265,000×g. After removal from the gradient, the DNA was extracted with isopropanol saturated with TE buffer (10 mM Tris, pH 8; 1 mM EDTA) and CsCl to remove EtBr and then dialyzed overnight at 4° C. against 10 mM Tris, pH 8, 1 mM EDTA to remove CsCl. The DNA was removed from dialysis and the concentration was determined using the Hoechst fluorometric assay in which an aliquot of DNA is added to 3 mL of 1.5×10$^{-6}$ M bis-benzimide (Hoechst 33258, Siga) in 1X SSC (0.15 M NaCl, 0.015 M sodium citrate), pH 7.0, incubated at room temperature for 5 min, and read on a fluorometer at excitation 360, emission 450, against a known set of DNA standards.

Plasmid Rescue and Analysis

Five micrograms of genomic DNA from the homozygous 3707 mutant, prepared as described above, was digested with 20 units of either Bam HI or Sal I restriction enzyme (Bethesda Research Laboratory) in a 50 $\mu$L reaction volume according to the manufacturer's specifications. After digestion the DNA was extracted with buffer-saturated phenol (Bethesda Research Laboratory) followed by precipitation in ethanol. The resulting pellet was resuspended in a final volume of 10 $\mu$L of 10 mM Tris, pH 8, and the concentration of the DNA was determined using the Hoechst fluorometric assay as above.

To facilitate circularization, as opposed to end-to-end joining, a dilute ligation reaction was set up containing 250 ng of Bam HI or Sal I digested genomic DNA, 3 Weiss units of T4 DNA ligase (Promega), 50 $\mu$L of 10X ligase buffer (30 mM Tris-HCl, pH 7.8, 100 mM MgCl$_2$, 100 mM DTT, 5 mM ATP) and 5 $\mu$L of 100 mM ATP in a 500 $\mu$L reaction volume. The reaction was incubated for 16 h at 16° C., heated for 10 min at 70° C., and extracted once with buffer saturated phenol (Bethesda Research Laboratory). The DNA was then precipitated with the addition of two volumes of 100% ethanol and 1/10th volume of 7.5 M ammonium acetate. The resulting pellet was resuspended in a final volume of 10 $\mu$L of 10 mM Tris, pH 8, and the concentration of the DNA was determined using the Hoechst fluorometric assay as above.

Competent DH10B cells (Bethesda Research Laboratory) were transfected with 50 ng of ligated DNA at a concentration of 10 ng of DNA per 100 $\mu$L of cells according to the manufacturer's specifications. Transformants from Sal I or Bam HI digests were selected on LB plates (10 g Bacto-tryptone, 5 g Bacto-yeast extract, 5 g NaCl, 15 g agar per liter, pH 7.4) containing 100 $\mu$g/mL ampicillin or 25 $\mu$g/mL kanamycin sulfate, respectively. Ampicillin-resistant (Amp$^r$; ampicillin sensitivity, Amp$^s$) Sal I tranformants were screened for the presence of the kanamycin resistance (Kan$^r$; kanamycin sensitivity, Kan$^s$) gene by picking primary tranformants and stabbing them first to LB plates containing 100 $\mu$g/mL ampicillin then to LB plates containing 25 $\mu$g/mL kanamycin. After overnight incubation at 37° C. the plates were scored for Amp$^r$/Kan$^s$ colonies. Kanamycin-resistant Bam HI transformants were screened for the presence of the ampicillin resistance gene by picking primary transformants and stabbing them first to LB plates containing 25 $\mu$g/mL kanamycin and then to LB plates containing 100 $\mu$g/mL ampicillin. After overnight incubation at 37° C. the plates were scored for Kan$^r$/Amp$^r$ colonies.

Cultures were made of 192 Amp$^r$/Kan$^s$ Sal I transformants and 85 Kan$^r$/Amp$^r$ Bam HI transformants directly into deep-well microtiter plates containing 200 $\mu$L of LB broth (10 g Bacto-tryptone, 5 g Bacto-yeast extract, 5 g NaCl per liter) with 100 $\mu$g/mL ampicillin. Using the Schleicher and Schuell Minifold I apparatus and Nytran membranes, dot blots were set up, in duplicate, using the following conditions: 50 $\mu$L of culture was diluted into 150 $\mu$L of 5X SSC, the culture was lysed and the DNA denatured by the addition of 150 $\mu$L of 0.5 M NaOH, 1.5 M NaCl solution for 3 min at room temperature, the filter was removed from the apparatus and neutralized in 0.5 M Tris, pH 8, 1.5 M NaCl, the DNA was then UV cross-linked to the filters using the Stratagene Stratalinker, and the filters were heated for 2 h at 80° C. and stored at room temperature.

To determine whether T-DNA was contained within any of the rescued plasmids, the dot blots were probed with portions of the right and left borders of T-DNA. The right border probe consisted of a 2.2 kb Hind III-Dra I fragment of DNA obtained from plasmid H23pKC7 (composed of the 3.2 kb Hind III 23 fragment from Ti plasmid pTiC58 (Lemmers et al., J. Mol. Biol. (1989) 144;353–376) cloned into plasmid vector pKC7 (Maniatis et al., Molecular Cloning, A Laboratory Manual (1982) Cold Spring Harbor Laboratory Press)), and the left border probe consisted of a 2.9 kb Hind III-Eco RI fragment obtained from plasmid H10pKC7 (composed of the 6.5 kb Hind III 10 fragment from Ti plasmid pTiC58 (Lemmers et al., J. Mol. Biol. (1989) 144:353–376) cloned into plasmid vector pKC7 (Maniatis et al., Molecular Cloning, A Laboratory Manual (1982) Cold Spring Harbor Laboratory Press)) using standard digestion, electrophoresis, and electroelution conditions as described in Sambrook et al., (Molecular Cloning, A Laboratory Manual, 2nd ed (1989) Cold Spring Harbor Laboratory Press). Final DNA purification was obtained by passage of the eluted DNA over an Elutip-D column (Schleicher and Schuell) using the manufacturer's specifications. Concentration of the DNA was determined using the Hoechst fluorometric assay as above. Approximately 100 ng of each probe was labeled with a[$^{32}$P]dCTP using a Random Priming Kit from Bethesda Research Laboratories under conditions recommended by the manufacturer. Labeled probe was separated from unincorporated a[$^{32}$P]dCTP by passing the reaction through a Sephadex G-25 spun column under standard conditions as described in Sambrook et al., (Molecular Cloning, A Laboratory Manual, 2nd ed. (1989) Cold Spring Harbor Laboratory Press).

The filters were pre-hybridized in 150 mL of buffer consisting of 6X SSC, 10X Denhardt's solution, 1% SDS, and 100 μg/mL denatured calf thymus DNA for 16 h at –42° C. The denatured, purified, labeled probe was added to the pre-hybridized filters following transfer of the filters to 50 mL of hybridization buffer consisting of 6X SSC, 1% SDS, 10% dextran sulfate, and 50 μg/mL denatured calf thymus DNA. Following incubation of the filters in the presence of the probe for 16 h at 65° C., the filters were washed twice in 150 mL of 6X SSC, 0.5% SDS, twice in 1X SSC, 1% SDS and once in 0.1X SSC, 1% SDS, all at 65° C. The washed filters were subjected to autoradiography on Kodak XAR-2 film at 80° C. overnight.

Of the 85 Bam HI candidates, 63 hybridized with the left border probe and none hybridized with the right border probe. Of the 192 Sal I candidates, 31 hybridized with the left border probe, 4 hybridized with the right border probe, and none hybridized with both probes. Twelve of the Bam HI candidates, 7 positive and 5 negative for the presence of the left border of T-DNA, were further analyzed by restriction digests.

DNA from the Bam HI candidates was made by the alkaline lysis miniprep procedure of Birmbiom et al., (Nuc. Acid Res. (1979) 7:1513–1523), as described in Sambrook et al., (Molecular Cloning, A Laboratory Manual, 2nd ed. (1989), Cold Spring Harbor Laboratory Press). The plasmid DNA was digested with Eco RI restriction enzyme (Bethesda Research Laboratories) in accordance with the manufacturer's specifications and electrophoresed through a 0.8% agarose gel in 1X TBE buffer (0.089 M Tris-borate, 0.089 M boric acid, 0.002 M EDTA). All of the Bam HI candidates which hybridized with the left border probe of T-DNA had the same Eco RI restriction pattern, which indicated the presence of 14.2 kb of T-DNA and 1.4 kb of putative plant genomic DNA in these clones.

DNA from Sal I candidates was isolated, restriction-analyzed using Eco RI, Bam HI and Sal I enzymes, and electrophoresed through a 0.8% agarose gel, as above. All of the Sal I candidates which hybridized with the left border probe of T-DNA included 2.9 kb of putative plant DNA. Contained within this 2.9 kb fragment was a 1.4 kb Bam HI-Eco RI fragment as seen with the Bam HI rescued plasmids, suggesting that the 1.4 kb fragment was a subset of the 2.9 kb fragment and that it was adjacent to the left border of the T-DNA at its site of insertion into the plant genome. Sequence analysis of one Sal I candidate (pSl) using a primer homologous to the left border sequence of T-DNA, revealed that the sequence of pSl was colinear with the sequence of the T-DNA left border (Yadav et al., Proc. Natl. Acad. Sci. USA (1982) 79:6322–6326) up to nucleotide 65, followed by non-T-DNA (putative plant) sequences.

Southern Analysis with Putative Plant DNA from Rescued Plasmids

DNA from the seven Bam HI candidates which hybridized with the left border of the T-DNA was pooled and a portion was digested with Eco RI and Bam HI restriction endonucleases and electrophetically separated on a 0.8% agarose gel in 1X TBE buffer. After excising a 1.4 kb Eco RI-Bam HI fragment from the agarose gel, the 1.4 kb fragment was purified by use of a Gene Clean Kit from Bio 101. Fifty nanograms of the resulting DNA fragment was labeled with a[$^{32}$P]dCTP using a Random Priming Kit (Bethesda Research Laboratory) under conditions recommended by the manufacturer.

Three micrograms of total genomic DNA from homozygous wild-type Arabidopsis and homozygous 3707 mutant Arabidopsis plants was digested to completion with one of the following restriction enzymes: Sal I, Hind III, Eco RI, Cla I, and Bam HI under conditions suggested by the manufacturer. The digested DNA was subjected to electrophoresis and Southern transfer to Hybond-N membranes (Amersham) as described in Sambrook et al. (Molecular Cloning, A Laboratory Approach, 2nd. ed. (1989) Cold Spring Harbor Laboratory Press). After Southern transfer, the membranes were exposed to UV light using the Stratalinker (Stratagene) as per the manufacturer's instructions, air dried, and heated at 68° C. for 2 h.

The filters were prehybridized in 1 M NaCl, 50 mM Tris-Cl, pH 7.5, 1% sodium dodecyl sulfate, 5% dextran sulfate, 100 μg/mL of denatured salmon sperm DNA at 65° C. overnight. Fifty nanograms of the radiolabeled 1.4 kb Eco RI-Bam HI plant DNA fragment prepared above was added to the prehybridization solution containing the Southern blot and further incubated at 65° C. overnight. The filter was washed for 10 min twice in 200 mL 2X SSPE, 0.1% sodium dodecyl sulfate at 65° C. and for 10 min in 200 mL 0.5% SSPE, 0.1% sodium dodecyl sulfate at 65° C. Hybridizing fragments were detected by autoradiography. The analysis confirmed that the probe fragment contained plant DNA and that the T-DNA integration site was in a 2.8 kb Bam HI, a 5.2 kb Hind III, a 3.5 kb Sal I, a 5.5 kb Eco RI, and an approximately 9 kb Cla I fragment of wild type Arabidopsis DNA.

Isolation of Lambda Clones Containing the Wild Type Arabidopsis Delta-15 Desaturase Gene The 1.4 kb Eco RI-Bam HI fragment (see above) was used as a probe to screen a lGem-11 library made from genomic DNA isolated from wildtype *Arabidopsis thaliana* plants, geographic race WS. To construct the library, genomic DNA was partially digested with Sau3A enzyme, and size-fractionated over a salt gradient as described in Sambrook et al. (Molecular Cloning, A Laboratory Approach, 2nd ed. (1989) Cold Spring Harbor Laboratory Press). The size-fractionated DNA was then cloned into Bam HI-digested lGem-11 phage DNA (Promega) following the protocol outlined by the manufacturer. About 25,000 plaque-forming units of phage each were plated on five 150 mm petri plates containing a lawn of KW251 cells on NZY agar media (5 g NaCl, 2 g MgSO$_4$.7H$_2$O, 5 g yeast extract, 10 g NZ Amine (casein hydrolysate from ICN Pharmaceuticals), 15 g agar per liter; pH 7.5). The plaques were adsorbed onto nylon membranes (Colony/Plaque Screen, New England Nuclear), in duplicate, and prepared according to the manufacturer's instructions with the addition of a 2 h incubation at 80° C. after air drying the filters. The filters were prehybridized at 65° C. in hybridization buffer (1% BSA, 0.5 M NaP$_i$, pH 7.2, (NaH$_2$PO$_4$ and Na$_2$HPO$_4$), 10 mM EDTA, and 7% SDS) for 4 h, after which time they were transferred to fresh buffer containing the denatured radiolabeled probe (see above) and incubated overnight at 65° C. The filters were rinsed twice with 0.1X SSC, 1% SDS at 65° C. for 30 min each and subjected to autoradiography on Kodak XA-R film at 80° C. overnight. Seven positively-hybridizing plaques were subjected to plaque purification as described in Sambrook et al., (Molecular Cloning, A Laboratory Manual, 2nd ed. (1989), Cold Spring Harbor Laboratory Press).

Small scale (5 mL) liquid lysates from each of the 7 clones were prepared and titered on KW251 bacteria as described in Sambrook et al. (Molecular Cloning, A Laboratory Manual, 2nd ed (1989), Cold Spring Harbor Laboratory Press). Phage DNA was isolated using a variation of the method of Chisholm (Biotechniques (1989) 7:21–23) in which the initial lysate was made according to Sambrook et al. (Molecular Cloning, A Laboratory Manual, 2nd ed (1989), Cold Spring Harbor Laboratory Press) the concentration of DNase I and RNase I (Sigma) was reduced by half, and the PEG precipitation step was increased to 16 h. Based on restriction analysis using Hind III, Sal I and Xho I enzymes, the original 7 positive phage fell into 5 different classes. While the average insert size was approximately 15 kb, taken together the clones spanned a 40 kb region of genomic DNA. Through restriction mapping using 4 different enzymes (Hind III, Bam HI, Kpn I, and Sal I) singly, and in pair-wise combinations, accompanied by Southern analysis with the 1.4 kb Eco RI-Bam HI probe (as above) and other probes obtained from the 1 clones themselves, a partial map was obtained in which all 5 clones (11111, 141A1, 14211, 14311 and 14411) were found to share an approximately 3 kb region of homology near the site of T-DNA insertion. Via restriction and Southern analysis, Applicants ascertained that a 5.2 kb Hind III fragment present in clones 1111, 41A1, and 4411 also spanned the site of the T-DNA insertion. This fragment was excised from lambda clone 41A1, inserted into the Hind III site of the pBluescript vector (Stratagene), and the resulting plasmid, designated pF1, was prepared and isolated using standard protocols. This Hind III fragment was subsequently used to probe an Arabidopsis cDNA library (see below).

Example 2

Cloning of *Arabidopsis thaliana* Delta-15 Desaturase cDNA Using Genomic DNA Flanking the T-DNA Site of Insertion in *Arabidopsis thaliana* Mutant Line 3707 as a Hybridization Probe The 5.2 kb Hind III fragment from plasmid pF1 was purified by electrophoresis in agarose after digestion of the plasmid with Hind III and radiolabeled with 32p as described above. For the preparation of an Arabidopsis cDNA library, polyadenylated mRNA was prepared from 3 day-old, etiolated Arabidopsis (ecotype Columbia) seedling hypocotyls using standard protocols (Sambrook, et al., Molecular Cloning: A Laboratory Manual, 2nd Ed. (1989) Cold Spring Harbor Laboratory Press). Five micrograms of this mRNA were used as template with an oligo d(T) primer, and Moloney Murine Leukemia Virus reverse transcriptase (Pharmacia) was used to catalyze first strand cDNA synthesis. Second-strand cDNA was made according to Gubler et al., (Gene (1983) 25:263–272) except that DNA ligase was omitted. After the second strand synthesis, the ends of the cDNA were made blunt by reaction with the Klenow fragment of DNA polymerase and ligated to Eco RI/Not I adaptors (Pharmacia). The cDNA's were purified by spun-column chromatography using Sephacryl S-300 and size-fractionated on a 1% low melting point agarose gel. Size-selected cDNAs (1–3 kb) were removed from the gel using agarase (New England Biolabs) and purified by phenol:chloroform extraction and ethanol precipitation. One hundred nanograms of the cDNA was co-precipitated with 1 μg of 1 ZAP II (Stratagene) Eco RI-digested, dephosphorylated arms. The DNAs were ligated in a volume of 4 μL overnight, and the ligation mix was packaged in vitro using the Gigapack II Gold packaging extract (Stratagene).

Approximately 80,000 phage were screened for positively hybridizing plaques using the radiolabeled 5.2 kb Hind III fragment as a probe essentially as described above and in Sambrook et al., (Molecular Cloning: A Laboratory Manual, 2nd ed. (1989) Cold Spring Harbor Laboratory Press). Replica filters of the phage plaques were soaked in 1 M NaCl, 50 mM Tris-HCl, pH 7.5, 1% SDS, 5% dextran sulfate, 0.1 mg/mL denatured salmon sperm DNA during the pre-hybridization step (8 hr at 65° C.) and then probe was added and the hybridization proceeded over 16 hr at the same temperature. Filters were washed sequentially with 2X SSPE, 0.1% SDS at room temperature for 5 min and then again with fresh solution for 10 min, and finally with 0.5X SSPE, 0.1% SDS at 65° C. for 5 min. Approximately 20 positively hybridizing plaques were identified in the primary screen. Four of these were picked and subjected to two further rounds of screening and purification. From the tertiary screen, four pure phage plaques were isolated. Plasmid clones containing the cDNA inserts were obtained through the use of a helper phage according to the in vivo excision protocol provided by Stratagene. Double-stranded DNA was prepared using the alkaline lysis method as previously described, and the resulting plasmids were size-analyzed by electrophoresis in agarose gels. The largest one of these, designated pCF3, contained an approximately 1.4 kb insert which was sequenced using Sequenase T7 DNA polymerase (US Biochemical Corp.) and the manufacturer's instructions, beginning with primers homologous to vector sequences that flank the cDNA insert and continuing serially with primers designed from the newly acquired sequences as the sequencing experiment progressed. The sequence of this insert is shown in SEQ ID NO:1.

Example 3

Cloning of an Arabidopsis cDNA Encoding a Plastid Delta-15 Fatty Acid Desaturase A related fatty acid desaturase was cloned in a similar fashion, except that the probe used was not derived from a PCR reaction on pCF3, but rather was the actual 1.4 kb Not I fragment isolated from pCF3 which was purified and radiolabeled as described above.

Approximately 80,000 phage from the Arabidopsis etiolated hypocotyl cDNA library described above were plated out and screened essentially as before, except as indicated below. The filters were soaked in 1 M NaCl, 50 mM Tris-HC1, pH 7.5, 1% SDS, 5% dextran sulfate, 0.1 mg/mL denatured salmon sperm DNA during the pre-hybridization step (8 hr at 50° C.). Then probe was added and the hybridization proceeded over 16 hr at the same temperature. Filters were washed sequentially with 2X SSPE, 0.1% SDS at room temperature for 5 min and then again with fresh solution for 10 min, and finally with 0.5X SSPE, 0.1% SDS at 50° C. for 5 min. Approximately 17 strongly hybridizing and 17 weakly hybridizing plaques were identified in the primary screen. Four of the weakly hybridizing plaques were picked and subjected to one to two further rounds of screening with the radiolabeled probe as above until they were pure. To ensure that these were not delta-15 desaturase clones, they were further analyzed to determine whether they hybridized to a delta-15 desaturase 3' end-specific probe. The probe used was an 18 bp oligonucleotide which is complementary in sequence (i.e., antisense) to nucleotides 1229–1246 of SEQ ID NO:1. The probe was radiolabeled with gamma-$^{32}$P ATP using T4 polynucleotide kinase and hybridized to filters containing DNA from the isolated clones in 6X SSC, 5X Denhardt's, 0.1 mg/mL denatured salmon sperm DNA, 1 mM EDTA, 1% SDS at 44° C. overnight. The filters were washed twice in 6X SSC, 0.1% SDS for 5 min at room temperature, then in 6X SSC, 0.1% SDS at 44° C. for 3–5 min. After autoradiography of the filters, one of the clones failed to show hybridization to this probe. This clone was picked, and a plasmid clone containing the cDNA insert was obtained through the use of a helper phage according to the in vivo excision protocol provided by Stratagene. Double-stranded DNA was prepared using the alkaline lysis method as previously described, and the resulting plasmid was size-analyzed by electrophoresis in agarose gels following either Not I digestion or digestion with both Nco I and Bgl II. The results were consistent with the presence in this plasmid, designated pCM2, of an approximately 1.3 kb cDNA insert which lacked a 0.7 kb Nco I—Bgl II fragment characteristic of the Arabidopsis delta-15 desaturase cDNA of pCF3. (This fragment corresponds to the DNA located between the Nco I site at nucleotides 474–479 and the Bgl II site at nucleotides 1164–1169 in SEQ ID NO:1). The complete nucleotide sequence of pCM2 is shown in SEQ ID NO:4.

Example 4

Cloning of Plant Fatty Acid Desaturase cDNAs from Other Species by Hybridization Techniques An approximately 1.4 kb fragment containing the Arabidopsis delta-15 desaturase coding sequence of SEQ ID NO:1 was obtained from plasmid pCF3 through the use of the polymerase chain reaction (PCR). Primers (M13(-20) and T7-17mer primers, 1991 Stratagene Catalogue numbers 300303 and 300302, respectively) flanking the pCF3 insert were used in the PCR which was carried out essentially as described in the instructions provided by the vendor in the Perkin-Elmer/Cetus PCR kit. This fragment was digested with Not I to remove vector sequences, purified by agarose gel electrophoresis, and radiolabeled with $^{32}$P as previously described.

Example 5

Cloning of Brassica napus Seed cDNAs Encoding Delta-15 Fatty Acid Desaturases

A cDNA library from developing Brassica napus seeds was constructed using the polyadenylated mRNA fraction contained in a polysomal RNA preparation from developing Brassica napus seeds. Polysomal RNA was isolated following the procedure of Kamalay et al., (Cell (1980) 19:935–946) from seeds 20–21 days after pollination. The polyadenylated mRNA fraction was obtained by affinity chromatography on oligo-dT cellulose (Aviv et al., Proc. Natl. Acad. Sci. USA (1972) 69:1408–1411). Four micrograms of polyadenylated mRNA were reverse transcribed and used to construct a cDNA library in lambda phage (Uni-ZAP™ XR vector) using the protocol described in the ZAP-cDNA™ Synthesis Kit (1991 Stratagene Catalog, Item # 200400).

For the purpose of cloning the Brassica napus seed cDNAs encoding delta-15 fatty acid desaturases, the Brassica napus seed cDNA library was screened several times using the inserts from the Arabidopsis cDNAs pCF3 and pCM2 as radiolabelled hybridization probes. One of the Brassica napus cDNAs obtained in these screens was used as hybridization probe in a subsequent screen.

For each screening experiment approximately 300,000 phages were screened under low stringency hybridization conditions. The filter hybridizations were carried out in 50 mM Tris pH 7.6, 6X SSC, 5X Denhardt's, 0.5% SDS, 100 ug denatured calf thymus DNA at 50° C. overnight and the p[ost hybridization washes were performed in 6X SSC, 0.5% SDS at room temperature for 15 min, then repeated with 2X SSC, 0.5% SDS at 45° C. for 30 min, and then repeated twice with 0.2x SSC, 0.5% SDS at 50° C. for 30 min.

Using the Arabidopsis cDNA insert of pCM2 as a probe in a low stringency screen five strongly hybridizing phages were identified. These phages were purified and excised according to the protocols described in the ZAP-cDNA™ Synthesis Kit and pBluescript II Phagemid Kit (1991 Stratagene Catalog, Item # 200400 and 212205). One of these, designated pBNSF3-f2, contained a 1.3 kb insert. pBNSF3-f2 insert was sequenced completely on both strands. pBNSF3-f2 nucleotide sequence is shown in SEQ ID NO:6. A comparison of this sequence with that of the Arabidopsis thaliana delta-15 desaturase clone (SEQ ID NO:1) confirmed that pBNSF3-f2 is a Brassica napus cDNA that encodes a seed microsomal delta-15 desaturase.

An additional low stringency screen of the Brassica napus seed cDNA library using the cDNA insert in pCM2 as a probe identified eight strongly-hybridizing phages. These phages were plaque purified and used to excise the phagemids as described above. One of these, designated pBNSFd-8, contained a 0.3 kb insert. pBNSFd-8 was sequenced completely on one strand, this sequence had significant divergence from the sequence of pBNSF3-f2. The cDNA insert in pBNSFd-8 was used as a hybridization probe in a high stringency screen of the Brassica napus seed cDNA library. The filter hybridizations were carried out in 50 mM Tris pH 7.6, 6X SSC, SX Denhardt's, 0.5% SDS, 100 ug denatured calf thymus DNA overnight at 50° C. and post hybridization washes were in 6X SSC, 0.5% SDS at room temperature for 15 min, then with 2X SSC, 0.5% SDS at 45° C. for 30 min, and then twice with 0.2X SSC, 0.5% SDS at 60° C. for 30 min. The high stringency screen resulted in three strongly hybridizing phages that were purified and excised as above. One of the excised plasmids pBNSFd-3 contained a 1.4 kb insert that was sequenced completely on both strands. SEQ ID NO:8 shows the nucleotide sequence of pBNSFd-3. A comparison of this sequence with that of the Arabidopsis thaliana delta-15 desaturase clone (SEQ ID NO:4) confirmed that pBNSFd-3 is a Brassica napus cDNA that encodes a seed plastid delta-15 desaturase.

Cloning of a Soybean Seed cDNA Encoding a Microsomal Delta-15 Glycerolipid Desaturase A cDNA library was made as follows: Soybean embryos (ca. 50 mg fresh weight each) were removed from the pods and frozen in liquid nitrogen. The frozen embryos were ground to a fine powder in the presence of liquid nitrogen and then extracted by Polytron homogenization and fractionated to enrich for total RNA by the method of Chirgwin et al. (Biochemistry (1979) 18:5294–5299). The nucleic acid fraction was enriched for poly A$^+$RNA by passing total RNA through an oligo-dT cellulose column and eluting the poly A+RNA with salt as described by Goodman et al. (Meth.

Enzymol. (1979) 68:75–90). cDNA was synthesized from the purified poly A+RNA using cDNA Synthesis System (Bethesda Research Laboratory) and the manufacturer's instructions. The resultant double-stranded DNA was methylated by Eco RI DNA methylase (Promega) prior to filling-in its ends with T4 DNA polymerase (Bethesda Research Laboratory) and blunt-end ligation to phosphorylated Eco RI linkers using T4 DNA ligase (Pharmacia). The double-stranded DNA was digested with Eco RI enzyme, separated from excess linkers by passage through a gel filtration column (Sepharose CL-4B), and ligated to lambda ZAP vector (Stratagene) according to manufacturer's instructions. Ligated DNA was packaged into phage using the Gigapack packaging extract (Stratagene) according to manufacturer's instructions. The resultant cDNA library was amplified as per Stratagene's instructions and stored at –80° C.

Following the instructions in the Lambda ZAP Cloning Kit Manual (Stratagene), the cDNA phage library was used to infect *E. coli* BB4 cells and approximately 80,000 plaque forming units were plated onto 150 mm diameter petri plates. Duplicate lifts of the plates were made onto nitrocellulose filters (Schleicher & Schuell). The filters were prehybridized in 25 mL of hybridization buffer consisting of 50 mM Tris-HCl, pH 7.5, 1 M NaCl, 1% SDS, 5% dextran sulfate and 0.1 mg/mL denatured salmon sperm DNA (Sigma Chemical Co.) at 50° C. for 2 h. Radiolabeled probe prepared from pCF3 as described above was added, and allowed to hybridize for 18 h at 50° C. The probes were washed twice at room temperature with 2X SSPE, 1% SDS for five minutes followed by washing for 5 min at 50° C. in 0.2X SSPE, 1% SDS. Autoradiography of the filters indicated that there was one strongly hybridizing plaque, and approximately five weakly hybridizing plaques. The more strongly hybridizing plaque was subjected to a second round of screening as before, excepting that the final wash was for 5 min at 60° C. in 0.2X SSPE, 1% SDS. Numerous, strongly hybridizing plaques were observed, and one, well-isolated from other phage, was picked for further analysis.

Following the Lambda ZAP Cloning Kit Instruction Manual (Stratagene), sequences of the pBluescript vector, including the cDNA inserts, from the purified phage was excised in the presence of a helper phage and the resultant phagemid was used to infect *E. coli* XL-1 Blue cells. DNA from the plasmid, designated pXF1, was made by the alkaline lysis miniprep procedure described in Sambrook et al. (Molecular Cloning, A Laboratory Manual, 2nd ed. (1989) Cold Spring Harbor Laboratory Press). The alkali-denatured double-stranded DNA from pXF1 was completely sequenced on both strands. The insert of pXF1 contained a stretch of 1783 nucleotides which contained an unknown open-reading frame and also contained a poly-A stretch of 16 nucleotides 3' to the open reading frame, from nucleotides 1767 to 1783, followed by an Eco RI restriction site. The 2184 bases that followed this Eco RI site contained a 1145 bp open reading frame which encoded a polypeptide of about 68% identity to, and colinear with, the Arabidopsis delta-15 desaturase polypeptide listed in SEQ ID No:2. The putative start methionine of the 1145 bp open-reading frame corresponded to the start methionine of the Arabidopsis microsomal delta-15 peptide and there were no amino acids corresponding to a plastid transit peptide 5' to this methionine. When the insert in pXF1 was digested with Eco RI four fragments were observed, fragments of approximately 370 bp and 1400 bp fragments, derived from the first 1783 bp of the insert in pXF1, and fragments of approximately 600 bp and 1600 bp derived from the the other 2184 nucleotides of the insert in pXF1. Only the 600 bp and 1600 bp fragments hybridized with probe derived from pCF3 on Southern blots. It was deduced that pXF1 contained two different cDNA inserts separated by an Eco RI site and the second of these inserts was a 2184 bp cDNA encoding a soybean microsomal delta-15 desaturase. The complete nucleotide sequence of the 2184 bp soybean microsomal delta-15 cDNA contained in plasmid pXF1 is listed in SEQ ID No:10.

Cloning of a Soybean Seed cDNA Encoding a Plastid Delta-15 Glycerolipid Desaturase Using Soybean Microsomal Delta-15 Desaturase cDNA as an Hybridization Probe A 1.0 kb fragment of the coding region of the soybean microsomal delta-15 desaturase cDNA contained in plasmid pXF1 was excised by digestion with the restriction enzyme Hha I. This 1.0 Kb fragment was purified by agarose gel electrophoresis and radiolabeled with 32P as previously described. The radiolabeled fragment was used to screen 100,000 plaque-forming units of the the soybean cDNA library as described above. Autoradiography of the filters indicated that there were eight hybridizing plaques and these were subjected to a second round of screening. Sequences of the pBluescript vector from all eight of the purified phages, including the cDNA inserts, were excised in the presence of a helper phage and the resultant phagemids were used to infect *E. coli* XL-1 Blue cells. DNA from the plasmids was made by the alkaline lysis miniprep procedure described in Sambrook et al. (Molecular Cloning, A Laboratory Manual, 2nd ed. (1989) Cold Spring Harbor Laboratory Press). Restriction analysis showed they contained inserts ranging from 1.0 kb to 3.0 kb in size. One of these inserts, designated pSFD-118bwp, contained an insert of about 1700 bp. The alkali-denatured double-stranded DNA from pSFD-118bwp was completely sequenced on both strands. The insert of pSFD-118bwp contained a stretch of 1675 nucleotides which contained an open-reading frame encoding a polypeptide of about 80% identity with, and colinear with, the Arabidopsis plastid delta-15 desaturase polypeptide listed in SEQ ID No:5. The open-reading frame also encoded amino acids corresponding to a plastid transit peptide at the 5' end of the open-reading frame. The transit peptide was colinear with, and shared some homology to, the transit peptide described for the Arabidopsis plastid delta-15 glycerolipid desaturase. Based on the homology to Arabidopsis plastid delta-15 glycerolipid desaturase and because of the presence of a plastid transit peptide, the cDNA contained in plasmid pSFD-118bwp was deduced to be a soybean plastid delta-15 glycerolipid desaturase. The complete nucleotide sequence of the 1675 bp soybean plastid delta-15 glycerolipid desaturase cDNA is listed in SEQ ID NO:12.

EXAMPLE 6

Cloning of cDNA Sequences Encoding Fatty Acid Desaturases By Polymerase Chain Reaction Analysis of the deduced protein sequences of the different higher plant glycerolipid desaturases described in this invention reveals to those skilled in the art regions of the amino acid sequences that have been conserved among higher plants and between higher plants and cyanobacterial des A. These short stretches of amino acids can be used to design oligomers as primers for polymerase chain reactions. Two amino acid sequences that are highly conserved between the des A and plant delta-15 desaturases polypeptides are amino acid sequences 97–108 and 299–311 (SEQ ID NO:2). Polymerase chain reactions (PCRs) were performed using Gene- Amp® RNA PCR Kit (Perkin Elmer Cetus) following manufacturer's protocols. In one PCR experiment, SEQ ID NOS:22 and 23 were used as sense primers and either SEQ ID NOS:24 and 25 or SEQ ID NOS:26 and 27 as antisense primers on poly A+ RNA purified from both Arabidopsis leaf and canola developing seeds. For this, ca. 100 ng of polyA+ RNA was isolated as described previously and reverse-transcribed using the kit using random hexamers. Then the cDNA was used in PCR using 64 pmoles each of SEQ ID NOS:22 and 23 as sense primers and either a mixture of 64 pmoles of SEQ ID NO:24 and 78 pmoles of SEQ ID NO:25 or a mixture 35 pmoles of SEQ ID NO:26 and 50 pmoles of SEQ ID NO:27 by the following program: a) 1 cycle of 2 min at 95° C. and 15 C at 50° C., b) 30 cycles of 3 min at 65° C. (extension), 1 min 20 sec at 95° C. (denaturation), 2 min at 50° C. (annealing), and c) 1 cycle of 7 min at 65° C. PCR products were analyzed by gel electrophoresis. All PCRs resulted in PCR products of the correct size (ca. 630 bp). The PCR products from Arabidopsis and canola were purified and used as radiolabeled hybridization probes to screen the Lambda Yes Arabidopsis cDNA library at low stringency, as described above. This led to the isolation of a pure phage, which was excised to give plasmid pYacp7. The cDNA insert in pYacp7 was partially sequenced. Its sequence showed that it encoded an incomplete desaturase polypeptide that was identical to another cDNA (in plasmid pFadx-2) isolated by low-stringency hybridization as described previously. The composite sequence derived from the partial sequences from the cDNA inserts in pFadx-2 and pYacp7 is shown in SEQ ID NO:16 and the polypeptide encoded by it in SEQ ID NO:17. As discussed previously, SEQ ID NO:17 is a putative plastid delta-15 desaturase. A full-length version of pYacp7 can be readily isolated using it as a hybridization probe.

Two additional conserved regions correspond to aminoacid residues 130 to 137 and 249 and 256 of SEQ ID NO:7 (*Brassica napus* glycerolipid desaturase delta-15). Degenerate oligomers were designed to these regions with additional nucleotides containing a restriction site for Bam H1 were added to the 5' ends of each oligonucleotide to facilitate subcloning of the PCR products. The nucleotide sequences of these oligonucleotides named F2-3 and F2-3c are shown in SEQ ID NO:18 and SEQ ID NO:19 respectively.

Mixtures of degenerate oligonucleotides F2-3 and F2-3c were used to amplify, isolate and clone glycerolipid desaturase sequences represented in corn seed mRNA population, essentially as described in the GeneAmp RNA PCR Kit purchased from Perkin Elmer Cetus and in Innis, et al., Eds, (1990) PCR Protocols: A Guide to Methods and Applications, Academic Press, San Diego.

Corn seed RNA was obtained from developing corn seeds 15–20 days after pollination by the method of Chirgwin et al., (1979) Biochemistry 18:5294. Corn seed polyadenylated mRNA was isolated by affinity chromatography on oligo-dT cellulose (Aviv et al., Proc. Natl. Acad. Sci. USA (1972) 69:1408–1411). 20–50 ng of A+mRNA were used in reverse transcription reactions with oligo-dT and random hexamers primers using the reaction buffer and conditions recomended by Perkin Elmer Cetus. The resulting cDNA was then used as template for the amplification of corn seed glycerolipid sequences using the set of degenerate primers in SEQ ID NO: 18 and 19. Reaction conditions were as described by Perkin Elmer Cetus, the amplification protocol consisted of a sequence of 95° C./1 min, 55° C./1 min, 72° C./2 min for 30–50 cycles. The resulting polymerase reaction products were phenol-chloroform extracted, digested with Bam HI and separated from unincorporated primers by gel filtration chromatopgraphy on Linker 6 spin columns (Pharmacia Inc.). The resulting PCR products were cloned into pBluescript SK at the Bam H1 site, and transformed into *E. coli* DH5 competent cells. Restriction analysis of plasmid DNA from the transformed colonies obtained revealed a colony, PCR-20, that contained an insert of about 0.5 kB in size at the pBluescript SK BamH1 site. The PCR-20 insert was completely sequenced on both strands. The nucleotide sequence of PCR20 insert is shown in SEQ ID NO:14 and the translated amino acid sequence is shown in SEQ ID NO:15. This aminoacid sequence shows an overall identity of 61.9% to the aminoacid sequence of *Brassica napus* microsomal delta-15 deaturase shown in SEQ ID NO:7. This result identifies the PCR20 insert as a polymerase reaction product of a corn seed delta-15 desaturase cDNA. PCR20 insert may be used as a probe to readily isolate full length corn seed delta-15 desaturase cDNAs or as such to antisense or cosuppress corn seed glycerolipid delta-15 desaturase gene expression in transgenic corn plants by cloning it in the appropriate corn gene expression vector.

EXAMPLE 7

Use of the *Arabidopsis thaliana* Delta-15 Desaturase Genomic Clones as a Restriction Fragment Length Polymorphism (RFLP) Markers to Map the Delta-15 Desaturase Loci in Arabidopsis DNA flanking the T-DNA insertion site in mutant line 3707 was used to map the genetic locus encoding the delta-15 desaturase of *Arabidopsis thaliana* seeds. An approximately 12 kB genomic DNA fragment containing the Arabidopsis delta-15 desaturase coding sequence was removed from the lambda-4211 clone by digestion with restriction endonuclease Xho I, separated from the Lambda arms by agarose gel electrophoresis, and purified using standard procedures. The isolated DNA was labeled with $^{32}p$ using a random priming kit from Pharmacia under conditions recommended by the manufacturer. The radioactive DNA was used to probe a Southern blot containing genomic DNA from *Arabidopsis thaliana* (ecotype Wassileskija and marker line W100 ecotype Landesberg background) digested with one of several restriction endonucleases. Following hybridization and washes under standard conditions (Sambrook et al., Molecular Cloning: A Laboratory Manual, 2nd ed. (1989) Cold Spring Harbor Laboratory Press), autoradiograms were obtained. Different patterns of hybridization (polymorphisms) were identified in digests using restriction endonucleases Bgl II, Cla I, Hind III, Nsi I, and Xba I. The same radiolabeled DNA fragment was used to map the polymorphism essentially as described by Helentjaris et al., (Theor. Appl. Genet. (1986) 72:761–769). The radiolabeled DNA fragment was applied as described above to Southern blots of Xba I digested genomic DNA isolated from 117 recombinant inbred progeny (derived from single-seed descent lines to the $F_6$ generation) resulting from a cross between *Arabidopsis thaliana* marker line W100 and ecotype Wassileskija (Burr et al., Genetics (1988) 118:519–526). The bands on the autoradiograms were interpreted as resulting from inheritance of either paternal (ecotype Wassileskija) or maternal (marker line W100) DNA or both (a heterozygote). The resulting segregation data were subjected to genetic analysis using the computer program Mapmaker (Lander et al., Genomics (1987) 1:174–181). In conjunction with previously obtained segregation data for 63 anonymous RFLP markers and 9 morphological markers in *Arabidopsis thaliana* (Chang et al., Proc. Natl. Acad. Sci.

USA (1988) 85:6856–6860; Nam et al., Plant Cell (1989) 1:699–705), a single genetic locus was positioned corresponding to the genomic DNA containing the delta-15 desaturase coding sequence. The location of the delta-15 desaturase gene was thus determined to be on chromosome 2 between the lambda AT283 and cosmid c6842 RFLP markers, near the py and erecta morphological markers.

The cDNA in plasmid pCM2 was also shown to hybridize polymorphically to genomic DNA from *Arabidopsis thaliana* (ecotype Wassileskija and marker line W100 ecotype Landesberg background) digested with Eco RI. It was used as a RFLP marker to map the genetic locus for the gene encoding this fatty acid desaturase in Arabidopsis as described above. A single genetic locus was positioned corresponding to this desaturase cDNA. Its location was thus determined to be on chromosome 3 between the lambda AT228 and cosmid c3838 RFLP markers, "north" of the glabrous locus (Chang et al., Proc. Natl. Acad. Sci. USA (1988) 85:6856–6860; Nam et al., Plant Cell (1989) 1:699–705).

EXAMPLE 8

Use of Soybean Seed Microsomal Delta -15 Glycerolipid Desaturase cDNA Sequence in Plasmid as a Restriction Fragment Length Polymorphism (RFLP) Marker A 600 bp fragment of the cDNA insert from plasmid pXF1, which contains about 300 bp of the coding sequence and 300 bp of the 3' untranslated sequence, was excised by digestion with restriction enzyme Eco RI in standard conditions as described in Sambrook et al. (Molecular Cloning, A Laboratory Manual, 2nd ed. (1989) Cold Spring Harbor Laboratory Press), purified by agarose gel electrophoresis and labeled with $^{32}$p using a Random Priming Kit from Bethesda Research Laboratories under conditions recommended by the manufacturer. The resulting radioactive probe was used to probe a Southern blot (Sambrook et al., Molecular Cloning, A Laboratory Manual, 2nd ed. (1989) Cold Spring Harbor Laboratory Press) containing genomic DNA from soybean [*Glycine max* (cultivar Bonus) and *Glycine soja* (PI81762)], digested with one of several restriction enzymes. After hybridization and washes under standard conditions (Sambrook et al. Molecular Cloning, A Laboratory Manual, 2nd ed. (1989), Cold Spring Harbor Laboratory Press), autoradiograms were obtained and different patterns of hybridization (polymorphisms) were identified in digests performed with restriction enzymes Bam HI, Eco RV and Eco RI. The same probe was then used to map the polymorphic pXF1 locus on the soybean genome, essentially as described by Helentjaris et al. (Theor. Appl. Genet. (1986) 72:761–769). Plasmid pXF1/600 bp probe was applied, as described above, to Southern blots of EcoRI, PstI, EcoRV, BamHI, or Hin DIII digested genomic DNAs isolated from 68 F2 progeny plants resulting from a *G. max* Bonus x *G. soja* PI81762 cross. The bands on the autoradiograms were interpreted as resulting from the inheritance of either paternal (Bonus) or maternal (PI81762) pattern, or both (a heterozygote). The resulting data were subjected to genetic analysis using the computer program Mapmaker (Lander et al., Genomics (1987) 1:174–181). In conjunction with previously obtained data for 436 anonymous RFLP markers in soybean (Tingey et al., J. Cell. Biochem., Supplement 14E (1990) p. 291, abstract R1533). Applicants were able to position a single genetic locus corresponding to the pXF1/600 bp probe on the soybean genetic map. This confirms that the gene for microsomal delta-15 desaturase is located on chromosome 19 in the soybean genome. This information will be useful in soybean breeding targeted towards developing lines with altered polyunsaturate levels.

EXAMPLE 9

Overexpression of Microsomal Delta-15 Fatty Acid Desaturase in Plants

Detailed procedures for DNA manipulation, such as use of restriction endonucleases and other DNA modifying enzymes, agarose gel electrophoresis, isolation of DNA from agarose gels, transformation of *E. coli* cells with plasmid DNA, and isolation and sequencing of plasmid DNA are described in Sambrook et al. (1989) Molecular cloning, A Laboratory Manual, 2nd ed. Cold Spring Harbor Laboratory Press and Ausubel et al. (1989) Current Protocols in Molecular Biology John Wiley & Sons. All restriction enzymes and modifying enzymes were obtained from Bethesda Research Laboratory, unless otherwise noted.

To test the biological effect of overexpression of the microsomal delta-15 desaturase SEQ ID NO:1, i.e., the cDNA encoding *Arabidopsis thaliana* microsomal delta-15 desaturase, was placed in the sense orientation behind either the CaMV 35S promotor, to provide constituitive expression, or behind the promotor for the gene encoding soybean a' subunit of the β-conglycinin (7S) seed storage protein, to provide embryo-specific expression. To create the chimeric gene constructs, specific expression cassettes were made to facilitate easy manipulation of the desired clones. The chimeric genes were then transformed into plant cells by *Agrobacterium tumefaciens*'s binary Ti plasmid vector system [Hoekema et al., (1983) Nature 303:179–180; Bevan (1984) Nucl. Acids Res. 12:8711–8720].

Overexpression of Arabidopsis Delta-15 Fatty Acid Desaturase in Transgenic Carrot Hairy Roots To confirm the identity of SEQ ID NO:1 (Arabidopsis microsomal delta-15 fatty acid desaturase) and to test the biological effect of its overexpression in a heterologous plant species, the constitutive chimeric gene 35S:SEQ ID NO:1 was introduced into carrot tissue by Agrobacterium. The cassette for constitutive gene expression in plasmid, pAW28, originated from pK35K which, in turn, is derived from pKNK. Plasmid pKNK is a pBR322-based vector containing a chimeric gene for plant kanamycin resistance: nopaline synthase (NOS) promoter/neomycin phosphotransferase (NPT) II coding region/3' NOS chimeric gene. Plasmid pKNK has been deposited on Jan. 7, 1987 with the American Type Culture Collection of Rockville, Md., USA under the provisions of the Budapest Treaty and bears the deposit accession number 67284. A map of this plasmid is shown in Lin, et al., Plant Physiol. (1987) 84:856–861. The NOS promoter region is a 296 bp Sau 3A-Pst I fragment corresponding to nucleotides −263 to +33, with respect to the transcription start site, of the NOS gene described by Depicker et al. (1982) J. Appl. Genet. 1:561–574. The Pst I site at the 3' end was created at the translation initiation codon of the NOS gene. The NptII coding region is a 998 bp Hind III-Bam HI fragment obtained from transposon Tn5 (Beck et al., Gene (1982) 19:327–336) by the creation of Hind III and Bam HI sites at nucleotides 1540 and 2518, respectively. The 3' NOS is a 702 bp Bam HI-Cla I fragment from nucleotides 848 to 1550 of the 3' end of the NOS gene (Depicker et al., J. Appl. Genet. (1982) 1:561–574) including its' polyadenylation region. pKNK was converted to pK35K by replacing its Eco RI-Hind III fragment containing the NOS promoter with a Eco RI-Hind III fragment containing the CaMV 35S promoter. The Eco RI-Hind III 35S promoter fragment is the same as that contained in pUC35K that has been deposited on Jan. 7, 1987 with the American Type Culture Collection under the provisions of the Budapest Treaty and bears the deposit accession number 67285. The 35S promoter fragment was prepared as follows, and as described in Odell et al., Nature (1985) 313:810–813, except that the 3' end of the fragment includes CaMV sequences to +21 with respect to the transcription start site. A 1.15 KB Bgl II segment of the CaMV genome containing the region between −941 and +208 relative to the 35S transcription start site was cloned in the Bam HI site of the plasmid pUC13. This plasmid was linearized at the Sal I site in the polylinker located 3' to the CaMV fragment and the 3' end of the fragment was shortened by digestion with nuclease Bal31. Following the addition of Hind III linkers, the plasmid DNA was recircularized. From nucleotide sequence analysis of the isolated clones, a 3' deletion fragment was selected with the Hind III linker positioned at +21. The 35S promoter fragment was isolated as an Eco RI-Hind III fragment, the Eco RI site coming from the polylinker of pUC13.

The NPTII coding region in plasmid pK35K was removed from plasmid pK35K by digestion with Hind III and Bam HI restriction enzymes. Following digestion, the ends of the DNA molecules were filled-in using Klenow enzyme. Not I linkers (New England Biolabs) were then ligated on the ends and the plasmid was recircularized to yield plasmid pK35Nt. A 1.7 kB fragment containing the 35S promotor region—Not I site—3' untranslated region from nopaline synthase was liberated from pK35Nt using restriction endonucleases Eco RI and Cla I. Following restriction digestion the ends of the DNA molecules were filled-in using Klenow enzyme after which Xho I linkers (New England Biolabs) were added. The 1.7 kB fragment, now containing Xho I sites at either end, was gel isolated and cloned into the plasmid vector pURA3 (Clonetech) at its unique Xho I site. The vector pURA3 was choosen due to the absence of a Not I restriction site, the presence of a single Xho I restriction site and because the relatively large size of the vector (pURA3) would make the isolation of the gene expression cassettes relatively easy from the final construct.

The 1.4 kB Not I fragment in plasmid pCF3 containing Arabidopsis microsomal delta-15 desaturase (SEQ ID NO:1) was isolated and ligated to pAW28 (the constituitive expression cassette) previously linearized with Not I restriction enzyme and treated with calf intestinal alkaline phosphatase (Boehringer Mannheim) to result in plasmids pAW29 and pAW30 that had SEQ ID NO:1 cloned in a sense orientation and antisense orientation, respectively, with respect to the promoter. The orientation of the cDNA relative to the promotors was established by digestion with appropriate restriction endonucleases or by sequencing across the promotor-cDNA junctions.

The chimeric genes 35S promotor/sense SEQ ID NO:1/ 3'NOS and 35S promotor/antisense SEQ ID NO:1/3'NOS were isolated as a 3 kB Xho I fragment from plasmids pAW29 and pAW30, respectively, and cloned into the binary vector pZS194b at its unique Sal I site to result in plasmids pAW31 and pAW32, respectively. The orientation of the plant selectable marker gene in pAW31 and pAW32 is the same as that of the 35S promoter as acertained by digestion with appropriate restriction endonucleases. Binary vector pZS194b contains the pBR322 origin of replication, the replication and stability regions of the Pseudomonas aeruginosa plasmid pVS1 [Itoh, et al., (1984) Plasmid 11:206–220] required for replication and maintenance of the plasmid in Agrobacterium, the bacterial NPT II gene (kanamycin resistance) from Tn5 [Berg et al., (1975) Proc. Nat'l. Acad. Sci. U.S.A. 72:3628–3632] as a selectable marker for transformed bacteria, left and right borders of the T-DNA of the Ti plasmid [Bevan et al., (1984) Nucl. Acids Res. 12:8711–8720), and, between the left and right T-DNA borders are the chimeric NOS:NPT II gene for plant kanamycin resistance, described above, as a selectable marker for transformed plant cells and the E. coli lacZ a-complementing segment [Vieria and Messing (1982) Gene 19:259–267] with unique restriction endonuclease sites for Kpn I and Sal I.

The binary vectors pAW31 and pAW32 were transformed by the freeze/thaw method [Holsters et al. (1978) Mol. Gen. Genet. 163:181–187] into Agrobacterium tumefaciens strain R1000, carrying the Ri plasmid pRiA4b from Agrobacterium rhizogenes (Moore et al., (1979) Plasmid 2:617–626] to result in transformants R1000/pAW31 and R1000/pAW32, respectively.

Carrot (Daucus carota L.) cells were transformed by co-cultivation of carrot root disks with strain R1000, R1000/pAW31, or R1000/pAW32 by the method of Petit et al., (1986) Mol. Gen. Genet. 202:388–393]. To prepare explants for inoculation, carrots purchased from the local supermarket were first scrubbed gently with water and dish detergent, then rinsed thoroughly with tap and distilled water. They were surface sterilized in a stirred solution of 50% Clorox and distilled water for 30 min and rinsed thoroughly with sterile distilled water. The carrots were peeled using an autoclaved vegetable peeler and then sliced with a scalpel blade into disks of approximately 5–10 mm thickness. The disks were placed in petri dishes, onto a medium consisting of distilled deionized water solidified with 0.7% agar, in an inverted orientation so that the cut surface nearest to the root apex of the carrot was exposed for inoculation.

Cultures of Agrobacterium strains R1000, R1000/pAW31, and R1000/pAW32 were initiated from freshly grown plates in LB broth plus the appropriate antibiotic selective agents (50 mg/L chloramphenicol for the R1000 or 50 mg/L each of chloramphenicol and kanamycin for R1000/pAW31 and R1000/pAW32) and grown at 28° C. to an optical density of around 1.0 at 600 nm. Bacterial cells were pelleted by centrifugation, rinsed and resuspended in LB broth without antibiotics. Freshly cut carrot disks were inoculated by applying 100 μL of the bacterial suspension to the cut surface of each disk. As a control, some disks were inoculated with sterile LB broth only, to indicate the extent of root formation in the absence of Agrobacterium.

Inoculated root disks were incubated at 25° C. in the dark in petri dishes sealed with Parafilm. After two weeks of co-cultivation of carrot disks with Agrobacterium, the carrot disks were transferred to fresh agar-solidified water medium containing 500 mg/L carbenicillin for the counterselection of Agrobacterium. At this time, hairy root formation was noted on some root disks. Transfer of the explants to fresh counterselection medium was done at four weeks. Excision of individual roots from the explants was begun at six weeks. Ten days later, additional roots were taken from the explants as needed.

Approximately 5–10 mm long hairy roots were excised and individually subcultured on MS minimal organics medium with 30 g/L sucrose (Gibco, Grand Island, N.Y., Cat. No. 510-1118EA) and 500 mg/L carbenicillin. Approximately equal numbers of roots were subcultured in liquid medium and in a medium solidified with 0.6% agarose. Cultures on solid medium were grown in 60×100 mm petri dishes, liquid cultures were in 6-well culture dishes. When excising roots, an effort was made to select single roots from distinct callus-like outgrowths on the wounded surface. These sites of excision were marked on the lid of the petri dish to minimize repeat sampling of tissue originating from the same transformation event.

Two to three weeks after excision from the explants, individual hairy root cultures that were not visibly contaminated with Agrobacterium were transferred to fresh MS medium supplemented with 500 mg/L carbenicillin. The root mass of each culture was cut into segments including one or more branch roots, and these segments were transferred as a group to a plate or well of fresh medium. Approximately 20 mg fresh weight of tissue of root cultures which grew to adequate size within the next two to three weeks were sampled for fatty acid composition by gas chromatography of the fatty acyl methyl esters essentially as described by Browse et al., (Anal. Biochem. (1986) 152:141–145) except that 2.5% $H_2SO_4$ in methanol was used as the methylation reagent and samples were heated for 1.5 h at 80° C. to effect the methanolysis of the seed triglycerides. The results are shown in Table 6. A second sample of tissue consisting of an actively growing root tip of approximately 1 cm was excised and placed on MS medium supplemented with 500 mg/L carbenicillin and 25–50 mg/L kanamycin to test for kanamycin resistance select for hairy roots co-transformed with the binary vector [Simpson et al. (1986) Plant Mol. Biol. 6:403–415].

TABLE 6

Percent 18:3 and 18:2/18:3 Ratio in Roots of Transgenic Carrots

| Root Sample | Transformation Vector Used | % 18:3 | % 18:2/18:3 |
|---|---|---|---|
| 1 | R1000/pAW31 | 62 | 0.09 |
| 2 | R1000/pAW31 | 8 | 7.30 |
| 3 | R1000/pAW31 | 10 | 5.69 |
| 4 | R1000/pAW31 | 62 | 0.06 |
| 5 | R1000/pAW31 | 10 | 5.07 |
| 6 | R1000/pAW31 | 4 | 14.2 |
| 7 | R1000/pAW31 | 61 | 0.18 |
| 8 | R1000/pAW31 | 4 | 15.1 |
| 9 | R1000/pAW31 | 61 | 0.07 |
| 10 | R1000/pAW31 | 63 | 0.09 |
| 11 | R1000/pAW31 | 15 | 3.04 |
| 12 | R1000/pAW31 | 64 | 0.14 |
| 13 | R1000/pAW31 | 5 | 9.94 |
| 14 | R1000/pAW31 | 9 | 6.72 |
| 15 | R1000/pAW31 | 8 | 7.08 |
| 16 | R1000/pAW31 | 8 | 6.31 |
| 17 | R1000/pAW31 | 23 | 1.86 |
| 18 | R1000/pAW31 | 8 | 7.33 |
| 19 | R1000/pAW31 | 10 | 5.99 |
| 20 | R1000/pAW31 | 7 | 8.83 |
| 21 | R1000/pAW32 | 9 | 6.80 |
| 22 | R1000/pAW32 | 4 | 11.8 |
| 23 | R1000/pAW32 | 3 | 18.8 |
| 24 | R1000/pAW32 | 10 | 6.21 |
| 25 | R1000/pAW32 | 7 | 8.57 |
| 26 | R1000/pAW32 | 3 | 16.4 |
| 27 | R1000/pAW32 | 6 | 8.29 |
| 28 | R1000/pAW32 | 5 | 9.19 |
| 29 | R1000/pAW32 | 5 | 8.47 |
| 30 | R1000/pAW32 | 8 | 7.17 |
| 31 | R1000/pAW32 | 4 | 11.9 |
| 32 | R1000/pAW32 | 8 | 7.20 |
| 33 | R1000/pAW32 | 5 | 10.4 |
| 34 | R1000/pAW32 | 8 | 7.29 |
| 35 | R1000/pAW32 | 3 | 17.2 |
| 36 | R1000/pAW32 | 8 | 7.27 |
| 37 | R1000/pAW32 | 9 | 6.01 |
| 38 | R1000/pAW32 | 9 | 6.62 |
| 40 | R1000/pAW32 | 9 | 6.02 |
| 41 | R1000 | 8 | 7.23 |
| 42 | R1000 | 8 | 7.83 |
| 43 | R1000 | 10 | 6.20 |
| 44 | R1000 | 9 | 5.97 |
| 45 | R1000 | 9 | 6.73 |
| 46 | R1000 | 9 | 6.27 |
| 47 | R1000 | 8 | 7.27 |
| 48 | R1000 | 7 | 8.30 |
| 49 | R1000 | 9 | 7.11 |

The ability of R1000 transformed "hairy" roots to grow in the absence of exogenous phytohormones can be attributed to the Ri plasmid, pRiA4b. When R1000/pAW31 or R1000/pAW32 strains are used to transform, only a fraction (about half) of the "hairy" roots will also be transformed with the experimental binary vector, pAW31 or pAW32. Thus, as expected, not all hairy roots resulting from transformation with R1000/pAW31 show the high 18:3 phenotype. The absense of any significant fatty acid phenotype in "hairy roots" transformed with R1000/pAW31 is expected, since carrot and Arabidopsis delta-15 desaturase sequences are not expected to be sufficiently related. These results show that overexpression of Arabidopsis microsomal delta-15 desaturase can result in over 10-fold increase in 18:3 at the expense of 18:2 in heterologous plant tissue.

Overexpression of Arabidopsis Delta-15 Fatty Acid Desaturase in Seeds and Complementation of the Mutation in Delta-15 Desaturation in Mutant 3707

To complement the delta-15 desaturation mutation in the T-DNA mutant 3707 and to test the biological effect of overexpression of SEQ ID NO:1 (Arabidopsis microsomal delta-15 fatty acid desaturase) in seed, the embryo-specific promoter:SEQ ID NO:1 chimeric gene was transformed into the mutant plant. This embryo-specific expression cassette in pAW42 was produced, in part, using a modified version of vector pCW109. Vector pCW109 itself was made by inserting into the Hind III site of the cloning vector pUC18 (Bethesda Research Laboratory) a 555 bp 5' non-coding region (containing the promoter region) of the β-conclycinin gene followed by the multiple cloning sequence containing the restriction endonuclease sites for Nco I, Sma I, Kpn I and Xba I, then 1174 bp of the common bean phaseolin 3' untranslated region into the Hind III site [Slightom et al., Proc. Nat'l Acad. Sci. U.S.A.(1983) 80:1897–1901]. The β-conclycinin promoter region used is an allele of the published β-conglycinin gene (Doyle et al., J. Biol. Chem. (1986) 261:9228–9238) due to differences at 27 nucleotide positions. Further sequence description may be found in Slightom (WO91/13993).

The modifications to vector pCW109 were as follows: The potential translation start site was destroyed by digestion with Nco I and Xba I restriction enzymes followed by treatment with mung bean nuclease (New England Biolabs) to create linear, blunt ended DNA molecules. After ligation of Not I linkers (New England Biolabs) and digestion with Not I restriction enzyme (New England Biolabs) the plasmid was recircularized. Confirmation of the desired change was obtained by dideoxy sequencing. The resulting plasmid was designated pAW35. The 1.8 kB Hind III fragment from pAW35 containing the modified β-conclycinin promotor/3' phaseolin region was subcloned into the Hind III site in plasmid vector pBluescript SK+ (Stratagene) creating plasmid pAW36. Plasmid pAW36 was linerized at its unique Eco RI site and ligated to Eco RI/Xho I adaptors (Stratagene). Following digestion with Xho I, the 1.7 kB Xho I fragment containing the β-conclycinin promotor/Not I site/3'-phaseolin untranslated region was cloned into the Xho I site in pURA3 vector (Clonetech). The resultant plasmid, pAW42, contains the seed specific expression cassette bordered by Xho I sites to facilitate cloning into modified T-DNA binary vectors and a unique Not I site to facilitate cloning of target cDNA sequences. Vector pURA3 was choosen due to the absence of a Not I restriction site, the presence of a single Xho I restriction site, and the relatively large size of the vector (pURA3) would make the isolation of the gene expression cassettes relatively easy from the final construct.

The 1.4 kB Not I fragment in plasmid pCF3 containing Arabidopsis microsomal delta-15 desaturase (SEQ ID NO:1) was isolated and ligated to plasmid pAW42 (the seed-specific expression cassette) that had previously been linearized with Not I restriction enzyme and treated with calf intestinal alkaline phosphatase (Boehringer Mannheim) to result in plasmids pAW45 that had SEQ ID NO:1 cloned in a sense orientation with respect to the promoter. The orientation of the cDNA relative to the promotors was established by digestion with appropriate restriction endonucleases or by sequencing across the promotor-cDNA junctions.

The chimeric β-conclycinin promotor/sense SEQ ID NO:1/phaseolin 3' was isolated as a 3.2 kB Xho I fragment from plasmid pAW45 and subcloned into the binary vector pAW25 at its unique Sal I site. In the resulting vector, pAW50, the orientation of the plant selectable marker is the same as that of the β-conclycinin promoter as acertained by digestion with appropriate restriction endonucleases. Plasmid pAW25, is derived from plasmids pZS94K and pML2. Plasmid pZS94K contains the pBR322 origin of replication, the replication and stability regions of the *Pseudomonas aeruginosa* plasmid pVS1 [Itoh, et al., (1984) Plasmid 11:206–220] required for replication and maintenance of the plasmid in Agrobacterium, the bacterial NPT II gene (kanamycin resistance) from Tn5 [Berg et al., (1975) Proc. Nat'l. Acad. Sci. U.S.A. 72:3628–3632] as a selectable marker for transformed bacteria, a T-DNA left border fragment of the octopine Ti plasmid pTiA6 and right border fragment derived from TiAch5 describe by van den Elzen et al. (Plant Mol. Biol. (1985) 5:149–154). Between these borders are the *E. coli* lacZ a-complementing segment [Vieria and Messing (1982) Gene 19:259–267] with restriction endonuclease sites Sal I and Asp 718 derived from pUC18. A 4.5 kB Asp 718-Sal I DNA fragment containing the chimeric herbicide sulfonylurea (SU)-resistant acetolactate (ALS) gene was obtained from plasmid pML2 and cloned into the Asp 718-Sal I sites of plasmid pZS94K. This chimeric ALS gene contained the CaMV 35S promoter/Cab22L Bgl II-Nco I fragment that is described by Harpster et al., [Mol. Gen. Genet. (1988) 212:182–190] and the Arabidopsis ALS coding and 3' non-coding sequences [Mazur et al., (1987) Plant Physiol. 85:1110–1117] that was mutated so that it encodes a SU-resistant form of ALS. The mutation, introduced by site-directed mutagenesis, are those present in the tobacco SU-resistant Hra gene described by Lee et al., (1988) EMBO J. 5:1241–1248. The resulting plasmid was designated pAW25.

The binary vector pAW25 containing the chimeric embryo-specific β-conglycinin promotor:sense SEQ ID NO:1 gene was transformed by the freeze/thaw method [Holsters et al., (1978) Mol. Gen. Genet. 163:181–187] into the avirulent Agrobacterium strain LBA4404/pAL4404 [Hoekema et al., (1983) Nature 303:179–180].

Arabidopsis root cultures were transformed by co-cultivation with Agrobacterium using standard aseptic techniques for the manipulation of sterile media and axenic plant/bacterial cultures were followed, including the use of a laminar flow hood for all transfers. Compositions of the culture media are listed in Table 8. Unless otherwise indicated, 25×100 mm petri plates were used for plant tissue cultures. Incubation of plant tissue cultures was at 23° C. under constant illumination with mixed fluorescent and "Gro and Sho" plant lights (General Electric) unless otherwise noted. To initiate in vitro root cultures of the T-DNA homogyzous mutant line 3707 (*Arabidopsis thaliana* (L.) Heynh, geographic race Wassilewshija) seeds of the mutant line were sterilized for 10 min in a solution of 50% Chlorox with 0.1% SDS, rinsed 3 to 5 times with sterile dH$_2$O, dried thoroughly on sterile filter paper, and then 2–3 seeds were sown in liquid B5 medium in 250 mL Belco flasks. The flasks were capped, placed on a rotary shaker at 70–80 rpm, and incubated for 3–4 weeks. Prior to inoculation with Agrobacterium, root tissues were cultured on callus induction medium (MSKig). Roots were harvested by removing the root mass from the Belco flask, placing it in a petri dish, and, using forceps, pulling small bundles of roots from the root mass and placing them on MSKig medium. Petri dishes were sealed with filter tape and incubated for four days.

Agrobacterium strain LBA4404 carrying the plasmids pAL4404 and pAW50 were grown in 5 mL of YEB broth containing 25 mg/L kanamycin and 100 mg/L rifampicin. The culture was grown for approximately 17–20 h in glass culture tubes in a New Brunswick platform shaker (225 rpm) maintained at 28° C. Pre-cultured roots were cut into 0.5 cm segments and placed in a 100 μm filter, made from a Tri-Pour beaker (VWR Scientific, San Francisco, Calif. USA) and wire mesh, which is set in a petri dish. Root segments were inoculated for several min in 30–50 mL of a 1:20 dilution of the overnight Agrobacterium culture with periodic gentle mixing. Inoculated roots were transferred to sterile filter paper to draw off most of the liquid. Small bundles of roots, consisting of several root segments, were placed on MSKig medium containing 100 μM acetosyringone (3',5'-Dimethoxy-4'-hydroxyaceto-phenone, Aldrich Chemical Co., Milwaukee, Wis., USA). Petri plates were sealed with parafilm or filter tape and incubated for 2 to 3 days.

After infection, root segments were rinsed and transferred to shoot induction medium with antibiotics. Root bundles were placed in a 100 μm filter unit (described above) and rinsed with 30–50 mL liquid MSKig medium. The filter was vigorously shaken in the solution to help remove the Agrobacterium, transferred to a clean petri dish, and rinsed again. Roots were blotted on sterile filter paper and bundles of roots were placed on MSg medium containing 500 mg/l vancomycin and either 10 or 20 ppb chlorsulfuron. Plates were sealed with filter tape and incubated for 12 to 14 days.

Green nodules and small shoot primordia were visible at about 2–3 weeks. The explants were either left intact or were broken into numerous pieces and placed on GM medium containing 200–300 mg/L vancomycin and either 10 or 20 ppb chlorsulfuron for further shoot development. Plates were either sealed with two pieces of tape or with filter tape. As they developed, individual shoots were isolated from the callus and were placed on MSRg medium containing 100 mg/L vancomycin and either 10 or 20 ppb chlorsulfuron.

Dishes were sealed as described above and incubated for seven to 10 days. Shoots were then transferred to GM medium containing 100–200 mg/L vancomycin in 25×100 petri dishes or Magenta G7 vessels. Many primary transformants (T1) which were transferred to individual containers set seed (T2).

T2 seed was harvested from selected putative transformants and sown on GM medium containing 10 ppb chlorsulfuron. Plates were sealed with filter tape, cold treated for 2 or more days at 4° C., and then incubated for 10 to 20 days at 23° C. under constant illumination as described above. Seedlings were scored as resistant (green, true leaves develop) and sensitive (no true leaves develop).

Selected chlorsulfuron resistant T2 seedlings were transplanted to soil and were grown to maturity at 23° C. daytime (16 h) 18° C. nighttime (8 h) at 65–80% relative humidity.

T2 seeds from two plants were harvested at maturity and analysed individually for fatty acid composition by gas chromatography of the fatty acyl methyl esters essentially as described by Browse et al., (Anal. Biochem. (1986) 152:141–145) except that 2.5% $H_2SO_4$ in methanol was used as the methylation reagent and samples were heated for 1.5 h at 80° C. to effect the methanolysis of the seed triglycerides. The results are shown in Table 7.

TABLE 7

Percent Fatty Acid in Seeds of Transgenic Mutant 3707

| Seed Sample | 16:0 | 18:0 | 18:1 | 18:2 | 18:3 |
|---|---|---|---|---|---|
| wildtype (6) | 6 | 4 | 14 | 30 | 19 |
| mutant 3707(6) | 6 | 4 | 14 | 44 | 3 |
| 1-1 | 10 | 4 | 22 | 9 | 55 |
| 1-2 | 11 | 6 | 22 | 14 | 48 |
| 1-3 | 12 | 7 | 16 | 6 | 57 |
| 1-4 | 10 | 4 | 30 | 52 | 4 |
| 1-5 | 10 | 4 | 18 | 17 | 48 |
| 1-6 | 10 | 5 | 15 | 15 | 53 |
| 2-1 | 11 | 5 | 19 | 60 | 4 |
| 2-2 | 10 | 5 | 19 | 9 | 56 |
| 2-3 | 9 | 4 | 27 | 8 | 52 |
| 2-4 | 10 | 5 | 17 | 10 | 56 |
| 2-5 | 10 | 5 | 19 | 9 | 56 |
| 2-6 | 10 | 5 | 17 | 17 | 48 |

The fatty acid composition of the wild-type and mutant line 3707 represents the average of 6 single seeds each. Seeds from plant 1 are designated 1-1 to 1-6 and those from plant 2 are designated 2-1 to 2-6. The 20:1 and 20:2 amounts are not shown. The data shows that the one out of six seeds in each plant show the mutant fatty acid phenotype, while the remaining seeds show more than 10-fold increase in 18:3 to ca.55%. While most of the increase occurs at the expense of 18:2, some of it also occurs at the expense of 18:1. Such high levels are of linolenic acid in vegetable oils are observed in specialty oil crops, such as linseed. Thus, overexpression of this gene in other oilscrops, especially canola, which is a close relative of Arabidopsis, is also expected to result in such high levels of 18:3.

TABLE 8

Medium Composition

| YEP MEDIUM | | BASIC MEDIUM | |
|---|---|---|---|
| Bacto Beef Extract | 5.0 g | 1 Pkg. Murashige and Skoog | |
| Bacto Yeast Extract | 1.0 g | Minimal Organics Medium without | |
| Peptone | 5.0 g | Sucrose (Gibco #510-3118 or | |
| Sucrose | 5.0 g | Sigma #M6899) | |
| $MgSO_4.7H_2O$ | 0.5 g | 10 mL Vitamin Supplement | |
| Agar (optional) | 15.0 g | 0.05% MES | 0.5 g/L |
| pH | | 0.8% agar | 8 g/L |
| | | pH | |
| VITAMIN SUPPLEMENT | | GM = Germination Medium | |
| 10 mg/L thiamine | | Basic Medium | |
| 50 mg/L pyridoxine | | 1% sucrose | 10 g/L |
| 50 mg/L nicotinic acid | | | |
| MSKIg = Callus Induction Medium | | MSg = Shoot Induction Medium | |
| Basic Medium | | Basic Medium | |
| 2% glucose | 20 g/L | 2% glucose | 20 g/L |
| 0.5 mg/L 2,4-D | 2.3 μL | 0.15 mg/L IAA | 0.86 μM |
| 0.3 mg/L Kinetin | 1.4 μM | 5.0 mg/L 2iP | 24.6 μM |
| 5 mg/L IAA | 28.5 μM | | |
| MSRg = Shoot Induction Medium | | | |
| Basic Medium | | | |
| 2% glucose | 20 g/L | | |
| 12 mg/L IBA | 58.8 μM | | |
| 0.1 mg/L Kinetin | 0.46 μM | | |

EXAMPLE 10

Construction of Vectors for Transformation of *Brassica napus* for Reduced Expression of Delta-15 Desaturases in Developing Seeds Detailed procedures for manipulation of DNA fragments by restriction endonuclease digestion, size separation by agarose gel electrophoresis, isolation of DNA fragments from agarose gels, ligation of DNA fragments, modification of cut ends of DNA fragments and transformation of *E. coli* cells with circular DNA plasmids are all described in Sambrook et al., (Molecular Cloning, A Laboratory Manual, 2nd ed (1989) Cold Spring Harbor Laboratory Press) and Ausubel et al., Current Protocols in Molecular Biology (1989) John Wiley & Sons).

Sequences of the cDNA's encoding the *B. napus* cytoplasmic delta-15 desaturase and the *Brassica napus* plastid delta-15 desaturase were placed in the antisense orientation behind the promoter region from the a' subunit of the soybean storage protein β-conglycinin to provide embryo specific expression and high expression levels.

An embryo-specific expression cassette was constructed to serve as the basis for chimeric gene constructs for anti-sense expression of the nucleotide sequences of delta-15 desaturase cDNAs. The vector pCW109 was produced by the insertion of 555 base pairs of the β-conglycinin (a' subunit of the 7s seed storage protein) promoter from soybean (*Glyine max*), the β-conglycinin 5' untranslated region followed by a multiple cloning sequence containing the restriction endonuclease sites for Nco I, Sma I, Kpn I and Xba I, then 1174 base pairs of the common bean phaseolin 3' untranslated region into the Hind III site in the cloning vector pUC18 (BRL). The β-conglycinin promoter sequence represents an allele of the published β-conglycinin gene (Doyle et al., (1986) J. Biol. Chem. 261:9228–9238) due to differences at 27 nucleotide positions. Further sequence description may be found in Slightom (WO91/13993). The sequence of the 3' untranslated region of phaseolin is described in (Slightom et al., (1983) Proc. Natl. Acad. Sci. USA, 80:1897–1901).

To facilitate use in antisense constructions, the Nco I site and potential translation start site in the plasmid pCW109 was destroyed by digestion with Nco I, mung bean exonuclease digestion and re-ligation of the blunt site to give the modified plasmid pCW109A. pCW109A was opened between the β-conglycinin promoter sequence and the phaseolin 3' sequence by digestion with Sma I to allow insertion of blunt ended cDNA fragments encoding the delta-15 desaturase sequences by ligation. The blunt ended fragment of the cytoplasmic delta-15 desaturase was obtained from plasmid pBNSF3, which contains the nucleotides 208 to 1336 of the cDNA insert described in SEQ ID NO:6. pBNSF3 was modified to remove the Hind III site at bases 682 to 687 of SEQ ID 6 by digesting with Hind III, blunting with Klenow and re-ligating. The resulting plasmid [pBNSF3(-H)], was digested with Eco RI and Xho I to release the delta-15 cDNA fragment, all ends were Klenow blunted and the 1.2 kB coding region was purified by gel isolation. The 1.2 kB fragment was ligated into the Sma I cut pCW109A described above. The antisense orientation of the inserted cDNA relative to the β-conglycinin promoter was established by digestion with Aat I which cuts in the delta-15 desaturase coding region and in the vector 5' to the β-conglycinin promoter to release a 1.4 Kb fragment when the coding region is in the antisense orientation. The antisense construction was given the name pCCFdR1.

The transcription unit [β-conglycinin promoter:antisense delta-15 desaturase:phaseolin 3'end] was released from pCCFdR1 by Hind III digestion, isolated, and ligated into pBluescript which had also been Hind III digested to give plasmid pCCFdR2. This construct has unique BamH I and Sal I sites which were digested. The 3 kB transcriptional unit was isolated and cloned into the Bam HI and Sal I sites in pZ199 described below to give the binary vector pZCC3FdR. The orientation given by this directional cloning is with transcription of both the selectable marker gene and the delta-15 antisense gene in the same direction and toward the right border tDNA sequence.

An antisense construction based on the plastid delta-15 desaturase was made with the 425 most 3' bases of SEQ ID NO:8 which is contained in the plasmid pBNSFD-8. pBNSFD-8 represents a cDNA of the plastid delta-15 desaturase in pBluescript. The cDNA insert was removed from pBNSFD-8 by digestion with Xho I and Sma I, the fragments were blunted, and the 425 base insert isolated by gel purification. The isolated fragment was cloned into the Sma I site of pCW109A and the antisense orientation of the chosen clone confirmed by digestion of the plasmid with Pst I. Pst I cuts in the plastid delta-15 sequence and in the pCW109A vector 5' to the β-conglycinin promoter to release a 1.2 kB fragment indicative of the antisense orientation. The plasmid containing this construction was called pCCdFdR1.

Digestion of pCCdFdR1 with Hind III removes a 2.3 kB fragment containing the transcriptional unit [β-conglycinin promter:plastid delta-15 antisense:3'-phaseolin sequence]. The fragment was gel isolated and cloned into Hind III digested pBluescript. The orientation of the fragment was relative to the Bam HI site in the cloning region of pBluescript was determined by digestion with Pst I as described above. A clone oriented with the promoter toward the Sal I containing end was chosen and given the name pCCdFdR2.

pCCdFdR2 was digested with Bam HI and Sal I, the released fragment was gel isolated and ligated into pZ199 which had been digested with Bam HI and Sal I to give the binary vector pZCCdFdR.

Vectors for transformation of the antisense delta-15 desaturase constructions under control of the β-conglycinin promoter into plants using *Agrobacterium tumefaciens* were produced by constructing a binary Ti plasmid vector system (Bevan, (1984) Nucl. Acids Res. 12:8711–8720). The starting vector used for these systems (pZS199) is based on a vector which contains: (1) the chimeric gene nopaline synthase/neomycin phosphotransferase as a selectable marker for transformed plant cells (Bevan et al., (1984) Nature 304:184–186), (2) the left and right borders of the T-DNA of the Ti plasmid (Bevan et al., (1984) Nucl. Acids Res. 12:8711–8720), (3) the *E. coli* lacZ a-complementing segment (Vieria and Messing (1982) Gene 19:259–267) with unique restriction endonuclease sites for Eco RI, Kpn I, Bam HI, Hin DIII, and Sal I, (4) the bacterial replication origin from the Pseudomonas plasmid pVS1 (Itoh et al., (1984) Plasmid 11:206–220), and (5) the bacterial neomycin phosphotransferase gene from Tn5 (Berg et al., (1975) Proc. Natnl. Acad. Sci. U.S.A. 72:3628–3632) as a selectable marker for transformed *A. tumefaciens*. The nopaline synthase promoter in the plant selectable marker was replaced by the 35S promoter (Odell et al. (1985) Nature, 313:810–813) by a standard restriction endonuclease digestion and ligation strategy. The 35S promoter is required for efficient *Brassica napus* transformation as described below.

EXAMPLE 11

Agrobacterium Mediated Transformation of *Brassica Napus*

The binary vectors pZCC3FdR abd pZCCdFdR were transferred by a freeze/thaw method (Holsters et al., (1978) Mol Gen Genet 163:181–187) to the Agrobacterium strain LBA4404/pAL4404 (Hoekema et al., (1983), Nature 303:179–180).

*Brassica napus* cultivar "Westar" was transformed by co-cultivation of seedling pieces with disarmed *Agrobacterium tumefaciens* strain LBA4404 carrying the the appropriate binary vector.

*B. napus* seeds were sterilized by stirring in 10% Chlorox, 0.1% SDS for thirty min, and then rinsed thoroughly with sterile distilled water. The seeds were germinated on sterile medium containing 30 mM $CaCl_2$ and 1.5% agar, and grown for six days in the dark at 24° C.

Liquid cultures of Agrobacterium for plant transformation were grown overnight at 28° C. in Minimal A medium containing 100 mg/L kanamycin. The bacterial cells are pelleted by centrifugation and resuspended at a concentration of $10^8$ cells/mL in liquid Murashige and Skoog Minimal Organic medium containing 100 μM acetosyringone.

*B. napus* seedling hypocotyls were cut into 5 mm segments which were immediately placed into the bacterial suspension. After 30 min, the hypocotyl pieces were removed from the bacterial suspension and placed onto BC-12 callus medium containing 100 μM acetosyringone. The plant tissue and Agrobacteria were co-cultivated for three days at 24° C. in dim light.

The co-cultivation was terminated by transferring the hypocotyl pieces to BC-12 callus medium containing 200 mg/L carbenicillin to kill the Agrobacteria, and 25 mg/L kanamycin to select for transformed plant cell growth. The seedling pieces were incubated on this medium for three weeks at 24° C. under continuous light.

After three weeks, the segments wre transferred to BS-48 regeneration medium containing 200 mg/L carbenicillin and 25 mg/L kanamycin. Plant tissue was subcultured every two weeks onto fresh selective regeneration medium, under the same culture conditions described for the callus medium.

Putatively transformed calli grow rapidly on regeneration medium; as calli reached a diameter of about 2 mm, they were removed from the hypocotyl pieces and placed on the same medium lacking kanamycin.

Shoots began to appear within several weeks after transfer to BS-48 regeneration medium. As soon as the shoots formed discernable stems, they were excised from the calli, transferred to MSV-1A elongation medium, and moved to a 16:8 h day/night photoperiod at 24° C.

Once shoots had elongated several internodes, they were cut above the agar surface and the cut ends were dipped in Rootone. Treated shoots were planted directly into wet Metro-Mix 350 soiless potting medium. The pots were covered with plastic bags which were removed when the plants were clearly growing—after about 10 days.

Plants were grown under a 16:8 h day/night photo-period, with a daytime temperature of 23° C. and a nighttime temperature of 17° C. When the primary flowering stem began to elongate, it was covered with a mesh pollen-containment bag to prevent outcrossing. Self-pollination was facilitated by shaking the plants several times each day. Seeds derived from self-pollinations were harvested about three months after planting.

TABLE 9

| Minimal A Bacterial Growth Medium Dissolve in distilled water: | Brassica Callus Medium BC-12 Per liter: |
|---|---|
| 10.5 g potassium phosphate, dibasic | Murashige and Skoog Minimal Organic Medium (MS salts, 100 mg/L i-inositol, 0.4 mg/L thiamine; GIBCO #510-3118) |
| 4.5 g potassium phosphate, monobasic | |
| 1.0 g ammonium sulfate | 30 sucrose |
| 0.5 g sodium citrate, dihydrate | 18 g mannitol |
| Make up to 979 mLs with distilled water | 1.0 mg/L 2,4-D |
| | 3.0 mg/L kinetin |
| Autoclave | 0.6% agarose |
| Add 20 mLs filter-sterilized 10% sucrose | pH 5.8 |
| Add 1 mL filter-sterilized 1 M $MgSO_4$ | |
| Brassica Regeneration Medium BS-48 Murashige and Skoog Minimal Organic Medium Gamborg B5 Vitamins (SIGMA #1019) | Brassica Shoot Elongation Medium MSV-1A Murashige and Skoog Minimal Organic Medium Gamborg B5 |
| 10 g glucose | Vitamins |
| 250 mg xylose | 10 g sucrose |
| 600 mg MES | 0.6% agarose |
| 0.4% agarose | pH 5.8 |
| pH 5.7 | |
| Filter-sterilize and add after autoclaving: | |
| 2.0 mg/L zeatin | |
| 0.1 mg/L IAA | |

EXAMPLE 12

Analysis of Transgenic *Brassica napus* Plants

Insertion of the intact antisense transcriptional unit was verified by Southern analysis using transgenic plant leaf tissue as the source of DNA as described in Example 5. Ten micrograms of leaf DNA was digested to completion with a mixture of Bam HI and Sal I restriction endonucleases and then separatd by agarose gel electrophoresis. The separated DNA was transferred to Hybond H+ membrane and hybridized with radiolabeled insert from pBNSF3-2. An estimate of the number of copies of the inserted transgene was made by calibrating each Southern blot with standard amounts of pBNSF3-2 corresponding to 1 and 5 copies per genome and comparing intensities of the autoradiographic signal from the standards, the endogenous delta-15 desaturase signals and the inserted gene signal. To date, 38 independent transformants have been analyzed for presence of the gene and 36 were found to be positive.

The relative content of the 5 most abundant fatty acids in canola seeds was determined either by direct trans-esterification of individual seeds in 0.5 mL of methanolic $H_2SO_4$ (2.5%) or by hexane extraction of bulk seed samples followed by trans-esterification of an aliquot in 0.8 mL of 1% sodium methoxide in methanol. Fatty acid methyl esters were extracted from the methanolic solutions into hexane after the addition of an equal volume of water.

The relative content of 18:3 fatty acid varies significantly during seed development. To a lesser extent, the ratio of 18:3 to 18:2 varies also. Thus meaningful data can be obtained only from seeds after maturation and drydown. Additionally, the ratio of 18:3 to total fatty acid content and to 18:0 varies significantly due to environmental factors, primarily temperature. In this circumstance, the most appropriate controls are the transformed plants which by Southern analysis do not contain the antisense delta-15 transgene. Analysis from the first 5 transformants to reach dry seed are given in Table 10 below. Seeds were harvested using a hand thesher, bulked and a 1.5 g (about 300 seeds) sample was taken. Seed from each transformant was crushed with a mortar and pestel, extracted 4 times with 8 mL hexane at about 50° C. The combined extracts were reduced in volume to 5 mL and two 50 microliter aliquots were taken for esterification as described above. Separation of the fatty acid methyl esters was done by gas-liquid chromatography using an Omega-wax 320 column (Supelco Inc., 0.32 mm ID×30 M) run isothermally at 220° and cycled to 260° between each injection.

TABLE 10

| Transformant No. | % 18:3 | % 18:3/18:2 | Antisense delta-15 Copy No. |
|---|---|---|---|
| pZCC3FdR-91 | 6.2 | 0.39 | 0 |
| pZCC3FdR-81 | 5.9 | 0.33 | 1 |
| pZCC3FdR-15 | 6.0 | 0.38 | 2 |
| pZCC3FdR-11 | 5.6 | 0.34 | 1 |
| pZCC3FdR-148 | 8.2 | 0.40 | 2 |

The differences between the 4 transformed lines and line 92 are very small, however to test the significance of the difference in the 18:3/18:2 ratio between line 81 and 91, 25 individual seeds from each line were transesterified and their fatty acid composition determined. The average ratio for line 81 was 0.345 with a coefficient of variation of 11.6% while the average for line 91 was 0.375 with a coefficient of variation of 8.0%. The sample means are significantly different at the 0.01% level using Student's t test.

EXAMPLE 13

Construction of Vectors for Transformation of *Glycine max* for Reduced Expression of Delta-15 Desaturases in Developing Seeds The antisense *G. max* plastid delta-15 desaturase cDNA sequence under control of the β-conglycinin promoter was constructed using the vector pCW109A described in Example 10 above. For use in the soybean transformation system described below, the transcriptional unit was placed in a vector along with an appropriate selectable marker expression system. The starting vector was pML45, which consists of the non-tissue specific and constitutive promoter designated 508D and described in Hershey (WO 9011361) driving expression of the neomycin phosphotransferase gene described in (Beck et al. (1982) Gene 19:327–336) followed by the 3' end of the nopaline synthase gene including nucleotides 848 to 1550 described by (Depicker et al. (1982) J. Appl. Genet. 1:561–574). This transcriptional unit was inserted into the commercial cloning vector pGEM9Z (BRL) and is flanked at the 5' end of the 508D promoter by the restriction sites Sal I, Xba I, Bam HI and Sma I in that order. An additional Sal I site is present at the 3' end of the NOS 3' sequence and the Xba I, Bam HI and Sal I sites are unique.

Removal of the unit [β-conglycinin promter:cloning region:phaseolin 3' end] from pCW109A by digestion with Hind III, blunting the ends and isolating the 1.8 kB fragment afforded the expression cassette pCST by ligating the above isolated fragment into the Sma I site of pML45. A clone with the β-conglycinin promoter in the same orientation as the 508D promoter were chosen by digestion with Xba I. The correct orientation releases a 700 bp fragment. This vector cassette was called pCST.

The 2.2 kB insert encoding the soybean, plastid delta-15 desaturase was subcloned from the plasmid pXF1 by digestion with HinP I to remove about 1 kB of unrelated cDNA. HinP I-cuts within the cDNA insert very near the 5' end of the cDNA for the delta-15 desaturase and about 300 bp from the 3' end of that cDNA. The Cla I compatable ends were cloned into Cla I digested pBluescript and a clone with the 5' end of the cDNA toward the Eco RV site in the pBluescript cloning region was selected based on the relaese of a 900 bp fragment by digestion with Pst I. The subcloned plasmid was called pS3Fd1.

The delta-15 encoding sequence was removed from pS3Fd1 by digestion with HinC II and Eco RV, the 2.2 kB fragment was gel isolated and cloned into the opened Sma I site in pCST1. A clone with the delta-15 sequence in the antisense orientation to the β-conglycinin promoter was selected by digestion with Xba I. The antisense construct releases a 400 bp piece and that clone was designated pCS3FdST1R.

EXAMPLE 14

Transformation of Somatic Soybean Embryo Cultures

Soybean embryogenic suspension cultures are maintained in 35 mL liquid media (SB55 or SBP6) on a rotary shaker, 150 rpm, at 28° C. with mixed florescent and incandescent lights on a 16:8 h day/night schedule. Cultures were subcultured every four weeks by inoculating approximately 35 mg of tissue into 35 mL of liquid medium.

Soybean embryogenic suspension cultures were transformed with pCS3FdST1R by the method of particle gun bombardment (see Kline et al. (1987) Nature (London) 327:70). A Du Pont Biolistic PDS1000/HE instrument (helium retrofit) was used for these transformations.

To 50 mL of a 60 mg/mL 1 mm gold particle suspension was added (in order); 5 μL DNA(1 μg/μL), 20 μL spermidine (0.1 M), and 50 μl CaCl$_2$ (2.5 M). The particle preparation was agitated for 3 min, spun in a microfuge for 10 sec and the supernatant removed. The DNA-coated particles were then washed once in 400 μL 70% ethanol and resuspended in 40 μL of anhydrous ethanol. The DNA/particle suspension was sonicated three times for 1 sec each. Five μL of the DNA-coated gold particles were then loaded on each macro carrier disk.

Approximately 300–400 mg of a four week old suspension culture was placed in an empty 60×15 mm petri dish and the residual liquid removed from the tissue with a pipette. For each transformation experiment, approximately 5–10 plates of tissue were normally bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Eleven days post bombardment, the liquid media was exchanged with fresh SB55 containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as independent transformation event. These suspensions can then be maintained as suspensions of embryos clustered in an immature developmental stage through subculture or regenerated into whole plants by maturation and germination of individual somatic embryos.

Transformed embryogenic clusters were removed from liquid culture and placed on a solid agar media (SB103) containing no hormones or antibiotics. Embryos were cultured for eight weeks at 26° C. with mixed florescent and incandescent lights on a 16:8 h day/night schedule. During this period, individual embryos were removed from the clusters and analyzed at various stages of embryo development. After eight weeks the embryos become suitable for germination.

TABLE 11

| Media: | B5 Vitamin Stock |
|---|---|
| SB55 and SBP6 Stock Solutions (g/L): | 10 g m-inositol |
|  | 100 mg nicotinic acid |
| MS Sulfate 100X Stock | 100 mg pyridoxine HCl |
| MgSO$_4$ 7H2O    37.0 | 1 g thiamine |
| MnSO$_4$ H2O     1.69 | SB55 (per Liter) |
| ZnSO$_4$ 7H2O    0.86 | 10 mL each MS stocks |
| CuSO$_4$ 5H2O    0.0025 | 1 mL B5 Vitamin stock |
| MS Halides 100X Stock | 0.8 g NH$_4$NO$_3$ |
| CaCl$_2$ 2H$_2$O   44.0 | 3.033 g KNO$_3$ |
| KI              0.083 | 1 mL 2,4-D (10 mg/mL stock) |
| CoCl$_2$ 6H$_2$O   0.00125 | 60 g sucrose |
| KH$_2$PO$_4$       17.0 | 0.667 g asparagine |
| H$_3$BO$_3$        0.62 | pH 5.7 |
| Na$_2$MoO$_4$ 2H$_2$O  0.025 | For SBP6- substitute 0.5 mL 2,4-D |
| MS FeEDTA 100X Stock | SB103 (per Liter) |
| Na$_2$EDTA       3.724 | MS Salts |
| FeCO$_4$ 7H$_2$O   2.784 | 6% maltose |
|  | 750 mg MgCl$_2$ |
|  | 0.2% Gelrite |
|  | pH 5.7 |

EXAMPLE 15

Analysis of Transgenic *Glycine max* Plants

While in the globular embryo state in liquid culture as described in Example 14, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominant seed proteins (a' subunit of β-conglycinin, Kunitz Trypsin Inhibitor III and Soybean Seed Lectin) are essentially absent. Upon transfer to hormone free media to allow differentiation to the maturing somatic embryo state as described in Example 14, triacylglycerol becomes the most abundant lipid class. As well, mRNAs for a'-subunit of β-conglycinin, Kunitz Trypsin Inhibitor III and Soybean Seed Lectin become very abundant messages in the total mRNA population. In these respects the somatic soybean embryo system behaves very similarly to maturing zygotic soybean embryos in vivo, and is therefore a good and rapid model system for analyzing the phenotypic effects of modifying the expression of genes in the fatty acid biosynthesis pathway. Similar somatic embryo culture systems have been documented and used in another oilseed crop, rapeseed (Taylor et al. (1990) Planta 181:18–26). Fatty acid analysis was performed as described in Example 12 using single embryos as the tissue source. A number of embryos from line 2872 (control tissue transformed with pCST) and lines 299,303,306 and 307 (line 2872 transformed with plasmid pCS3FdST1R) were analyzed for fatty acid content. The relative fatty-acid composition of embryos taken from tissue transformed with pCS3FdST1R was compared with control tissue, transformed with pCST. The results of this analysis are shown in Table 12.

TABLE 12

| Line | Embryo | 16:0 | 18:0 | 18:1 | 18:2 | 18:3 |
|---|---|---|---|---|---|---|
| 2872 | 1 | 17.7 | 4.1 | 11.3 | 52.8 | 14.1 |
|  | 2 | 17.3 | 4.3 | 10.9 | 49.5 | 18.0 |
|  | 3 | 16.1 | 4.1 | 13.8 | 48.2 | 17.3 |
|  | 4 | 17.5 | 3.6 | 11.7 | 52.0 | 14.1 |
|  | 5 | 16.6 | 3.9 | 12.7 | 53.7 | 12.6 |
|  | 6 | 14.8 | 3.0 | 14.7 | 55.3 | 11.1 |
|  | av | 16.7 | 3.8 | 12.5 | 51.9 | 14.5 |
| 299-1-3 | 1 | 16.5 | 4.1 | 9.7 | 61.4 | 6.3 |
| 299-15-1 | 1 | 14.7 | 3.6 | 11.9 | 61.3 | 8.4 |
|  | 2 | 16.6 | 3.7 | 12.1 | 58.6 | 8.6 |
|  | 3 | 16.7 | 4.1 | 14.9 | 53.2 | 11.1 |
|  | 4 | 15.2 | 4.0 | 9.1 | 60.2 | 11.5 |
|  | 5 | 16.0 | 4.2 | 13.9 | 55.2 | 10.7 |
|  | 6 | 15.2 | 3.5 | 9.9 | 63.4 | 8.1 |
| 303-7-1 | 1 | 14.1 | 2.2 | 10.6 | 59.4 | 13.7 |
|  | 2 | 14.0 | 2.8 | 12.5 | 59.3 | 11.4 |
| 306-4-5 | 1 | 17.5 | 4.2 | 8.1 | 62.7 | 7.4 |
|  | 2 | 15.7 | 3.3 | 9.0 | 60.5 | 11.5 |
|  | 3 | 17.1 | 3.4 | 9.3 | 60.7 | 9.5 |
|  | 4 | 15.7 | 3.8 | 9.2 | 61.2 | 9.7 |
|  | 5 | 17.7 | 3.9 | 6.5 | 58.3 | 13.6 |
|  | 6 | 16.6 | 3.4 | 10.2 | 59.2 | 10.6 |
| 306-4-8 | 1 | 16.6 | 3.9 | 15.3 | 50.7 | 11.8 |
|  | 2 | 17.8 | 3.6 | 15.7 | 50.0 | 10.8 |
|  | 3 | 16.7 | 3.3 | 11.1 | 52.0 | 14.6 |
|  | 4 | 19.0 | 4.0 | 10.3 | 53.1 | 12.3 |
|  | 5 | 19.7 | 3.5 | 9.0 | 53.6 | 13.0 |
|  | 6 | 18.0 | 2.9 | 13.1 | 52.8 | 10.9 |
| 307-1-1 | 1 | 14.4 | 3.7 | 11.2 | 64.4 | 6.3 |
|  | 2 | 15.4 | 3.4 | 7.8 | 61.0 | 11.3 |
|  | 3 | 17.2 | 2.5 | 12.0 | 57.2 | 11.1 |
| 307-1-2 | 1 | 13.4 | 3.0 | 8.4 | 55.4 | 19.9 |
|  | 2 | 16.3 | 3.1 | 6.4 | 55.7 | 18.7 |
|  | 3 | 14.0 | 3.3 | 8.8 | 58.7 | 15.2 |
|  | 4 | 15.8 | 2.5 | 9.8 | 59.7 | 12.2 |
|  | 5 | 14.6 | 3.7 | 14.9 | 51.1 | 15.7 |
|  | 6 | 14.3 | 3.9 | 11.4 | 55.5 | 14.1 |

TABLE 12-continued

| Line | Embryo | 16:0 | 18:0 | 18:1 | 18:2 | 18:3 |
|---|---|---|---|---|---|---|
| 307-1-3 | 1 | 14.8 | 3.1 | 9.4 | 60.5 | 12.2 |
|  | 2 | 18.0 | 3.0 | 5.3 | 56.2 | 15.2 |
|  | 3 | 18.0 | 3.4 | 2.5 | 58.6 | 15.4 |
| 307-1-4 | 1 | 15.0 | 2.7 | 13.8 | 61.7 | 6.9 |
|  | 2 | 15.9 | 2.7 | 9.8 | 62.0 | 9.6 |
|  | 3 | 14.6 | 3.2 | 13.4 | 61.4 | 6.7 |
| 307-1-5 | 1 | 15.9 | 3.5 | 7.6 | 61.7 | 11.2 |
|  | 2 | 14.6 | 3.5 | 10.0 | 61.3 | 10.6 |
|  | 3 | 18.7 | 2.6 | 6.8 | 53.0 | 19.0 |
| 307-1-7 | 1 | 15.3 | 3.5 | 12.5 | 60.3 | 8.5 |
|  | 2 | 16.2 | 2.2 | 13.9 | 57.1 | 10.6 |
|  | 3 | 14.9 | 3.1 | 12.2 | 58.0 | 11.8 |
| 307-1-9 | 1 | 16.4 | 2.9 | 23.2 | 47.9 | 9.6 |
|  | 2 | 19.6 | 0.0 | 20.4 | 51.3 | 8.8 |
|  | 3 | 16.8 | 3.3 | 24.6 | 49.6 | 5.7 |
| 307-1-11 | 1 | 18.1 | 3.6 | 5.7 | 52.9 | 19.7 |
|  | 2 | 14.7 | 3.7 | 9.9 | 58.7 | 13.0 |
|  | 3 | 15.1 | 3.7 | 11.3 | 55.8 | 14.1 |

The average 18:3 content of control embryos was 14.5% with a range from 11.1% to 18.0%. The average 18:3 content of transformed embryos was 11.5% with a range of 6.3% to 19.9%. Almost 80% of the transformed embryos (38/48) had an 18:3 content below that of the control mean. About 44% had an 18:3 content less than the lowest observed control value and 12.5% had an 18:3 content less than half of the control mean value (i.e., less than 7.5%). The lowest 18:3 content observed in transformed tissue was 6.3% (299-1-3, 307-1-2 #1) compared with the control low of 11.1%. In all cases in transformed tissue, a decrease in 18:3 content was reflected by an equivalent increase in 18:2 content indicating that the desaturation of 18:2 to 18:3 had been reduced. The relative content of the the other fatty acids remained unchanged.

Southern analysis for the presence of the intact, introduced antisense construction was performed, as described in Example 12 using Bam HI cut gDNA, on a number of the transformed lines listed below using groups of embryos from a single transformation event. The approximate intact antisense copy number was estimated from the number and intensity of hybridizing bands on the autoradiograms and is shown in Table 13.

TABLE 13

| Line No. | Antisense copy No. | 18:3 (low) | 18:3 (average) | 18:2/18:3 ratio |
|---|---|---|---|---|
| 2872 | 0 | 11.1 | 14.5 | 3.6 |
| 303-7/1 | 1 | 11.4 | 12.6 | 4.7 |
| 307-1/2 | 3 | 12.2 | 16.0 | 3.5 |
| 306-4/8 | 3 | 10.8 | 12.2 | 4.3 |
| 307-1/7 | 4 | 8.5 | 10.3 | 5.7 |
| 306-4/5 | 6 | 7.4 | 10.4 | 5.8 |
| 307-1/1 | 6 | 6.3 | 9.6 | 6.3 |
| 299-15/1 | 7 | 8.1 | 9.7 | 6.1 |
| 307-1/4 | 8 | 6.7 | 7.7 | 8.0 |

There was a reasonable correlation between intact antisense copy number and 18:3 content, an increase in copy number correlating with a decreased 18:3 content and a consequent increase in the 18:2/18:3 ratio. The average 18:2/18:3 ratio of line 307-1/4, which had at least 8 copies of the antisense cDNA, was more than twice that of the control.

We claim:

1. An isolated nucleic acid fragment encoding a plant plastid or microsomal delta-15 fatty acid desaturase enzyme, which catalyzes a reaction at C15–C16 of a fatty acyl chain and further wherein said isolated nucleic acid fragment hybridizes to one of the nucleotide sequences set forth in SEQ ID NOS:1, 3, 5, 7, 9, 11, and 15 under one of the following sets of conditions:

(a) hybridization in 50 mM Tris, pH 7.6, 6X SSC, 5X Denhardt's, 0.5% sodium dodecyl sulfate (SDS), 100 μg denatured calf thymus DNA at 50° C. overnight and wash with 6X SSC, 0.5% SDS at room temperature for 15 min, repeat with 2X SSC, 0.5% SDS at 45° C. for 30 min, then repeat twice with 0.2X SSC, 0.5% SDS at 50° C. for 30 min each;

(b) hybridization in 50 mM Tris, pH 7.6, 6X SSC, 5X Denhardt's, 0.5% sodium dodecyl sulfate (SDS), 100 μg denatured calf thymus DNA at 50° C. overnight and wash with 6X SSC, 0.5% SDS at room temperature for 15 min, repeat with 2X SSC, 0.5% SDS at 45° C. for 30 min, then repeat twice with 0.2X SSC, 0.5% SDS at 60° C. for 30 min each;

(c) hybridization in 50 mM Tris-HCl, pH 7.5, 1 M NaCl, 1% sodium dodecyl sulfate (SDS), 5% dextran sulfate and 0.1 mg/mL denatured salmon sperm DNA at 50° C. for eighteen hours and wash twice at room temperature with 2X SSPE, 1% SDS for 5 min, then washing for 5 min at 50° C. in 0.2X SSPE, 1% SDS;

(d) hybridization in 50 mM Tris-HCl, pH 7.5, 1 M NaCl, 1% sodium dodecyl sulfate (SDS), 5% dextran sulfate and 0.1 mg/mL denatured salmon sperm DNA at 50° C. for sixteen hours and wash twice at room temperature with 2X SSPE, 1% SDS for 5 min, then wash with fresh solution for 10 min, then wash for 5 min at 50° C. in 0.5X SSPE, 1% SDS;

(e) hybridization in 50 mM Tris, pH 7.6, 6X SSC, 5X Denhardt's, 0.5% sodium dodecyl sulfate (SDS), 100 μg denatured calf thymus DNA at 50° C. overnight and wash with 6X SSC, 0.5% SDS at room temperature for 15 min, then wash twice with 2X SSC, 0.5% SDS at 45° C. for 30 min each and then wash twice with 0.2X SSC, 0.5% SDS at 60° C. for 30 min each; or (f) hybridization in 50 mM Tris-HCl, pH 7.5, 1 M NaCl, 1% sodium dodecyl sulfate (SDS), 5% dextran sulfate and 0.1 mg/mL denatured salmon sperm DNA at 50° C. for eighteen hours and wash twice at room temperature with 2X SSPE, 1% SDS for 5 min, followed by washing for 5 min at 50° C. in 0.2X SSPE, 1% SDS.

2. An isolated nucleic acid fragment comprising a nucleic acid sequence encoding a plant plastid or microsomal enzyme which catalyzes the formation of a double bond between carbon positions 3 and 4 numbered from the methyl end of a fatty acyl chain, and further wherein the amino acid sequence comprising said enzyme contains at least one of the following amino acid sequences selected from the group consisting of FVLGHDCGHGSF, GHDCGH, HDIGTHVIHHLFP, HDIGTH, or HVIHHL.

3. An isolated nucleic acid fragment encoding a plant plastid or microsomal enzyme which catalyzes the formation of a double bond between carbon positions 3 and 4 numbered from the methyl end of a fatty acyl chain, wherein said isolated nucleic acid fragment encodes a protein comprising any one of the amino acid sequences set forth in SEQ ID NOS:2, 5, 7, 9, 11, 12, 15 or 17.

4. An isolated nucleic acid fragment encoding an enzyme which catalyzes a reaction at C15–C16 of a fatty acyl chain wherein said isolated nucleic acid fragment hybridizes to the isolated nucleic acid fragment of claim 3 under one of the following sets of conditions:

(a) hybridization in 50 mM Tris, pH 7.6, 6X SSC, 5X Denhardt's, 0.5% sodium dodecyl sulfate (SDS), 100 μg denatured calf thymus DNA at 50° C. overnight and wash with 6X SSC, 0.5% SDS at room temperature for 15 min, repeat with 2X SSC, 0.5% SDS at 45° C. for 30 min, then repeat twice with 0.2X SSC, 0.5% SDS at 50° C. for 30 min each;

(b) hybridization in 50 mM Tris, pH 7.6, 6X SSC, 5X Denhardt's, 0.5% sodium dodecyl sulfate (SDS), 100 μg denatured calf thymus DNA at 50° C. overnight and wash with 6X SSC, 0.5% SDS at room temperature for 15 min, repeat with 2X SSC, 0.5% SDS at 45° C. for 30 min, then repeat twice with 0.2X SSC, 0.5% SDS at 60° C. for 30 min each;

(c) hybridization in 50 mM Tris-HCl, pH 7.5, 1 M NaCl, 1% sodium dodecyl sulfate (SDS), 5% dextran sulfate and 0.1 mg/mL denatured salmon sperm DNA at 50° C. for eighteen hours and wash twice at room temperature with 2X SSPE, 1% SDS for 5 min, then washing for 5 min at 50° C. in 0.2X SSPE, 1% SDS;

(d) hybridization in 50 mM Tris-HCl, pH 7.5, 1 M NaCl, 1% sodium dodecyl sulfate (SDS), 5% dextran sulfate and 0.1 mg/mL denatured salmon sperm DNA at 50° C. for sixteen hours and wash twice at room temperature with 2X SSPE, 1% SDS for 5 min, then wash with fresh solution for 10 min, then wash for 5 min at 50° C. in 0.5X SSPE, 1% SDS;

(e) hybridization in 50 mM Tris, pH 7.6, 6X SSC, 5X Denhardt's, 0.5% sodium dodecyl sulfate (SDS), 100 μg denatured calf thymus DNA at 50° C. overnight and wash with 6X SSC, 0.5% SDS at room temperature for 15 min, then wash twice with 2X SSC, 0.5% SDS at 45° C. for 30 min each and then wash twice with 0.2X SSC, 0.5% SDS at 60° C. for 30 min each; or (f) hybridization in 50 mM Tris-HCl, pH 7.5, 1 M NaCl, 1% sodium dodecyl sulfate (SDS), 5% dextran sulfate and 0.1 mg/mL denatured salmon sperm DNA at 50° C. for eighteen hours and wash twice at room temperature with 2X SSPE, 1% SDS for 5 min, followed by washing for 5 min at 50° C. in 0.2X SSPE, 1% SDS.

5. An isolated nucleic acid fragment of claim 1, claim 2, claim claim 3 or claim 4 wherein said fragment is isolated from a plant selected from the group consisting of soybean, oilseed Brassica species, *Arabidopsis thaliana* and corn.

6. A chimeric gene capable of causing altered levels of linolenic acid in a transformed plant cell, the gene comprising a nucleic acid fragment of any of claims 1, claim 2, claim 3 or claim 4 the fragment operably linked to suitable regulatory sequences.

7. Plants containing the chimeric gene of claim 6.

8. A method of producing seed oil containing altered levels of linolenic (18:3) acid comprising:
(a) transforming a plant cell of an oil-producing species with a chimeric gene of claim 5;
(b) growing fertile plants from the transformed plant cells of step (a);
(c) screening progeny seeds from the fertile plants of step (b) for the desired levels of linolenic (18:3) acid; and
(d) processing the progeny seed of step (c) to obtain seed oil containing altered levels of linolenic (18:3) acid.

9. A method of claim 8 wherein said plant cell of an oil-producing species is selected from the group consisting of *Arabidopsis thaliana*, soybean, oilseed *Brassica napus*, sunflower, cotton, peanut, and corn.

10. The isolated genomic DNA of *Arabidopsis thaliana* comprising the microsomal delta-15 desaturase identified by accession number ATCC 75167.

11. A plasmid designated pXF1 and bearing accession number ATCC 68874 comprising the DNA sequence of SEQ ID NO:10 which encodes a soybean delta-15 desaturase enzyme.

12. A plasmid designated pBNSF3 and bearing accession number ATCC 68854 comprising the DNA sequence of SEQ ID NO:6 which encodes an oilseed Brassica species delta-15 desaturase enzyme.

13. An isolated Polymerase Chain Reaction Product designated PCR20 comprising the DNA sequence of SEQ ID NO:14 which encodes a portion of the *Zea mays* delta-15 desaturase enzyme.

14. The method of claim 8 wherein said plant cell of an oil-producing species is selected from the group consisting of *Arabidopsis thaliana*, soybean, oilseed *Brassica napus*, sunflower, cotton and corn.

* * * * *

UNITED STATES PATENT AND TRADEMARK OFFICE
CERTIFICATE OF CORRECTION

PATENT NO. : 5,952,544
DATED : September 14, 1999
INVENTOR(S) : John Browse et al.

It is certified that error appears in the above-identified patent and that said Letters Patent is hereby corrected as shown below:

Claim 1, column 109,
Line 36, change "SEQ ID NOS: 1, 3, 5, 7, 9, 11 and 15" to -- SEQ ID NOS. 1, 3, 4, 6, 8, 10, 12, 14 and 16 --.

Claim 3, column 110,
Line 57, change "SEQ ID NOS: 2, 5, 7, 9, 11, 12, 15 or 17 to -- SEQ ID NOS: 2, 5, 7, 9, 11, 13, 15 or 17 --.

Signed and Sealed this

Ninth Day of October, 2001

Attest:

*Nicholas P. Godici*

NICHOLAS P. GODICI
*Attesting Officer*  *Acting Director of the United States Patent and Trademark Office*

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
       (A) LENGTH: 1350 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (vi) ORIGINAL SOURCE:
       (A) ORGANISM: Arabidopsis thaliana (vii) IMMEDIATE SOURCE:
       (B) CLONE: pCF3

(ix) FEATURE:
       (A) NAME/KEY: CDS
       (B) LOCATION: 46..1206

(xi) SEQUENCE DESCRIPTION: SEQ ID NO:1:

```
CTCTCTCTCT CTCTCTTCTC TCTTTCTCTC CCCCTCTCTC CGGCG ATG GTT GTT          54
                                                  Met Val Val
                                                    1

GCT ATG GAC CAA CGC ACC AAT GTG AAC GGA GAT CCC GGC GCC GGA GAC       102
Ala Met Asp Gln Arg Thr Asn Val Asn Gly Asp Pro Gly Ala Gly Asp
    5                  10                  15

CGG AAG AAA GAA GAA AGG TTT GAT CCG AGT GCA CAA CCA CCG TTC AAG       150
Arg Lys Lys Glu Glu Arg Phe Asp Pro Ser Ala Gln Pro Pro Phe Lys
 20                 25                  30                  35

ATC GGA GAT ATA AGG GCG GCG ATT CCT AAG CAC TGT TGG GTT AAG AGT       198
Ile Gly Asp Ile Arg Ala Ala Ile Pro Lys His Cys Trp Val Lys Ser
                40                  45                  50

CCT TTG AGA TCA ATG AGT TAC GTC GTC AGA GAC ATT ATC GCC GTC GCG       246
Pro Leu Arg Ser Met Ser Tyr Val Val Arg Asp Ile Ile Ala Val Ala
            55                  60                  65

GCT TTG GCC ATC GCT GCC GTG TAT GTT GAT AGC TGG TTC CTT TGG CCT       294
Ala Leu Ala Ile Ala Ala Val Tyr Val Asp Ser Trp Phe Leu Trp Pro
        70                  75                  80

CTT TAT TGG GCC GCC CAA GGA ACA CTT TTC TGG GCC ATC TTT GTT CTC       342
Leu Tyr Trp Ala Ala Gln Gly Thr Leu Phe Trp Ala Ile Phe Val Leu
    85                  90                  95

GGC CAC GAC TGT GGA CAT GGG AGT TTC TCA GAC ATT CCT CTA CTG AAT       390
Gly His Asp Cys Gly His Gly Ser Phe Ser Asp Ile Pro Leu Leu Asn
100                 105                 110                 115

AGT GTG GTT GGT CAC ATT CTT CAT TCT TTC ATC CTC GTT CCT TAC CAT       438
Ser Val Val Gly His Ile Leu His Ser Phe Ile Leu Val Pro Tyr His
                120                 125                 130

GGT TGG AGA ATA AGC CAC CGG ACA CAC CAC CAG AAC CAT GGC CAT GTT       486
Gly Trp Arg Ile Ser His Arg Thr His His Gln Asn His Gly His Val
            135                 140                 145

GAA AAC GAC GAG TCA TGG GTT CCG TTA CCA GAA AGG GTG TAC AAG AAA       534
Glu Asn Asp Glu Ser Trp Val Pro Leu Pro Glu Arg Val Tyr Lys Lys
        150                 155                 160

TTG CCC CAC AGT ACT CGG ATG CTC AGA TAC ACT GTC CCT CTC CCC ATG       582
Leu Pro His Ser Thr Arg Met Leu Arg Tyr Thr Val Pro Leu Pro Met
    165                 170                 175
```

```
CTC GCA TAT CCT CTC TAT TTG TGC TAC AGA AGT CCT GGA AAA GAA GGA      630
Leu Ala Tyr Pro Leu Tyr Leu Cys Tyr Arg Ser Pro Gly Lys Glu Gly
180                 185                 190                 195

TCA CAT TTT AAC CCA TAC AGT AGT TTA TTT GCT CCA AGC GAG AGA AAG      678
Ser His Phe Asn Pro Tyr Ser Ser Leu Phe Ala Pro Ser Glu Arg Lys
                200                 205                 210

CTT ATT GCA ACT TCA ACT ACT TGT TGG TCC ATA ATG TTC GTC AGT CTT      726
Leu Ile Ala Thr Ser Thr Thr Cys Trp Ser Ile Met Phe Val Ser Leu
            215                 220                 225

ATC GCT CTA TCT TTC GTC TTC GGT CCA CTC GCG GTT CTT AAA GTC TAC      774
Ile Ala Leu Ser Phe Val Phe Gly Pro Leu Ala Val Leu Lys Val Tyr
        230                 235                 240

GGT GTA CCG TAC ATT ATC TTT GTG ATG TGG TTG GAT GCT GTC ACG TAT      822
Gly Val Pro Tyr Ile Ile Phe Val Met Trp Leu Asp Ala Val Thr Tyr
    245                 250                 255

TTG CAT CAT CAT GGT CAC GAT GAG AAG TTG CCT TGG TAT AGA GGC AAG      870
Leu His His His Gly His Asp Glu Lys Leu Pro Trp Tyr Arg Gly Lys
260                 265                 270                 275

GAA TGG AGT TAT CTA CGT GGA GGA TTA ACA ACA ATT GAT AGA GAT TAC      918
Glu Trp Ser Tyr Leu Arg Gly Gly Leu Thr Thr Ile Asp Arg Asp Tyr
                280                 285                 290

GGA ATC TTT AAC AAC ATT CAT CAC GAC ATT GGA ACT CAC GTG ATC CAT      966
Gly Ile Phe Asn Asn Ile His His Asp Ile Gly Thr His Val Ile His
            295                 300                 305

CAT CTC TTC CCA CAA ATC CCT CAC TAT CAC TTG GTC GAC GCC ACG AAA     1014
His Leu Phe Pro Gln Ile Pro His Tyr His Leu Val Asp Ala Thr Lys
        310                 315                 320

GCA GCT AAA CAT GTG TTG GGA AGA TAC TAC AGA GAA CCA AAG ACG TCA     1062
Ala Ala Lys His Val Leu Gly Arg Tyr Tyr Arg Glu Pro Lys Thr Ser
    325                 330                 335

GGA GCA ATA CCG ATC CAC TTG GTG GAG AGT TTG GTC GCA AGT ATT AAG     1110
Gly Ala Ile Pro Ile His Leu Val Glu Ser Leu Val Ala Ser Ile Lys
340                 345                 350                 355

AAA GAT CAT TAC GTC AGC GAC ACT GGT GAT ATT GTC TTC TAC GAG ACA     1158
Lys Asp His Tyr Val Ser Asp Thr Gly Asp Ile Val Phe Tyr Glu Thr
                360                 365                 370

GAT CCA GAT CTC TAC GTT TAC GCT TCT GAC AAA TCT AAA ATC AAT         1213
Asp Pro Asp Leu Tyr Val Tyr Ala Ser Asp Lys Ser Lys Ile Asn
            375                 380                 385

TAATCTCCAT

TTGTTTAGCT CTATTAGGAA TAAACCAGCC CACTTTTAAA ATTTTTATTT CTTGTTGTTT   1273

TTAAGTTAAA AGTGTACTCG TGAAACTCTT TTTTTTTTCT TTTTTTTAT TAATGTATTT    1333

ACATTACAAG GCGTAAA                                                  1350

(2) INFORMATION FOR SEQ ID NO:2:

(i) SEQUENCE CHARACTERISTICS:
        (A) LENGTH:  386 amino acids
        (B) TYPE:  amino acid
        (D) TOPOLOGY:  linear (ii) MOLECULE TYPE:  protein (xi) SEQUENCE DESCRIPTION: SEQ ID NO:2:

Met Val Val Ala Met Asp Gln Arg Thr Asn Val Asn Gly Asp Pro Gly
1               5                   10                  15

Ala Gly Asp Arg Lys Lys Glu Glu Arg Phe Asp Pro Ser Ala Gln Pro
            20                  25                  30

Pro Phe Lys Ile Gly Asp Ile Arg Ala Ala Ile Pro Lys His Cys Trp
        35                  40                  45
```

Val Lys Ser Pro Leu Arg Ser Met Ser Tyr Val Val Arg Asp Ile Ile
 50                  55                  60

Ala Val Ala Ala Leu Ala Ile Ala Ala Val Tyr Val Asp Ser Trp Phe
 65                  70                  75                  80

Leu Trp Pro Leu Tyr Trp Ala Ala Gln Gly Thr Leu Phe Trp Ala Ile
                 85                  90                  95

Phe Val Leu Gly His Asp Cys Gly His Gly Ser Phe Ser Asp Ile Pro
                100                 105                 110

Leu Leu Asn Ser Val Val Gly His Ile Leu His Ser Phe Ile Leu Val
             115                 120                 125

Pro Tyr His Gly Trp Arg Ile Ser His Arg Thr His His Gln Asn His
         130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
        195                 200                 205

Glu Arg Lys Leu Ile Ala Thr Ser Thr Thr Cys Trp Ser Ile Met Phe
    210                 215                 220

Val Ser Leu Ile Ala Leu Ser Phe Val Phe Gly Pro Leu Ala Val Leu
225                 230                 235                 240

Lys Val Tyr Gly Val Pro Tyr Ile Ile Phe Val Met Trp Leu Asp Ala
                245                 250                 255

Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
        275                 280                 285

Arg Asp Tyr Gly Ile Phe Asn Asn Ile His His Asp Ile Gly Thr His
    290                 295                 300

Val Ile His His Leu Phe Pro Gln Ile Pro His Tyr His Leu Val Asp
305                 310                 315                 320

Ala Thr Lys Ala Ala Lys His Val Leu Gly Arg Tyr Tyr Arg Glu Pro
                325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
        355                 360                 365

Tyr Glu Thr Asp Pro Asp Leu Tyr Val Tyr Ala Ser Asp Lys Ser Lys
370                 375                 380

Ile Asn
385

(2) INFORMATION FOR SEQ ID NO:3:

(i) SEQUENCE CHARACTERISTICS:
        (A) LENGTH: 255 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Arabidopsis thaliana (vii) IMMEDIATE SOURCE:
        (B) CLONE: pF1

(ix) FEATURE:
        (A) NAME/KEY: exon
        (B) LOCATION: 68..255

(xi) SEQUENCE DESCRIPTION: SEQ ID NO:3:

```
AAATTCATCA AACCCTTTCT TCACCACATT ATTTTCACTG AGCGCATAAC ATTTTTGAGA      60

CAAGAGACTC TCTCTCTCTC TCTTCTCTCT TTCTCTCCCC CTCTCTCCGG CGATGGTTGT     120

TGCTATGGAC CAACGCACCA ATGTGAACGG AGATCCCGGC GCCGGAGACC GGAAGAAAGA     180

AGAAAGGTTT GATCCGAGTG CACAACCACC GTTCAAGATC GGAGATATAA GGGCGGCGAT     240

TCCTAAGCAC TGTTG                                                      255
```

(2) INFORMATION FOR SEQ ID NO:4:

(i) SEQUENCE CHARACTERISTICS:
        (A) LENGTH: 1525 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Arabidopsis thaliana (vii) IMMEDIATE SOURCE:
        (B) CLONE: pACF2-2

(ix) FEATURE:
        (A) NAME/KEY: CDS
        (B) LOCATION: 10..1350

(xi) SEQUENCE DESCRIPTION: SEQ ID NO:4:

```
CAAGTTCTA ATG GCG AAC TTG GTC TTA TCA GAA TGT GGT ATA CGA CCT          48
          Met Ala Asn Leu Val Leu Ser Glu Cys Gly Ile Arg Pro
            1               5                  10

CTC CCC AGA ATC TAC ACA ACA CCC AGA TCC AAT TTC CTC TCC AAC AAC        96
Leu Pro Arg Ile Tyr Thr Thr Pro Arg Ser Asn Phe Leu Ser Asn Asn
 15                  20                  25

AAC AAA TTC AGA CCA TCA CTT TCT TCT TCT TCT TAC AAA ACA TCA TCA       144
Asn Lys Phe Arg Pro Ser Leu Ser Ser Ser Ser Tyr Lys Thr Ser Ser
 30                  35                  40                  45

TCT CCT CTG TCT TTT GGT CTG AAT TCA CGA GAT GGG TTC ACG AGG AAT       192
Ser Pro Leu Ser Phe Gly Leu Asn Ser Arg Asp Gly Phe Thr Arg Asn
                 50                  55                  60

TGG GCG TTG AAT GTG AGC ACA CCA TTA ACG ACA CCA ATA TTT GAG GAG       240
Trp Ala Leu Asn Val Ser Thr Pro Leu Thr Thr Pro Ile Phe Glu Glu
         65                  70                  75

TCT CCA TTG GAG GAA GAT AAT AAA CAG AGA TTC GAT CCA GGT GCG CCT       288
Ser Pro Leu Glu Glu Asp Asn Lys Gln Arg Phe Asp Pro Gly Ala Pro
     80                  85                  90

CCT CCG TTC AAT TTA GCT GAT ATT AGA GCA GCT ATA CCT AAG CAT TGT       336
Pro Pro Phe Asn Leu Ala Asp Ile Arg Ala Ala Ile Pro Lys His Cys
 95                 100                 105

TGG GTT AAG AAT CCA TGG AAG TCT TTG AGT TAT GTC GTC AGA GAC GTC       384
Trp Val Lys Asn Pro Trp Lys Ser Leu Ser Tyr Val Val Arg Asp Val
110                 115                 120                 125
```

-continued

| | |
|---|---|
| GCT ATC GTC TTT GCA TTG GCT GCT GGA GCT GCT TAC CTC AAC AAT TGG<br>Ala Ile Val Phe Ala Leu Ala Ala Gly Ala Ala Tyr Leu Asn Asn Trp<br>               130               135               140 | 432 |
| ATT GTT TGG CCT CTC TAT TGG CTC GCT CAA GGA ACC ATG TTT TGG GCT<br>Ile Val Trp Pro Leu Tyr Trp Leu Ala Gln Gly Thr Met Phe Trp Ala<br>         145                150               155 | 480 |
| CTC TTT GTT CTT GGT CAT GAC TGT GGA CAT GGT AGT TTC TCA AAT GAT<br>Leu Phe Val Leu Gly His Asp Cys Gly His Gly Ser Phe Ser Asn Asp<br>         160                165               170 | 528 |
| CCG AAG TTG AAC AGT GTG GTC GGT CAT CTT CTT CAT TCC TCA ATT CTG<br>Pro Lys Leu Asn Ser Val Val Gly His Leu Leu His Ser Ser Ile Leu<br>175                 180               185 | 576 |
| GTC CCA TAC CAT GGC TGG AGA ATT AGT CAC AGA ACT CAC CAC CAG AAC<br>Val Pro Tyr His Gly Trp Arg Ile Ser His Arg Thr His His Gln Asn<br>190                 195              200               205 | 624 |
| CAT GGA CAT GTT GAG AAT GAC GAA TCT TGG CAT CCT ATG TCT GAG AAA<br>His Gly His Val Glu Asn Asp Glu Ser Trp His Pro Met Ser Glu Lys<br>                 210               215               220 | 672 |
| ATC TAC AAT ACT TTG GAC AAG CCG ACT AGA TTC TTT AGA TTT ACA CTG<br>Ile Tyr Asn Thr Leu Asp Lys Pro Thr Arg Phe Phe Arg Phe Thr Leu<br>         225                230               235 | 720 |
| CCT CTC GTG ATG CTT GCA TAC CCT TTC TAC TTG TGG GCT CGA AGT CCG<br>Pro Leu Val Met Leu Ala Tyr Pro Phe Tyr Leu Trp Ala Arg Ser Pro<br>             240               245               250 | 768 |
| GGG AAA AAG GGT TCT CAT TAC CAT CCA GAC AGT GAC TTG TTC CTC CCT<br>Gly Lys Lys Gly Ser His Tyr His Pro Asp Ser Asp Leu Phe Leu Pro<br>         255                260               265 | 816 |
| AAA GAG AGA AAG GAT GTC CTC ACT TCT ACT GCT TGT TGG ACT GCA ATG<br>Lys Glu Arg Lys Asp Val Leu Thr Ser Thr Ala Cys Trp Thr Ala Met<br>270                 275               280               285 | 864 |
| GCT GCT CTG CTT GTT TGT CTC AAC TTC ACA ATC GGT CCA ATT CAA ATG<br>Ala Ala Leu Leu Val Cys Leu Asn Phe Thr Ile Gly Pro Ile Gln Met<br>             290               295               300 | 912 |
| CTC AAA CTT TAT GGA ATT CCT TAC TGG ATA AAT GTA ATG TGG TTG GAC<br>Leu Lys Leu Tyr Gly Ile Pro Tyr Trp Ile Asn Val Met Trp Leu Asp<br>         305                310               315 | 960 |
| TTT GTG ACT TAC CTG CAT CAC CAT GGT CAT GAA GAT AAG CTT CCT TGG<br>Phe Val Thr Tyr Leu His His His Gly His Glu Asp Lys Leu Pro Trp<br>             320               325               330 | 1008 |
| TAC CGT GGC AAG GAG TGG AGT TAC CTG AGA GGA GGA CTT ACA ACA TTG<br>Tyr Arg Gly Lys Glu Trp Ser Tyr Leu Arg Gly Gly Leu Thr Thr Leu<br>         335                340               345 | 1056 |
| GAT CGT GAC TAC GGA TTG ATC AAT AAC ATC CAT CAT GAT ATT GGA ACT<br>Asp Arg Asp Tyr Gly Leu Ile Asn Asn Ile His His Asp Ile Gly Thr<br>350                 355               360               365 | 1104 |
| CAT GTG ATA CAT CAT CTT TTC CCG CAG ATC CCA CAT TAT CAT CTA GTA<br>His Val Ile His His Leu Phe Pro Gln Ile Pro His Tyr His Leu Val<br>             370               375               380 | 1152 |
| GAA GCA ACA GAA GCA GCT AAA CCA GTA TTA GGG AAG TAT TAC AGG GAG<br>Glu Ala Thr Glu Ala Ala Lys Pro Val Leu Gly Lys Tyr Tyr Arg Glu<br>                 385               390               395 | 1200 |
| CCT GAT AAG TCT GGA CCG TTG CCA TTA CAT TTA CTG GAA ATT CTA GCG<br>Pro Asp Lys Ser Gly Pro Leu Pro Leu His Leu Leu Glu Ile Leu Al<br>             400               405               410 | 1248 |
| AAA AGT ATA AAA GAA GAT CAT TAC GTG AGC GAC GAA GGA GAA GTT GTA<br>Lys Ser Ile Lys Glu Asp His Tyr Val Ser Asp Glu Gly Glu Val Val<br>         415                420               425 | 1296 |
| TAC TAT AAA GCA GAT CCA AAT CTC TAT GGA GAG GTC AAA GTA AGA GCA<br>Tyr Tyr Lys Ala Asp Pro Asn Leu Tyr Gly Glu Val Lys Val Arg Ala<br>430                 435               440               445 | 1344 |

```
GAT TGAAATGAAG CAGGCTTGAG ATTGAAGTTT TTTCTATTTC AGACCAGCTG      1397
Asp

ATTTTTTGCT TACTGTATCA ATTTATTGTG TCACCCACCA GAGAGTTAGT ATCTCTGAAT  1457

ACGATCGATC AGATGGAAAC AACAAATTTG TTTGCGATAC TGAAGCTATA TATACCATAC  1517

ATTGCATT                                                          1525
```

(2) INFORMATION FOR SEQ ID NO:5:

(i) SEQUENCE CHARACTERISTICS:
        (A) LENGTH: 446 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ala Asn Leu Val Leu Ser Glu Cys Gly Ile Arg Pro Leu Pro Arg
 1               5                  10                  15

Ile Tyr Thr Thr Pro Arg Ser Asn Phe Leu Ser Asn Asn Lys Phe
             20                  25                  30

Arg Pro Ser Leu Ser Ser Ser Tyr Lys Thr Ser Ser Ser Pro Leu
         35                  40                  45

Ser Phe Gly Leu Asn Ser Arg Asp Gly Phe Thr Arg Asn Trp Ala Leu
 50                  55                  60

Asn Val Ser Thr Pro Leu Thr Thr Pro Ile Phe Glu Glu Ser Pro Leu
65                  70                  75                  80

Glu Glu Asp Asn Lys Gln Arg Phe Asp Pro Gly Ala Pro Pro Phe
                 85                  90                  95

Asn Leu Ala Asp Ile Arg Ala Ala Ile Pro Lys His Cys Trp Val Lys
                100                 105                 110

Asn Pro Trp Lys Ser Leu Ser Tyr Val Val Arg Asp Val Ala Ile Val
            115                 120                 125

Phe Ala Leu Ala Ala Gly Ala Ala Tyr Leu Asn Asn Trp Ile Val Trp
130                 135                 140

Pro Leu Tyr Trp Leu Ala Gln Gly Thr Met Phe Trp Ala Leu Phe Val
145                 150                 155                 160

Leu Gly His Asp Cys Gly His Gly Ser Phe Ser Asn Asp Pro Lys Leu
                165                 170                 175

Asn Ser Val Val Gly His Leu Leu His Ser Ser Ile Leu Val Pro Tyr
            180                 185                 190

His Gly Trp Arg Ile Ser His Arg Thr His His Gln Asn His Gly His
        195                 200                 205

Val Glu Asn Asp Glu Ser Trp His Pro Met Ser Glu Lys Ile Tyr Asn
    210                 215                 220

Thr Leu Asp Lys Pro Thr Arg Phe Phe Arg Phe Thr Leu Pro Leu Val
225                 230                 235                 240

Met Leu Ala Tyr Pro Phe Tyr Leu Trp Ala Arg Ser Pro Gly Lys Lys
                245                 250                 255

Gly Ser His Tyr His Pro Asp Ser Asp Leu Phe Leu Pro Lys Glu Arg
            260                 265                 270

Lys Asp Val Leu Thr Ser Thr Ala Cys Trp Thr Ala Met Ala Ala Leu
        275                 280                 285

Leu Val Cys Leu Asn Phe Thr Ile Gly Pro Ile Gln Met Leu Lys Leu
    290                 295                 300

Tyr Gly Ile Pro Tyr Trp Ile Asn Val Met Trp Leu Asp Phe Val Thr
305                 310                 315                 320
```

```
Tyr Leu His His Gly His Glu Asp Lys Leu Pro Trp Tyr Arg Gly
            325                 330                 335

Lys Glu Trp Ser Tyr Leu Arg Gly Gly Leu Thr Thr Leu Asp Arg Asp
            340                 345                 350

Tyr Gly Leu Ile Asn Asn Ile His His Asp Ile Gly Thr His Val Ile
            355                 360                 365

His His Leu Phe Pro Gln Ile Pro His Tyr His Leu Val Glu Ala Thr
            370                 375                 380

Glu Ala Ala Lys Pro Val Leu Gly Lys Tyr Tyr Arg Glu Pro Asp Lys
385                 390                 395                 400

Ser Gly Pro Leu Pro Leu His Leu Leu Glu Ile Leu Ala Lys Ser Ile
            405                 410                 415

Lys Glu Asp His Tyr Val Ser Asp Glu Gly Val Val Tyr Tyr Lys
            420                 425                 430

Ala Asp Pro Asn Leu Tyr Gly Val Lys Val Arg Ala Asp
            435                 440                 445

(2) INFORMATION FOR SEQ ID NO:6:

(i) SEQUENCE CHARACTERISTICS:
        (A) LENGTH: 1429 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Brassica napus (vii) IMMEDIATE SOURCE:
        (B) CLONE: pBNSF3-f2

(ix) FEATURE:
        (A) NAME/KEY: CDS
        (B) LOCATION: 79..1212

(xi) SEQUENCE DESCRIPTION: SEQ ID NO:6:

TTCAAATTCA GACAATCCCC TTCTTCTCCC CGGTTTCGTC TGAACTCTCG AAACTGGGCG         60

TTGAATGTAA CCACACCT CTA ACA GTC GAC TCC TCA TCA TCT CCT CCA ATC         111
                    Leu Thr Val Asp Ser Ser Ser Ser Pro Pro Ile
                     1               5                  10

GAG GAA GAA CCC AAA ACG CAG AGA TTC GAC CCA GGC GCT CCT CCT CCG         159
Glu Glu Glu Pro Lys Thr Gln Arg Phe Asp Pro Gly Ala Pro Pro Pro
                15                  20                  25

TTC AAC CTA GCT GAC ATC AGA GCG GCG ATA CCT AAG CAT TGC TGG GTT         207
Phe Asn Leu Ala Asp Ile Arg Ala Ala Ile Pro Lys His Cys Trp Val
            30                  35                  40

AAG AAT CCA TGG AAG TCT ATG AGT TAC GTC GTC AGA GAG CTA GCC ATC         255
Lys Asn Pro Trp Lys Ser Met Ser Tyr Val Val Arg Glu Leu Ala Ile
        45                  50                  55

GTG TTC GCA CTA GCT GCT GGA GCT GCT TAC CTC AAC AAT TGG CTT GTT         303
Val Phe Ala Leu Ala Ala Gly Ala Ala Tyr Leu Asn Asn Trp Leu Val
60                  65                  70                  75

TGG CCT CTC TAT TGG ATT GCT CAA GGA ACC ATG TTC TGG GCT CTC TTT         351
Trp Pro Leu Tyr Trp Ile Ala Gln Gly Thr Met Phe Trp Ala Leu Phe
                80                  85                  90

GTT CTT GGC CAT GAC TGT GGA CAT GGA AGC TTC TCA AAT GAT CCG AGG         399
Val Leu Gly His Asp Cys Gly His Gly Ser Phe Ser Asn Asp Pro Arg
            95                  100                 105
```

| | | | | | | | | | | | | | | |
|---|---|---|---|---|---|---|---|---|---|---|---|---|---|---|
| TTG | AAC | AGT | GTG | GTG | GGT | CAC | CTT | CTT | CAT | TCC | TCT | ATT | CTA | GTC | CCT | 447 |
| Leu | Asn | Ser | Val | Val | Gly | His | Leu | Leu | His | Ser | Ser | Ile | Leu | Val | Pro | |
| | | 110 | | | | | 115 | | | | | 120 | | | | |

```
TTG AAC AGT GTG GTG GGT CAC CTT CTT CAT TCC TCT ATT CTA GTC CCT    447
Leu Asn Ser Val Val Gly His Leu Leu His Ser Ser Ile Leu Val Pro
        110                 115                 120

TAC CAT GGC TGG AGA ATT AGC CAC AGA ACT CAC CAC CAG AAC CAT GGA    495
Tyr His Gly Trp Arg Ile Ser His Arg Thr His His Gln Asn His Gly
        125                 130                 135

CAT GTT GAG AAC GAT GAA TCT TGG CAT CCT ATG TCT GAG AAA ATC TAC    543
His Val Glu Asn Asp Glu Ser Trp His Pro Met Ser Glu Lys Ile Tyr
140                 145                 150                 155

AAG AGT TTG GAC AAA CCC ACT CGG TTC TTT AGA TTT ACA TTG CCT CTC    591
Lys Ser Leu Asp Lys Pro Thr Arg Phe Phe Arg Phe Thr Leu Pro Leu
                160                 165                 170

GTG ATG CTC GCT TAC CCT TTC TAC TTG TGG GCA AGA AGT CCA GGG AAG    639
Val Met Leu Ala Tyr Pro Phe Tyr Leu Trp Ala Arg Ser Pro Gly Lys
            175                 180                 185

AAG GGT TCT CAT TAC CAT CCA GAC AGC GAC TTG TTC CTT CCT AAA GAG    687
Lys Gly Ser His Tyr His Pro Asp Ser Asp Leu Phe Leu Pro Lys Glu
                190                 195                 200

AGA AAC GAT GTT CTC ACT TCT ACC GCT TGT TGG ACT GCA ATG GCT GTT    735
Arg Asn Asp Val Leu Thr Ser Thr Ala Cys Trp Thr Ala Met Ala Val
205                 210                 215

CTG CTT GTC TGT CTC AAC TTC GTG ATG GGT CCA ATG CAA ATG CTC AAA    783
Leu Leu Val Cys Leu Asn Phe Val Met Gly Pro Met Gln Met Leu Lys
220                 225                 230                 235

CTT TAT GTC ATT CCT TAC TGG ATA AAT GTA ATG TGG TTG GAC TTT GTG    831
Leu Tyr Val Ile Pro Tyr Trp Ile Asn Val Met Trp Leu Asp Phe Val
                240                 245                 250

ACT TAC CTG CAT CAC CAT GGT CAT GAA GAT AAG CTC CCT TGG TAC CGT    879
Thr Tyr Leu His His His Gly His Glu Asp Lys Leu Pro Trp Tyr Arg
                255                 260                 265

GGG AAG GAA TGG AGT TAC TTG AGA GGA GGA CTT ACA ACA TTG GAC CGG    927
Gly Lys Glu Trp Ser Tyr Leu Arg Gly Gly Leu Thr Thr Leu Asp Arg
            270                 275                 280

GAC TAC GGA TTG ATC AAC AAC ATC CAT CAC GAC ATT GGA ACT CAT GTG    975
Asp Tyr Gly Leu Ile Asn Asn Ile His His Asp Ile Gly Thr His Val
285                 290                 295

ATA CAT CAT CTT TTC CCT CAG ATC CCA CAT TAT CAT CTA GTA GAA GCA   1023
Ile His His Leu Phe Pro Gln Ile Pro His Tyr His Leu Val Glu Ala
300                 305                 310                 315

ACA GAA GCA GCT AAA CCA GTA TTA GGG AAG TAT TAT AGG GAG CCT GAT   1071
Thr Glu Ala Ala Lys Pro Val Leu Gly Lys Tyr Tyr Arg Glu Pro Asp
                320                 325                 330

AAG TCT GGA CCT TTG CCA TTA CAT TTA CTG GGA ATC TTA GCA AAA AGT   1119
Lys Ser Gly Pro Leu Pro Leu His Leu Leu Gly Ile Leu Ala Lys Ser
                335                 340                 345

ATT AAA GAA GAT CAT TTT GTG AGC GAT GAA GGA GAT GTT GTA TAC TAT   1167
Ile Lys Glu Asp His Phe Val Ser Asp Glu Gly Asp Val Val Tyr Tyr
                350                 355                 360

GAA GCA GAC CCT AAT CTC TAT GGA GAG ATC AAG GTA ACA GCA GAG       1212
Glu Ala Asp Pro Asn Leu Tyr Gly Glu Ile Lys Val Thr Ala Glu
365                 370                 375

TGAAATGAAG CTGTCAGATT TATCTATTTC TGACCAGCTG ATTTTTTTTG CTTATTAATG 1272

TCAATTCATT GTGTTACCAT TATCTCTGAA TACAATCAGA TGGAAACCCC AACTTTGTTT 1332

TCAATACTTG AAGCTATATA TATATATATA TATGTAAGAT ACATTGTATT GTCATTAGAT 1392

TCACCATTCT CAAGGTTCTT ATACAAAAAA AAAAAA                          1429
```

(2) INFORMATION FOR SEQ ID NO:7:

(i) SEQUENCE CHARACTERISTICS:

(A) LENGTH: 378 amino acids
(B) TYPE: amino acid
(D) TOPOLOGY: linear (ii) MOLECULE TYPE: protein (xi) SEQUENCE DESCRIPTION: SEQ ID NO:7:

```
Leu Thr Val Asp Ser Ser Ser Pro Ile Glu Glu Pro Lys
 1               5                  10                  15

Thr Gln Arg Phe Asp Pro Gly Ala Pro Pro Phe Asn Leu Ala Asp
                 20                  25                  30

Ile Arg Ala Ala Ile Pro Lys His Cys Trp Val Lys Asn Pro Trp Lys
         35                  40                  45

Ser Met Ser Tyr Val Val Arg Glu Leu Ala Ile Val Phe Ala Leu Ala
     50                  55                  60

Ala Gly Ala Ala Tyr Leu Asn Asn Trp Leu Val Trp Pro Leu Tyr Trp
 65                  70                  75                  80

Ile Ala Gln Gly Thr Met Phe Trp Ala Leu Phe Val Leu Gly His Asp
                 85                  90                  95

Cys Gly His Gly Ser Phe Ser Asn Asp Pro Arg Leu Asn Ser Val Val
                100                 105                 110

Gly His Leu Leu His Ser Ser Ile Leu Val Pro Tyr His Gly Trp Arg
         115                 120                 125

Ile Ser His Arg Thr His His Gln Asn His Gly His Val Glu Asn Asp
130                 135                 140

Glu Ser Trp His Pro Met Ser Glu Lys Ile Tyr Lys Ser Leu Asp Lys
145                 150                 155                 160

Pro Thr Arg Phe Phe Arg Phe Thr Leu Pro Leu Val Met Leu Ala Tyr
                165                 170                 175

Pro Phe Tyr Leu Trp Ala Arg Ser Pro Gly Lys Lys Gly Ser His Tyr
                180                 185                 190

His Pro Asp Ser Asp Leu Phe Leu Pro Lys Glu Arg Asn Asp Val Leu
        195                 200                 205

Thr Ser Thr Ala Cys Trp Thr Ala Met Ala Val Leu Leu Val Cys Leu
210                 215                 220

Asn Phe Val Met Gly Pro Met Gln Met Leu Lys Leu Tyr Val Ile Pro
225                 230                 235                 240

Tyr Trp Ile Asn Val Met Trp Leu Asp Phe Val Thr Tyr Leu His His
                245                 250                 255

His Gly His Glu Asp Lys Leu Pro Trp Tyr Arg Gly Lys Glu Trp Ser
                260                 265                 270

Tyr Leu Arg Gly Gly Leu Thr Thr Leu Asp Arg Asp Tyr Gly Leu Ile
        275                 280                 285

Asn Asn Ile His His Asp Ile Gly Thr His Val Ile His His Leu Phe
290                 295                 300

Pro Gln Ile Pro His Tyr His Leu Val Glu Ala Thr Glu Ala Ala Lys
305                 310                 315                 320

Pro Val Leu Gly Lys Tyr Tyr Arg Glu Pro Asp Lys Ser Gly Pro Leu
                325                 330                 335

Pro Leu His Leu Leu Gly Ile Leu Ala Lys Ser Ile Lys Glu Asp His
                340                 345                 350

Phe Val Ser Asp Glu Gly Asp Val Val Tyr Tyr Glu Ala Asp Pro Asn
        355                 360                 365

Leu Tyr Gly Glu Ile Lys Val Thr Ala Glu
370                 375
```

(2) INFORMATION FOR SEQ ID NO:8:

(i) SEQUENCE CHARACTERISTICS:
        (A) LENGTH: 1429 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Brassica napus (vii) IMMEDIATE SOURCE:
        (B) CLONE: pBNSFd-2

(ix) FEATURE:
        (A) NAME/KEY: CDS
        (B) LOCATION: 1..1215

(xi) SEQUENCE DESCRIPTION: SEQ ID NO:8:

```
TTC AAA TTC AGA CAA TCC CCT TCT TCT CCC CGG TTT CGT CTG AAC TCT        48
Phe Lys Phe Arg Gln Ser Pro Ser Ser Pro Arg Phe Arg Leu Asn Ser
 1               5                  10                  15

CGA AAC TGG GCG TTG AAT GTA ACC ACA CCT CTA ACA GTC GAC TCC TCA        96
Arg Asn Trp Ala Leu Asn Val Thr Thr Pro Leu Thr Val Asp Ser Ser
             20                  25                  30

TCA TCT CCT CCA ATC GAG GAA GAA CCC AAA ACG CAG AGA TTC GAC CCA       144
Ser Ser Pro Pro Ile Glu Glu Glu Pro Lys Thr Gln Arg Phe Asp Pro
         35                  40                  45

GGC GCT CCT CCT CCG TTC AAC CTA GCT GAC ATC AGA GCG GCG ATA CCT       192
Gly Ala Pro Pro Pro Phe Asn Leu Ala Asp Ile Arg Ala Ala Ile Pro
 50                  55                  60

AAG CAT TGC TGG GTT AAG AAT CCA TGG AAG TCT ATG AGT TAC GTC GTC       240
Lys His Cys Trp Val Lys Asn Pro Trp Lys Ser Met Ser Tyr Val Val
65                  70                  75                  80

AGA GAG CTA GCC ATC GTG TTC GCA CTA GCT GCT GGA GCT GCT TAC CTC       288
Arg Glu Leu Ala Ile Val Phe Ala Leu Ala Ala Gly Ala Ala Tyr Leu
                 85                  90                  95

AAC AAT TGG CTT GTT TGG CCT CTC TAT TGG ATT GCT CAA GGA ACC ATG       336
Asn Asn Trp Leu Val Trp Pro Leu Tyr Trp Ile Ala Gln Gly Thr Met
            100                 105                 110

TTC TGG GCT CTC TTT GTT CTT GGC CAT GAC TGT GGA CAT GGA AGC TTC       384
Phe Trp Ala Leu Phe Val Leu Gly His Asp Cys Gly His Gly Ser Phe
        115                 120                 125

TCA AAT GAT CCG AGG TTG AAC AGT GTG GTG GGT CAC CTT CTT CAT TCC       432
Ser Asn Asp Pro Arg Leu Asn Ser Val Val Gly His Leu Leu His Ser
130                 135                 140

TCT ATT CTA GTC CCT TAC CAT GGC TGG AGA ATT AGC CAC AGA ACT CAC       480
Ser Ile Leu Val Pro Tyr His Gly Trp Arg Ile Ser His Arg Thr His
145                 150                 155                 160

CAC CAG AAC CAT GGA CAT GTT GAG AAC GAT GAA TCT TGG CAT CCT ATG       528
His Gln Asn His Gly His Val Glu Asn Asp Glu Ser Trp His Pro Met
                165                 170                 175

TCT GAG AAA ATC TAC AAG AGT TTG GAC AAA CCC ACT CGG TTC TTT AGA       576
Ser Glu Lys Ile Tyr Lys Ser Leu Asp Lys Pro Thr Arg Phe Phe Arg
            180                 185                 190

TTT ACA TTG CCT CTC GTG ATG CTC GCT TAC CCT TTC TAC TTG TGG GCA       624
Phe Thr Leu Pro Leu Val Met Leu Ala Tyr Pro Phe Tyr Leu Trp Ala
        195                 200                 205

AGA AGT CCA GGG AAG AAG GGT TCT CAT TAC CAT CCA GAC AGC GAC TTG       672
Arg Ser Pro Gly Lys Lys Gly Ser His Tyr His Pro Asp Ser Asp Leu
210                 215                 220
```

```
TTC CTT CCT AAA GAG AGA AAC GAT GTT CTC ACT TCT ACC GCT TGT TGG    720
Phe Leu Pro Lys Glu Arg Asn Asp Val Leu Thr Ser Thr Ala Cys Trp
225                 230                 235                 240

ACT GCA ATG GCT GTT CTG CTT GTC TGT CTC AAC TTC GTG ATG GGT CCA    768
Thr Ala Met Ala Val Leu Leu Val Cys Leu Asn Phe Val Met Gly Pro
                    245                 250                 255

ATG CAA ATG CTC AAA CTT TAT GTC ATT CCT TAC TGG ATA AAT GTA ATG    816
Met Gln Met Leu Lys Leu Tyr Val Ile Pro Tyr Trp Ile Asn Val Met
                260                 265                 270

TGG TTG GAC TTT GTG ACT TAC CTG CAT CAC CAT GGT CAT GAA GAT AAG    864
Trp Leu Asp Phe Val Thr Tyr Leu His His His Gly His Glu Asp Lys
            275                 280                 285

CTC CCT TGG TAC CGT GGG AAG GAA TGG AGT TAC TTG AGA GGA GGA CTT    912
Leu Pro Trp Tyr Arg Gly Lys Glu Trp Ser Tyr Leu Arg Gly Gly Leu
        290                 295                 300

ACA ACA TTG GAC CGG GAC TAC GGA TTG ATC AAC AAC ATC CAT CAC GAC    960
Thr Thr Leu Asp Arg Asp Tyr Gly Leu Ile Asn Asn Ile His His Asp
305                 310                 315                 320

ATT GGA ACT CAT GTG ATA CAT CAT CTT TTC CCT CAG ATC CCA CAT TAT   1008
Ile Gly Thr His Val Ile His His Leu Phe Pro Gln Ile Pro His Tyr
                325                 330                 335

CAT CTA GTA GAA GCA ACA GAA GCA GCT AAA CCA GTA TTA GGG AAG TAT   1056
His Leu Val Glu Ala Thr Glu Ala Ala Lys Pro Val Leu Gly Lys Tyr
                340                 345                 350

TAT AGG GAG CCT GAT AAG TCT GGA CCT TTG CCA TTA CAT TTA CTG GGA   1104
Tyr Arg Glu Pro Asp Lys Ser Gly Pro Leu Pro Leu His Leu Leu Gly
            355                 360                 365

ATC TTA GCA AAA AGT ATT AAA GAA GAT CAT TTT GTG AGC GAT GAA GGA   1152
Ile Leu Ala Lys Ser Ile Lys Glu Asp His Phe Val Ser Asp Glu Gly
370                 375                 380

GAT GTT GTA TAC TAT GAA GCA GAC CCT AAT CTC TAT GGA GAG ATC AAG   1200
Asp Val Val Tyr Tyr Glu Ala Asp Pro Asn Leu Tyr Gly Glu Ile Lys
385                 390                 395                 400

GTA ACA GCA GAG TGAAATGAAG CTGTCAGATT TATCTATTTC TGACCAGCTG       1252
Val Thr Ala Glu
                405

ATTTTTTTTG CTTATTAATG TCAATTCATT GTGTTACCAT TATCTCTGAA TACAATCAGA  1312

TGGAAACCCC AACTTTGTTT TCAATACTTG AAGCTATATA TATATATATA TATGTAAGAT  1372

ACATTGTATT GTCATTAGAT TCACCATTCT CAAGGTTCTT ATACAAAAAA AAAAAAA     1429

(2) INFORMATION FOR SEQ ID NO:9:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:9:

Phe Lys Phe Arg Gln Ser Pro Ser Pro Arg Phe Arg Leu Asn Ser
1               5                   10                  15

Arg Asn Trp Ala Leu Asn Val Thr Thr Pro Leu Thr Val Asp Ser Ser
            20                  25                  30

Ser Ser Pro Pro Ile Glu Glu Glu Pro Lys Thr Gln Arg Phe Asp Pro
        35                  40                  45

Gly Ala Pro Pro Pro Phe Asn Leu Ala Asp Ile Arg Ala Ala Ile Pro
50                  55                  60
```

```
Lys His Cys Trp Val Lys Asn Pro Trp Lys Ser Met Ser Tyr Val Val
 65                  70                  75                  80

Arg Glu Leu Ala Ile Val Phe Ala Leu Ala Ala Gly Ala Ala Tyr Leu
                 85                  90                  95

Asn Asn Trp Leu Val Trp Pro Leu Tyr Trp Ile Ala Gln Gly Thr Met
                100                 105                 110

Phe Trp Ala Leu Phe Val Leu Gly His Asp Cys Gly His Gly Ser Phe
                115                 120                 125

Ser Asn Asp Pro Arg Leu Asn Ser Val Val Gly His Leu Leu His Ser
130                 135                 140

Ser Ile Leu Val Pro Tyr His Gly Trp Arg Ile Ser His Arg Thr His
145                 150                 155                 160

His Gln Asn His Gly His Val Glu Asn Asp Glu Ser Trp His Pro Met
                165                 170                 175

Ser Glu Lys Ile Tyr Lys Ser Leu Asp Lys Pro Thr Arg Phe Phe Arg
                180                 185                 190

Phe Thr Leu Pro Leu Val Met Leu Ala Tyr Pro Phe Tyr Leu Trp Ala
                195                 200                 205

Arg Ser Pro Gly Lys Lys Gly Ser His Tyr His Pro Asp Ser Asp Leu
                210                 215                 220

Phe Leu Pro Lys Glu Arg Asn Asp Val Leu Thr Ser Thr Ala Cys Trp
225                 230                 235                 240

Thr Ala Met Ala Val Leu Leu Val Cys Leu Asn Phe Val Met Gly Pro
                245                 250                 255

Met Gln Met Leu Lys Leu Tyr Val Ile Pro Tyr Trp Ile Asn Val Met
                260                 265                 270

Trp Leu Asp Phe Val Thr Tyr Leu His His Gly His Glu Asp Lys
                275                 280                 285

Leu Pro Trp Tyr Arg Gly Lys Glu Trp Ser Tyr Leu Arg Gly Gly Leu
290                 295                 300

Thr Thr Leu Asp Arg Asp Tyr Gly Leu Ile Asn Asn Ile His His Asp
305                 310                 315                 320

Ile Gly Thr His Val Ile His His Leu Phe Pro Gln Ile Pro His Tyr
                325                 330                 335

His Leu Val Glu Ala Thr Glu Ala Ala Lys Pro Val Leu Gly Lys Tyr
                340                 345                 350

Tyr Arg Glu Pro Asp Lys Ser Gly Pro Leu Pro Leu His Leu Leu Gly
                355                 360                 365

Ile Leu Ala Lys Ser Ile Lys Glu Asp His Phe Val Ser Asp Glu Gly
                370                 375                 380

Asp Val Val Tyr Tyr Glu Ala Asp Pro Asn Leu Tyr Gly Glu Ile Lys
385                 390                 395                 400

Val Thr Ala Glu (2) INFORMATION FOR SEQ ID NO:10:

(i) SEQUENCE CHARACTERISTICS:
        (A) LENGTH: 2181 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Glycine max
```

(vii) IMMEDIATE SOURCE:
    (B) CLONE: pXF1

(ix) FEATURE:
    (A) NAME/KEY: CDS
    (B) LOCATION: 855..1997

(xi) SEQUENCE DESCRIPTION: SEQ ID NO:10:

```
ACAATAATAA ATCCATATTT TTATAATTAA AAGTAGTAGA TTACAGCGAT GCACTTGAGA         60

AACATATTAA GTGGACTAAT TCTCCCTGGT CAAGCAAGAA AAAAACCAGC TATGACCCAA        120

GGTAGAGAGA GATTATACAC AGAATACTAG TAATTAACTA AGACTGGCTC TGCAATTGCC        180

AAAAACTCCA TTGCAGTAGC AGCCACCTGA GAAGACACTA AGACCTAGAC TAGACCATAC        240

ATATGAAGAT TAATACGCTT ACATAACAAC ATAGGACACT AAGAAAACAC GGCTTACAGA        300

GAATCCAGCT GACTCTATAA GAGGGGTACT TCTGGAGATT AAAATTATCC GAATCACCTT        360

CCCACTGCGG CTGCTGACGT CAGCGAAAGT CAGAACCGAA AGCGGCGAAG AACCTTCAGA        420

AGAGGAGGAA GCACTTCGAC CTTACAAGAG TTGTTGTCGT TGTTGTTGTC GTTCTCTGGC        480

GGAGAAGCGA GTTTGGATCG CGTTTTCCTC GGAGGCTTCT CGGTCTTCCC CTGTTTCTGC        540

AGCTCAGCCA GGCCCTCGCA AATGGCCTGA AGCTTGGCGT CAACGGCGGA ATGAAGAGGC        600

TAATACTCCC CGAAGTCACC ACCGACGGAG GAACCCTGGT GTCGGAGGTT GGGGAAGTTG        660

AGCCTGGCGA AGTCACCTCG GAGCTTGTAC GCGGCCTTGT GGTACGCCAG AGCGGCTTCC        720

TCGGCGGTGT CGAAGGTTCC CAGCCATAGC CTGGTCCGGA TTCTTCGGGA GTCTAATCTC        780

AGCCACCCAC TTCCCCCCTG AGAAAAGAGA GGAACCACAC TCTCTAAGCC AAAGCAAAAG        840

CAGCAGCAGC AGCA ATG GTT AAA GAC ACA AAG CCT TTA GCC TAT GCT GCC          890
              Met Val Lys Asp Thr Lys Pro Leu Ala Tyr Ala Ala
                1               5                  10

AAT AAT GGA TAC CAA CAA AAG GGT TCT TCT TTT GAT TTT GAT CCT AGC          938
Asn Asn Gly Tyr Gln Gln Lys Gly Ser Ser Phe Asp Phe Asp Pro Ser
         15                  20                  25

GCT CCT CCA CCG TTT AAG ATT GCA GAA ATC AGA GCT TCA ATA CCA AAA          986
Ala Pro Pro Pro Phe Lys Ile Ala Glu Ile Arg Ala Ser Ile Pro Lys
     30                  35                  40

CAT TGC TGG GTC AAG AAT CCA TGG AGA TCC CTC AGT TAT GTT CTC AGG         1034
His Cys Trp Val Lys Asn Pro Trp Arg Ser Leu Ser Tyr Val Leu Arg
45                  50                  55                  60

GAT GTG CTT GTA ATT GCT GCA TTG GTG GCT GCA GCA ATT CAC TTC GAC         1082
Asp Val Leu Val Ile Ala Ala Leu Val Ala Ala Ala Ile His Phe Asp
                 65                  70                  75

AAC TGG CTT CTC TGG CTA ATC TAT TGC CCC ATT CAA GGC ACA ATG TTC         1130
Asn Trp Leu Leu Trp Leu Ile Tyr Cys Pro Ile Gln Gly Thr Met Phe
             80                  85                  90

TGG GCT CTC TTT GTT CTT GGA CAT GAT TGT GGC CAT GGA AGC TTT TCA         1178
Trp Ala Leu Phe Val Leu Gly His Asp Cys Gly His Gly Ser Phe Ser
         95                 100                 105

GAT AGC CCT TTG CTG AAT AGC CTG GTG GGA CAC ATC TTG CAT TCC TCA         1226
Asp Ser Pro Leu Leu Asn Ser Leu Val Gly His Ile Leu His Ser Ser
    110                 115                 120

ATT CTT GTG CCA TAC CAT GGA TGG AGA ATT AGC CAC AGA ACT CAC CAT         1274
Ile Leu Val Pro Tyr His Gly Trp Arg Ile Ser His Arg Thr His His
125                 130                 135                 140

CAA AAC CAT GGA CAC ATT GAG AAG GAT GAG TCA TGG GTT CCA TTA ACA         1322
Gln Asn His Gly His Ile Glu Lys Asp Glu Ser Trp Val Pro Leu Thr
                145                 150                 155
```

```
GAG AAG ATT TAC AAG AAT CTA GAC AGC ATG ACA AGA CTC ATT AGA TTC    1370
Glu Lys Ile Tyr Lys Asn Leu Asp Ser Met Thr Arg Leu Ile Arg Phe
        160                 165                 170

ACT GTG CCA TTT CCA TTG TTT GTG TAT CCA ATT TAT TTG TTT TCA AGA    1418
Thr Val Pro Phe Pro Leu Phe Val Tyr Pro Ile Tyr Leu Phe Ser Arg
            175                 180                 185

AGC CCC GGA AAG GAA GGC TCT CAC TTC AAT CCC TAC AGC AAT CTG TTC    1466
Ser Pro Gly Lys Glu Gly Ser His Phe Asn Pro Tyr Ser Asn Leu Phe
        190                 195                 200

CCA CCC AGT GAG AGA AAA GGA ATA GCA ATA TCA ACA CTG TGT TGG GCT    1514
Pro Pro Ser Glu Arg Lys Gly Ile Ala Ile Ser Thr Leu Cys Trp Ala
205                 210                 215                 220

ACC ATG TTT TCT CTG CTT ATC TAT CTC TCA TTC ATA ACT AGT CCA CTT    1562
Thr Met Phe Ser Leu Leu Ile Tyr Leu Ser Phe Ile Thr Ser Pro Leu
                225                 230                 235

CTA GTG CTC AAG CTC TAT GGA ATT CCA TAT TGG ATA TTT GTT ATG TGG    1610
Leu Val Leu Lys Leu Tyr Gly Ile Pro Tyr Trp Ile Phe Val Met Trp
            240                 245                 250

CTG GAC TTT GTC ACA TAC TTG CAT CAC CAT GGT CAC CAC CAG AAA CTG    1658
Leu Asp Phe Val Thr Tyr Leu His His His Gly His His Gln Lys Leu
        255                 260                 265

CCT TGG TAC CGC GGC AAG GAA TGG AGT TAT TTA AGA GGT GGC CTC ACC    1706
Pro Trp Tyr Arg Gly Lys Glu Trp Ser Tyr Leu Arg Gly Gly Leu Thr
270                 275                 280

ACT GTG GAT CGT GAC TAT GGT TGG ATC TAT AAC ATT CAC CAT GAC ATT    1754
Thr Val Asp Arg Asp Tyr Gly Trp Ile Tyr Asn Ile His His Asp Ile
285                 290                 295                 300

GGC ACC CAT GTT ATC CAC CAT CTT TTC CCC CAA ATT CCT CAT TAT CAC    1802
Gly Thr His Val Ile His His Leu Phe Pro Gln Ile Pro His Tyr His
                305                 310                 315

CTC GTT GAA GCG ACA CAA GCA GCA AAA CCA GTT CTT GGA GAT TAC TAC    1850
Leu Val Glu Ala Thr Gln Ala Ala Lys Pro Val Leu Gly Asp Tyr Tyr
            320                 325                 330

CGT GAG CCA GAA AGA TCT GCG CCA TTA CCA TTT CAT CTA ATA AAG TAT    1898
Arg Glu Pro Glu Arg Ser Ala Pro Leu Pro Phe His Leu Ile Lys Tyr
        335                 340                 345

TTA ATT CAG AGT ATG AGA CAA GAC CAC TTC GTA AGT GAC ACT GGA GAT    1946
Leu Ile Gln Ser Met Arg Gln Asp His Phe Val Ser Asp Thr Gly Asp
350                 355                 360

GTT GTT TAT TAT CAG ACT GAT TCT CTG CTC CTC CAC TCG CAA CGA GAC    1994
Val Val Tyr Tyr Gln Thr Asp Ser Leu Leu Leu His Ser Gln Arg Asp
365                 370                 375                 380

TGAGTTTCAA ACTTTTTGGG TTATTATTTA TTGGATTCTA GCTACTCAAA TTACTTTTTT    2054

TTTAATGTTA TGTTTTTTGG AGTTTAACGT TTTCTGAACA ACTTGCAAAT TACTTGCATA    2114

GAGAGACATG GAATATTTAT TTGAAATTAG TAAGGTAGTA ATAATAAATT TTGAATTGTC    2174

AGTTTCA    2181
```

(2) INFORMATION FOR SEQ ID NO:11:

(i) SEQUENCE CHARACTERISTICS:
        (A) LENGTH:   380 amino acids
        (B) TYPE:     amino acid
        (D) TOPOLOGY: linear (ii) MOLECULE TYPE: protein (xi) SEQUENCE DESCRIPTION: SEQ ID NO:11:

```
Met Val Lys Asp Thr Lys Pro Leu Ala Tyr Ala Ala Asn Asn Gly Tyr
  1               5                  10                  15
```

```
Gln Gln Lys Gly Ser Ser Phe Asp Phe Asp Pro Ser Ala Pro Pro Pro
             20                  25                  30
Phe Lys Ile Ala Glu Ile Arg Ala Ser Ile Pro Lys His Cys Trp Val
             35                  40                  45
Lys Asn Pro Trp Arg Ser Leu Ser Tyr Val Leu Arg Asp Val Leu Val
 50                  55                  60
Ile Ala Ala Leu Val Ala Ala Ile His Phe Asp Asn Trp Leu Leu
 65                  70                  75                  80
Trp Leu Ile Tyr Cys Pro Ile Gln Gly Thr Met Phe Trp Ala Leu Phe
                 85                  90                  95
Val Leu Gly His Asp Cys Gly His Gly Ser Phe Ser Asp Ser Pro Leu
                100                 105                 110
Leu Asn Ser Leu Val Gly His Ile Leu His Ser Ser Ile Leu Val Pro
             115                 120                 125
Tyr His Gly Trp Arg Ile Ser His Arg Thr His His Gln Asn His Gly
         130                 135                 140
His Ile Glu Lys Asp Glu Ser Trp Val Pro Leu Thr Glu Lys Ile Tyr
145                 150                 155                 160
Lys Asn Leu Asp Ser Met Thr Arg Leu Ile Arg Phe Thr Val Pro Phe
                 165                 170                 175
Pro Leu Phe Val Tyr Pro Ile Tyr Leu Phe Ser Arg Ser Pro Gly Lys
             180                 185                 190
Glu Gly Ser His Phe Asn Pro Tyr Ser Asn Leu Phe Pro Pro Ser Glu
         195                 200                 205
Arg Lys Gly Ile Ala Ile Ser Thr Leu Cys Trp Ala Thr Met Phe Ser
210                 215                 220
Leu Leu Ile Tyr Leu Ser Phe Ile Thr Ser Pro Leu Leu Val Leu Lys
225                 230                 235                 240
Leu Tyr Gly Ile Pro Tyr Trp Ile Phe Val Met Trp Leu Asp Phe Val
             245                 250                 255
Thr Tyr Leu His His His Gly His His Gln Lys Leu Pro Trp Tyr Arg
         260                 265                 270
Gly Lys Glu Trp Ser Tyr Leu Arg Gly Gly Leu Thr Thr Val Asp Arg
     275                 280                 285
Asp Tyr Gly Trp Ile Tyr Asn Ile His His Asp Ile Gly Thr His Val
290                 295                 300
Ile His His Leu Phe Pro Gln Ile Pro His Tyr His Leu Val Glu Ala
305                 310                 315                 320
Thr Gln Ala Ala Lys Pro Val Leu Gly Asp Tyr Tyr Arg Glu Pro Glu
                 325                 330                 335
Arg Ser Ala Pro Leu Pro Phe His Leu Ile Lys Tyr Leu Ile Gln Ser
             340                 345                 350
Met Arg Gln Asp His Phe Val Ser Asp Thr Gly Asp Val Val Tyr Tyr
         355                 360                 365
Gln Thr Asp Ser Leu Leu Leu His Ser Gln Arg Asp
370                 375                 380

(2) INFORMATION FOR SEQ ID NO:12:

(i) SEQUENCE CHARACTERISTICS:
        (A) LENGTH: 1675 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (vi) ORIGINAL SOURCE:
    (A) ORGANISM: Glycine max (vii) IMMEDIATE SOURCE:
    (B) CLONE: pSFD-118bwp (ix) FEATURE:
    (A) NAME/KEY: CDS
    (B) LOCATION: 169..1530

(xi) SEQUENCE DESCRIPTION: SEQ ID NO:12:

```
CTGTGGCAAT TTTTCTCTTC TCCTTCTGGT TCTCATCTTT GTGTTCTTCT TTGTTTCTCA    60

CCTTTCTGAG GATTTTTCCA TCTTAGTTCC TGGAGGCACC AGGAACCTGA CCAAATAAAT   120

AAACCTTTTT TTTCTTCTAA TTTTTCTGAA GTTTCATTTT TTAGTCCA ATG GCA ACT    177
                                                    Met Ala Thr
                                                     1

TGG TAT CAT CAG AAA TGT GGC TTG AAG CCT CTT GCT CCA GTA ATT CCT    225
Trp Tyr His Gln Lys Cys Gly Leu Lys Pro Leu Ala Pro Val Ile Pro
     5              10                  15

AGA CCT AGA ACT GGG GCT GCT TTG TCC AGC ACC TCA AGG GTT GAA TTT    273
Arg Pro Arg Thr Gly Ala Ala Leu Ser Ser Thr Ser Arg Val Glu Phe
 20              25                  30                  35

TTG GAC ACA AAC AAG GTA GTG GCA GGT CCT AAG TTT CAA CCT TTG AGG    321
Leu Asp Thr Asn Lys Val Val Ala Gly Pro Lys Phe Gln Pro Leu Arg
                 40                  45                  50

TGC AAC CTC AGG GAG AGG AAT TGG GGG CTG AAA GTG AGT GCC CCT TTG    369
Cys Asn Leu Arg Glu Arg Asn Trp Gly Leu Lys Val Ser Ala Pro Leu
             55                  60                  65

AGG GTT GCT TCC ATT GAA GAG GAG CAA AAG AGT GTT GAT TTA ACC AAT    417
Arg Val Ala Ser Ile Glu Glu Glu Gln Lys Ser Val Asp Leu Thr Asn
         70                  75                  80

GGG ACT AAT GGG GTT GAG CAT GAG AAG CTT CCA GAA TTT GAC CCT GGT    465
Gly Thr Asn Gly Val Glu His Glu Lys Leu Pro Glu Phe Asp Pro Gly
     85                  90                  95

GCT CCG CCA CCA TTC AAC TTG GCT GAT ATT AGA GCA GCC ATT CCA AAG    513
Ala Pro Pro Pro Phe Asn Leu Ala Asp Ile Arg Ala Ala Ile Pro Lys
100                 105                 110                 115

CAT TGC TGG GTG AAG GAC CCT TGG AGG TCC ATG AGC TAT GTG GTG AGG    561
His Cys Trp Val Lys Asp Pro Trp Arg Ser Met Ser Tyr Val Val Arg
                120                 125                 130

GAT GTG ATT GCT GTC TTT GGT TTG GCT GCT GCT GCG TAT CTC AAT        609
Asp Val Ile Ala Val Phe Gly Leu Ala Ala Ala Ala Tyr Leu Asn
            135                 140                 145

AAT TGG TTG GTT TGG CCT CTC TAT TGG GCT GCT CAA GGC ACT ATG TTC    657
Asn Trp Leu Val Trp Pro Leu Tyr Trp Ala Ala Gln Gly Thr Met Phe
        150                 155                 160

TGG GCT CTG TTT GTT CTT GGT CAT GAT TGT GGT CAT GGA AGC TTT TCA    705
Trp Ala Leu Phe Val Leu Gly His Asp Cys Gly His Gly Ser Phe Ser
    165                 170                 175

AAC AAC TCC AAA TTG AAC AGT GTT GTT GGA CAT CTG CTG CAT TCT TCA    753
Asn Asn Ser Lys Leu Asn Ser Val Val Gly His Leu Leu His Ser Ser
180                 185                 190                 195

ATT CTA GTG CCA TAT CAT GGA TGG AGA ATC AGT CAT AGG ACT CAT CAC    801
Ile Leu Val Pro Tyr His Gly Trp Arg Ile Ser His Arg Thr His His
                200                 205                 210

CAA CAT CAT GGT CAT GCT GAA AAT GAT GAA TCA TGG CAT CCG TTG CCT    849
Gln His His Gly His Ala Glu Asn Asp Glu Ser Trp His Pro Leu Pro
            215                 220                 225
```

```
GAA AAA TTG TTC AGA AGC TTG GAC ACT GTA ACT CGT ATG TTA AGA TTC        897
Glu Lys Leu Phe Arg Ser Leu Asp Thr Val Thr Arg Met Leu Arg Phe
            230                 235                 240

ACA GCA CCT TTT CCA CTT CTT GCA TTT CCT GTG TAC CTT TTT AGT AGG        945
Thr Ala Pro Phe Pro Leu Leu Ala Phe Pro Val Tyr Leu Phe Ser Arg
        245                 250                 255

AGT CCT GGG AAG ACT GGT TCT CAC TTT GAC CCC AGC AGT GAC TTG TTC        993
Ser Pro Gly Lys Thr Gly Ser His Phe Asp Pro Ser Ser Asp Leu Phe
260                 265                 270                 275

GTT CCC AAT GAA AGA AAA GAT GTT ATT ACT TCC ACA GCT TGT TGG GCT       1041
Val Pro Asn Glu Arg Lys Asp Val Ile Thr Ser Thr Ala Cys Trp Ala
                280                 285                 290

GCT ATG TTG GGA TTG CTT GTT GGA TTG GGG TTT GTA ATG GGT CCA ATT       1089
Ala Met Leu Gly Leu Leu Val Gly Leu Gly Phe Val Met Gly Pro Ile
            295                 300                 305

CAA CTT CTT AAG CTT TAT GGT GTT CCC TAT GTT ATA TTC GTT ATG TGG       1137
Gln Leu Leu Lys Leu Tyr Gly Val Pro Tyr Val Ile Phe Val Met Trp
        310                 315                 320

TTG GAT TTG GTG ACT TAT TTG CAC CAT CAT GGC CAT GAA GAC AAA TTA       1185
Leu Asp Leu Val Thr Tyr Leu His His His Gly His Glu Asp Lys Leu
325                 330                 335

CCT TGG TAC CGT GGA AAG GAA TGG AGC TAC CTC AGG GGT GGT CTA ACT       1233
Pro Trp Tyr Arg Gly Lys Glu Trp Ser Tyr Leu Arg Gly Gly Leu Thr
340                 345                 350                 355

ACT CTT GAT CGT GAT TAT GGA TGG ATC AAT AAC ATT CAC CAT GAC ATT       1281
Thr Leu Asp Arg Asp Tyr Gly Trp Ile Asn Asn Ile His His Asp Ile
                360                 365                 370

GGC ACT CAT GTC ATT CAT CAC CTA TTT CCT CAA ATT CCA CAC TAT CAC       1329
Gly Thr His Val Ile His His Leu Phe Pro Gln Ile Pro His Tyr His
            375                 380                 385

TTA GTT GAG GCT ACT GAG GCT GCT AAG CCA GTG TTT GGA AAA TAT TAT       1377
Leu Val Glu Ala Thr Glu Ala Ala Lys Pro Val Phe Gly Lys Tyr Tyr
        390                 395                 400

AGA GAA CCA AAG AAA TCA GCA GCA CCT CTT CCT TTT CAC CTT ATT GGG       1425
Arg Glu Pro Lys Lys Ser Ala Ala Pro Leu Pro Phe His Leu Ile Gly
405                 410                 415

GAA ATA ATA AGG AGC TTC AAG ACT GAC CAT TTT GTT AGT GAC ACG GGG       1473
Glu Ile Ile Arg Ser Phe Lys Thr Asp His Phe Val Ser Asp Thr Gly
420                 425                 430                 435

GAT GTT GTG TAC TAT CAA ACC GAC TCT AAG ATT AAT GGC TCT TCC AAA       1521
Asp Val Val Tyr Tyr Gln Thr Asp Ser Lys Ile Asn Gly Ser Ser Lys
                440                 445                 450

TTA GAG TGAATATTAA AATTCTTTTC TATATAGACA AGAGAGGCTT ATACACAATT        1577
Leu Glu

CTTATTGCTT TAAAGATTGT CTTGAGTTTC TCCGAAAGTT ACTGCACTTA CTTGGAGTTG     1637

AATCCTTCAT TAATAAAGGG ATGGATGGAT CATATAAA                             1675

(2) INFORMATION FOR SEQ ID NO:13:

(i) SEQUENCE CHARACTERISTICS:
        (A) LENGTH:  453 amino acids
        (B) TYPE:    amino acid
        (D) TOPOLOGY: linear (ii) MOLECULE TYPE:  protein (xi) SEQUENCE DESCRIPTION:  SEQ ID NO:13:

Met Ala Thr Trp Tyr His Gln Lys Cys Gly Leu Lys Pro Leu Ala Pro
 1               5                  10                  15

Val Ile Pro Arg Pro Arg Thr Gly Ala Ala Leu Ser Ser Thr Ser Arg
                20                  25                  30
```

```
Val Glu Phe Leu Asp Thr Asn Lys Val Val Ala Gly Pro Lys Phe Gln
     35                  40                  45

Pro Leu Arg Cys Asn Leu Arg Glu Arg Asn Trp Gly Leu Lys Val Ser
 50                  55                  60

Ala Pro Leu Arg Val Ala Ser Ile Glu Glu Gln Lys Ser Val Asp
 65                  70                  75                  80

Leu Thr Asn Gly Thr Asn Gly Val Glu His Glu Lys Leu Pro Glu Phe
                 85                  90                  95

Asp Pro Gly Ala Pro Pro Phe Asn Leu Ala Asp Ile Arg Ala Ala
                100                 105                 110

Ile Pro Lys His Cys Trp Val Lys Asp Pro Trp Arg Ser Met Ser Tyr
             115                 120                 125

Val Val Arg Asp Val Ile Ala Val Phe Gly Leu Ala Ala Ala Ala
 130                 135                 140

Tyr Leu Asn Asn Trp Leu Val Trp Pro Leu Tyr Trp Ala Ala Gln Gly
 145                 150                 155                 160

Thr Met Phe Trp Ala Leu Phe Val Leu Gly His Asp Cys Gly His Gly
             165                 170                 175

Ser Phe Ser Asn Asn Ser Lys Leu Asn Ser Val Val Gly His Leu Leu
             180                 185                 190

His Ser Ser Ile Leu Val Pro Tyr His Gly Trp Arg Ile Ser His Arg
     195                 200                 205

Thr His His Gln His His Gly His Ala Glu Asn Asp Glu Ser Trp His
     210                 215                 220

Pro Leu Pro Glu Lys Leu Phe Arg Ser Leu Asp Thr Val Thr Arg Met
225                 230                 235                 240

Leu Arg Phe Thr Ala Pro Phe Pro Leu Leu Ala Phe Pro Val Tyr Leu
             245                 250                 255

Phe Ser Arg Ser Pro Gly Lys Thr Gly Ser His Phe Asp Pro Ser Ser
             260                 265                 270

Asp Leu Phe Val Pro Asn Glu Arg Lys Asp Val Ile Thr Ser Thr Ala
             275                 280                 285

Cys Trp Ala Ala Met Leu Gly Leu Leu Val Gly Leu Gly Phe Val Met
290                 295                 300

Gly Pro Ile Gln Leu Leu Lys Leu Tyr Gly Val Pro Tyr Val Ile Phe
305                 310                 315                 320

Val Met Trp Leu Asp Leu Val Thr Tyr Leu His His His Gly His Glu
             325                 330                 335

Asp Lys Leu Pro Trp Tyr Arg Gly Lys Glu Trp Ser Tyr Leu Arg Gly
             340                 345                 350

Gly Leu Thr Thr Leu Asp Arg Asp Tyr Gly Trp Ile Asn Asn Ile His
             355                 360                 365

His Asp Ile Gly Thr His Val Ile His His Leu Phe Pro Gln Ile Pro
     370                 375                 380

His Tyr His Leu Val Glu Ala Thr Glu Ala Ala Lys Pro Val Phe Gly
385                 390                 395                 400

Lys Tyr Tyr Arg Glu Pro Lys Lys Ser Ala Ala Pro Leu Pro Phe His
                 405                 410                 415

Leu Ile Gly Glu Ile Ile Arg Ser Phe Lys Thr Asp His Phe Val Ser
             420                 425                 430
```

```
Asp Thr Gly Asp Val Val Tyr Tyr Gln Thr Asp Ser Lys Ile Asn Gly
        435                 440                 445

Ser Ser Lys Leu Glu
    450
```

(2) INFORMATION FOR SEQ ID NO:14:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Zea mays (vii) IMMEDIATE SOURCE:
        (B) CLONE: pPCR20

(ix) FEATURE:
        (A) NAME/KEY: exon
        (B) LOCATION: 31..363

(xi) SEQUENCE DESCRIPTION: SEQ ID NO:14:

```
GGATCCACGC ATCATCAGAA TCACGGTCAC ATCCACAGGG ACGAGTCATG GCACCCGATC    60

ACGGAGAAGC TGTACCGGCA ACTAGAGCCA CGCACCAAGA AGCTGAGATT CACGGTGCCC   120

TTCCCCCTGC TCGCATTCCC CGTCTACCTC TTGTACAGGA GCCCCGGCAA GCTCGGCTCC   180

CACTTCCTTC CCAGCAGCGA CCTGTTCAGC CCCAAGGAGA GAGCGACGT  CATGGTGTCA   240

ACCACCTGCT GGTGCATCAT GCTCGCCTCC CTCCTCGCCA TGGCGTGCGC GTTCGGCCCA   300

CTCCAGGTGC TCAAGATGTA CGGCATCCCA TACCTGGTGT TCGTGATGTG GCTTGACCTG   360

GTGACGTACT TACATCACCA CGGCCACGAT GGATCC                             396
```

(2) INFORMATION FOR SEQ ID NO:15:

(i) SEQUENCE CHARACTERISTICS:
        (A) LENGTH: 126 amino acids
        (B) TYPE: amino acid
        (C) STRANDEDNESS: unknown
        (D) TOPOLOGY: unknown (ii) MOLECULE TYPE: protein (iii) HYPOTHETICAL: YES (v) FRAGMENT TYPE: internal (vi) ORIGINAL SOURCE:
        (A) ORGANISM: Zea mays (vii) IMMEDIATE SOURCE:
        (B) CLONE: pPCR20

(xi) SEQUENCE DESCRIPTION: SEQ ID NO:15:

```
His His Gln Asn His Gly His Ile His Arg Asp Glu Ser Trp His Pro
  1               5                  10                  15

Ile Thr Glu Lys Leu Tyr Arg Gln Leu Glu Pro Arg Thr Lys Lys Leu
                20                  25                  30

Arg Phe Thr Val Pro Phe Pro Leu Leu Ala Phe Pro Val Tyr Leu Leu
            35                  40                  45

Tyr Arg Ser Pro Gly Lys Leu Gly Ser His Phe Leu Pro Ser Ser Asp
        50                  55                  60
```

```
Leu Phe Ser Pro Lys Glu Lys Ser Asp Val Met Val Ser Thr Thr Cys
 65                  70                  75                  80

Trp Cys Ile Met Leu Ala Ser Leu Leu Ala Met Ala Cys Ala Phe Gly
                 85                  90                  95

Pro Leu Gln Val Leu Lys Met Tyr Gly Ile Pro Tyr Leu Val Phe Val
            100                 105                 110

Met Trp Leu Asp Leu Val Thr Tyr Leu His His His Gly His
            115                 120                 125
```

(2) INFORMATION FOR SEQ ID NO:16:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Arabidopsis thaliana (vii) IMMEDIATE SOURCE:
        (B) CLONE: pFadx-2 and pYacp7

(xi) SEQUENCE DESCRIPTION: SEQ ID NO:16:

```
CCTCGAGCTA CGTCAGGGCT AAAACCAGGA ACTGGGCATT GAATGTGGCA ACACCTTTAA    60

CAACTCTTCA GTCTCCATCC GAGGAAGACA GGGAGAGATT CGACCCAGGT GCGCCTCCTC   120

CCTTCAATTT GGCGGATATA AGAGCAGCCA TACCTAAGCA TTGTTGGGTT AAGAATCCAT   180

GGATGTCTAT GAGTTATGTT GTCAGAGATG TTGCTATCGT CTTTGGATTG GCTGCTGTTG   240

CTGCTTACTT CAACAATTGG CTTCTCTGGC CTCTCTACTG GTTCGCTCAA GGAACCATGT   300

TCTGGGCTCT CTTTGTCCTT GGCCATGACT GCGGACATGG TAGCTTCTCG AATGATCCGA   360

GGCTGAACAG TGTGGCTGGT CATCTTCTTC ATTCCTCAAT CCTGGTCCCT TACCATGGCT   420

GGAGGATTAG CCACAGAACT CACCACCAGA ACCATGGTCA TGTCGAGAAT GA           472
```

(2) INFORMATION FOR SEQ ID NO:17:

(i) SEQUENCE CHARACTERISTICS:
        (A) LENGTH: 156 amino acids
        (B) TYPE: amino acid
        (C) STRANDEDNESS: unknown
        (D) TOPOLOGY: unknown (ii) MOLECULE TYPE: protein (iii) HYPOTHETICAL: YES (v) FRAGMENT TYPE: N-terminal (vi) ORIGINAL SOURCE:
        (A) ORGANISM: Arabidopsis thaliana (vii) IMMEDIATE SOURCE:
        (B) CLONE: pFadx-2 and pYacp7

(xi) SEQUENCE DESCRIPTION: SEQ ID NO:17:

```
Ser Ser Tyr Val Arg Ala Lys Thr Arg Asn Trp Ala Leu Asn Val Ala
 1                5                  10                  15

Thr Pro Leu Thr Thr Leu Gln Ser Pro Ser Glu Glu Asp Arg Glu Arg
             20                  25                  30

Phe Asp Pro Gly Ala Pro Pro Phe Asn Leu Ala Asp Ile Arg Ala
             35                  40                  45
```

```
Ala Ile Pro Lys His Cys Trp Val Lys Asn Pro Trp Met Ser Met Ser
     50                  55                  60
```

```
Tyr Val Val Arg Asp Val Ala Ile Val Phe Gly Leu Ala Ala Val Ala
 65                  70                  75                  80
```

```
Ala Tyr Phe Asn Asn Trp Leu Leu Trp Pro Leu Tyr Trp Phe Ala Gln
                 85                  90                  95
```

```
Gly Thr Met Phe Trp Ala Leu Phe Val Leu Gly His Asp Cys Gly His
             100                 105                 110
```

```
Gly Ser Phe Ser Asn Asp Pro Arg Leu Asn Ser Val Ala Gly His Leu
             115                 120                 125
```

```
Leu His Ser Ser Ile Leu Val Pro Tyr His Gly Trp Arg Ile Ser His
             130                 135                 140
```

```
Arg Thr His His Gln Asn His Gly His Val Glu Asn
145                 150                 155
```

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (A) NAME/KEY: misc feature
        (B) LOCATION: 1..11
        (D) OTHER INFORMATION: /note= "N= INOSINE"

(ix) FEATURE:
        (A) NAME/KEY: misc feature
        (B) LOCATION: 12..31
        (D) OTHER INFORMATION: /note= "N= A OR T OR G OR C"

(xi) SEQUENCE DESCRIPTION: SEQ ID NO:18:

CGGGATCCAC NCAYCAYCAR AAYCAYGGNC A                                      31

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: misc feature
        (B) LOCATION: 1..15
        (D) OTHER INFORMATION: /note= "N= INOSINE"

(ix) FEATURE:
        (A) NAME/KEY: misc feature
        (B) LOCATION: 16..35
        (D) OTHER INFORMATION: /note= "N= A OR T OR G OR C"

(xi) SEQUENCE DESCRIPTION: SEQ ID NO:19:

CGGGATCCRT CRTGNCCRTG RTGRTGNARR TANGT                                  35

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: misc feature
        (B) LOCATION: 1..36

(D) OTHER INFORMATION: /note= "N= INOSINE"

(xi) SEQUENCE DESCRIPTION: SEQ ID NO:20:

TTCGTNNTNG GNCAYGAYTG YGGNCAYGGN CAYGGNAGNT TC                42

(2) INFORMATION FOR SEQ ID NO:21:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ix) FEATURE:
            (A) NAME/KEY: misc feature
            (B) LOCATION: 1..36
            (D) OTHER INFORMATION: /note= "N= INOSINE"

(xi) SEQUENCE DESCRIPTION: SEQ ID NO:21:

TTCGTNNTNG GNCAYGAYTG YGGNCAYGGN TCNTTC                       36

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:22:
            GGHCAYGAYT GYGGHCAC                                   18

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:23:

GGHCAYGAYT GYGGHCAT                                           18

(2) INFORMATION FOR SEQ ID NO:24:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:24:

GTACTRTARC CDTGDGTR                                           18

(2) INFORMATION FOR SEQ ID NO:25:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:25:

GTGCTRTARC CDTGDGTR                                           18

(2) INFORMATION FOR SEQ ID NO:26:

(i) SEQUENCE CHARACTERISTICS:
            (A) LENGTH: 23 base pairs
            (B) TYPE: nucleic acid (C) STRANDEDNESS: single
            (D) TOPOLOGY: linear (xi) SEQUENCE DESCRIPTION: SEQ ID NO:26:

GTRCANTARG TRGTRAAYAA YGG                                               23

(2) INFORMATION FOR SEQ ID NO:27:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:27:

GTRCANTADG TRGTRGADAA YGG                                               23

(2) INFORMATION FOR SEQ ID NO:28:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ix) FEATURE:
            (A) NAME/KEY: misc feature
            (B) LOCATION: 1..36
            (D) OTHER INFORMATION: /note= "N= INOSINE"

(xi) SEQUENCE DESCRIPTION: SEQ ID NO:28:

TTCGTNNTNG GNCAYGAYTG YGGNCAYGGN AGNTTT                                 36

(2) INFORMATION FOR SEQ ID NO:29:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ix) FEATURE:
            (A) NAME/KEY: misc feature
            (B) LOCATION: 1..36
            (D) OTHER INFORMATION: /note= "N= INOSINE"

(xi) SEQUENCE DESCRIPTION: SEQ ID NO:29:

TTCGTNNTNG GNCAYGAYTG YGGNCAYGGN TCNTTT                                 36

(2) INFORMATION FOR SEQ ID NO:30:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ix) FEATURE:
            (A) NAME/KEY: misc feature
            (B) LOCATION: 1..38
            (D) OTHER INFORMATION: /note= "N= INOSINE"

(xi) SEQUENCE DESCRIPTION: SEQ ID NO:30:

GTRCTRTANC CNTGNGTNCA NTANGTAGTG RANAAGGG                                38

(2) INFORMATION FOR SEQ ID NO:31:

(i) SEQUENCE CHARACTERISTICS:
            (A) LENGTH: 38 base pairs
            (B) TYPE: nucleic acid

```
        (C) STRANDEDNESS: single
        (D) TOPOLOGY: linear (ix) FEATURE:
        (A) NAME/KEY: misc feature
        (B) LOCATION: 1..38
        (D) OTHER INFORMATION: /note= "N= INOSINE"

(xi) SEQUENCE DESCRIPTION: SEQ ID NO:31:

GTRCTRTANC CNTGNGTNCA NTANGTGGTG RANAAGGG                              38

(2) INFORMATION FOR SEQ ID NO:32:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ix) FEATURE:
        (A) NAME/KEY: misc feature
        (B) LOCATION: 1..135
        (D) OTHER INFORMATION: /note= "N= INOSINE"

(xi) SEQUENCE DESCRIPTION: SEQ ID NO:32:

GTGGTGNGTN CNGTGNGANA NNCKCCANCC GTGGTANGGN ACNANNANGA ANGANGAGTG      60

NANNANGTGN CCNACNANNG AGTTNANNAN NGGNATNTCN GAGAANGANC CGTGNCCGCA     120

NTCGTGNCCN ANNACGAA                                                  138
```